US008080396B2

(12) United States Patent
Shiraga et al.

(10) Patent No.: US 8,080,396 B2
(45) Date of Patent: Dec. 20, 2011

(54) MICROORGANISM PRODUCING AN AMINO ACID OF THE L-GLUTAMIC ACID FAMILY AND A METHOD FOR PRODUCING THE AMINO ACID

(75) Inventors: Seizaburo Shiraga, Kawasaki (JP); Noriko Murayama, Kawasaki (JP); Hiroshi Izui, Kawasaki (JP); Hisao Ito, Kawasaki (JP); Hisashi Yasueda, Kawasaki (JP); Yoshihiro Usuda, Kawasaki (JP); Kazuhiko Matsui, Kawasaki (JP)

(73) Assignee: Ajinomoto Co., Inc., Toyko (JP)

( * ) Notice: Subject to any disclaimer, the term of this patent is extended or adjusted under 35 U.S.C. 154(b) by 98 days.

(21) Appl. No.: 12/555,124

(22) Filed: Sep. 8, 2009

(65) Prior Publication Data

US 2010/0062497 A1    Mar. 11, 2010

Related U.S. Application Data

(63) Continuation of application No. PCT/JP2008/054735, filed on Mar. 14, 2008.

(30) Foreign Application Priority Data

Mar. 14, 2007 (JP) ................................. 2007-065367

(51) Int. Cl.
  C12P 13/24   (2006.01)
  C12P 13/14   (2006.01)
  C12N 9/00    (2006.01)
  C12N 9/02    (2006.01)
  C12N 1/20    (2006.01)
  C12N 15/00   (2006.01)
  C07H 21/04   (2006.01)

(52) U.S. Cl. ........ 435/107; 435/110; 435/183; 435/189; 435/252.3; 435/320.1; 536/23.2

(58) Field of Classification Search ......................... None
See application file for complete search history.

(56) References Cited

U.S. PATENT DOCUMENTS

| | | | |
|---|---|---|---|
| 3,220,929 A | 11/1965 | Kinoshita et al. |
| 3,563,857 A | 2/1971 | Oki et al. |
| 5,378,616 A | 1/1995 | Tujimoto et al. |
| 6,110,714 A | 8/2000 | Matsui et al. |
| 6,331,419 B1 | 12/2001 | Moriya et al. |
| 6,878,533 B2 | 4/2005 | Tsujimoto et al. |
| 6,911,332 B2 | 6/2005 | Usuda et al. |
| 7,026,149 B2 | 4/2006 | Usuda et al. |
| 7,029,893 B2 | 4/2006 | Usuda et al. |
| 7,060,475 B2 | 6/2006 | Usuda et al. |
| 7,090,998 B2 | 8/2006 | Ishikawa et al. |
| 7,160,704 B2 | 1/2007 | Takeshita et al. |
| 7,165,587 B2 | 1/2007 | Tsukagoshi et al. |
| 7,192,747 B2 | 3/2007 | Ono et al. |
| 7,192,748 B2 | 3/2007 | Usuda et al. |
| 7,211,416 B2 | 5/2007 | Asahara et al. |
| 7,211,421 B2 | 5/2007 | Tsujimoto et al. |
| 7,217,543 B2 | 5/2007 | Gunji et al. |
| 7,220,570 B2 | 5/2007 | Usuda et al. |
| 7,223,572 B1 | 5/2007 | Gunji et al. |
| 7,247,459 B1 | 7/2007 | Izui et al. |
| 7,262,035 B2 | 8/2007 | Nakamura et al. |
| 7,306,933 B2 | 12/2007 | Van Dien et al. |
| 7,335,506 B2 | 2/2008 | Gunji et al. |
| 7,344,874 B2 | 3/2008 | Hara et al. |
| 7,439,038 B2 | 10/2008 | Gunji et al. |
| 7,468,262 B2 | 12/2008 | Usuda et al. |
| 7,501,282 B2 | 3/2009 | Hara et al. |
| 2002/0004231 A1 | 1/2002 | Moriya et al. |
| 2002/0155556 A1 | 10/2002 | Imaizumi et al. |
| 2003/0124685 A1 | 7/2003 | Kuwabara et al. |
| 2003/0153058 A1 | 8/2003 | Kuwabara et al. |
| 2004/0265956 A1 | 12/2004 | Takikawa et al. |
| 2005/0233308 A1 | 10/2005 | Nishio et al. |
| 2006/0003424 A1 | 1/2006 | Asakura et al. |
| 2006/0040365 A1 | 2/2006 | Kozlov et al. |
| 2006/0234356 A1 | 10/2006 | Usuda et al. |
| 2006/0234357 A1 | 10/2006 | Usuda et al. |
| 2007/0249017 A1 | 10/2007 | Usuda et al. |
| 2008/0038825 A1 | 2/2008 | Gunji et al. |
| 2008/0199919 A1 | 8/2008 | Gunji et al. |
| 2009/0068712 A1 | 3/2009 | Terashita et al. |
| 2009/0093029 A1 | 4/2009 | Usuda et al. |
| 2009/0104659 A1 | 4/2009 | Smirnov et al. |

FOREIGN PATENT DOCUMENTS

| | | |
|---|---|---|
| EP | 1 004 671 | 5/2000 |
| EP | 1172433 | 1/2002 |
| JP | 32-9393 | 11/1932 |
| JP | 63-119688 | 5/1988 |
| JP | 2003-159065 | 6/2003 |

OTHER PUBLICATIONS

Accession Q8KG07. Oct. 1, 2002.*
Accession A4A2V2. Apr. 3, 2007.*
Accession Q8KG08. Oct. 1, 2002.*
Accession A4A2V1. Apr. 3, 2007.* Eisen et al. Proc Natl Acad Sci U S A. Jul. 9, 2002;99(14):9509-14. Epub Jul. 1, 2002.*
Accession AE006470 (2002).*
Accession AE006470-SEQ ID No. 3 (2002).*
Bianchi et al. J Bacteriol. Mar. 1993;175(6):1590-5.*
Hughes et al. J Bacteriol. Mar. 1998;180(5):1119-28.*
El-Mansi et al. Curr Opin Microbiol. Apr. 2006;9(2):173-9. Epub Mar. 10, 2006.*
Choi, D. K., et al., "Production of L-Ornithine by Arginine Auxotrophic Mutants of *Brevibacterium ketoglutamicum* in Dual Substrate-Limited Continuous Culture," J. Fermentation Bioeng. 1996;81(3):216-219.
Kikuchi, M., et al., Biotechnology of Amino Acid Production, progress in industrial microbiology, vol. 24, pp. 101-116, Kodansha Ltd. Tokyo.
Lee, Y-J., et al., "Genetic manipulation of a primary metabolic pathway for L-ornithine production of *Escherichia coli*," Biotechnol. Lett. 2006;28:1849-1856.
Plachý, J., "Fermentačípříprava ornithinu a citrulinu," Kvasny Prumysl 1987;33:73-75.
International Preliminary Report on Patentability for PCT Patent App. No. PCT/JP2008/054735 (Oct. 8, 2009).

(Continued)

*Primary Examiner* — Christian Fronda
(74) *Attorney, Agent, or Firm* — Shelly Guest Cermak; Cermak Nakajima LLP

(57) ABSTRACT

A microorganism is cultured in a medium, and is able to produce one or two or more kinds of L-amino acids including L-glutamic acid, L-glutamine, L-proline, L-ornithine, L-citrulline and L-arginine, and is modified to increase α-ketoglutarate synthase activity. The L-amino acids are collected from the medium or the cells.

15 Claims, No Drawings

OTHER PUBLICATIONS

U.S. Appl. No. 11/844,559, Hara et al., filed Aug. 24, 2007.
U.S. Appl. No. 12/055,438, Iwatani et al., filed Mar. 26, 2008.
U.S. Appl. No. 12/179,845, Chinen et al., filed Jul. 25, 2008.
U.S. Appl. No. 12/184,598, Gunji et al., filed Aug. 1, 2008.
U.S. Appl. No. 12/354,042, Ptitsyn et al., filed Jan. 15, 2009.
U.S. Appl. No. 12/388,133, Hara et al., filed Feb. 18, 2009.
U.S. Appl. No. 12/420,934, Tajima et al., filed Apr. 9, 2009.
U.S. Appl. No. 12/478,049, Hara et al., filed Jun. 4, 2009.
U.S. Appl. No. 12/479,010, Usuda et al., filed Jun. 5, 2009.
U.S. Appl. No. 12/533,061, Asakura et al., filed Jul. 31, 2009.
Allison, M. J., et al., "Synthesis of α-Ketoglutarate by Reductive Carboxylation of Succinate in *Veillonella*, *Selenomonas*, and *Bacteroides* Species," J. Bacteriol. 1979;140(3):980-986.
Bianchi, V., et al., "*Escherichia coli* Ferredoxin NADP Reductase: Activation of *E. coli* Anaerobic Ribonucleotide Reduction, Cloning of the Gene (*fpr*), and Overexpression of the Protein," J. Bacteriol. 1993;175(6):1590-1595.
Database DDBJ/EMBL/GenBank [online], Accession No. NP_661068.
Database DDBJ/EMBL/GenBank [online], Accession No. NP_661069.
Database DDBJ/EMBL/GenBank [online], Accession No. EAQ76902.
Database DDBJ/EMBL/GenBank [online], Accession No. EAQ76903.
Dörner, E., et al., "Properties of 2-Oxoglutarate:Ferredoxin Oxidoreductase from *Thauera aromatic* and Its Role in Enzymatic Reduction of the Aromatic Ring," J. Bacteriol. 2002;184(14):3975-3983.
Fuchs, G., et al., "Acetate Assimilation and the Synthesis of Alanine, Aspartate and Glutamate in *Methanobacterium thermoautotrophicum*," Arch. Microbiol. 1978;117:61-66.
Hughes, N. J., et al., "*Helicobacter pylori porCDAB and oorDABC* Genes Encode Distinct Pyruvate:Flavodoxin and 2-Oxoglutarate:Acceptor Oxidoreductases Which Mediate Electron Transport to NADP," J. Bacteriol. 1998;180(5)1119-1128.
Kather, B., et al., "Another Unusual Type of Citric Acid Cycle Enzyme in *Helicobacter pylori*: the Malate:Quinone Oxidoreductase," J. Bacteriol. 2000;182(11):3204-3209.
Shiba, H., et al., "The $CO_2$ assimilation via the reductive tricarboxylic acid cycle in an obligately autotrophic, aerobic hydrogen-oxidizing bacterium, *Hydrogenobacter thermophilus*," Arch. Microbiol. 1985;141:198-203.
Yamamoto, M., et al., "Characterization of two different 2-oxoglutarate:ferredoxin oxidoreductases from *Hydrogenobacter thermophitus* TK-6," Biochem. Biophys. Res. Comm. 2003;312:1297-1302.
Yun, N-R., et al., "The Genes for Anabolic 2-Oxoglutarate:Ferredoxin Oxidoreductase from Hydrogenobacter thermophiles TK-6," Biochem. Biophys. Res. Comm. 2001;282:589-594.
Yun, N-R., et al., "A Novel Five-Subunit-Type 2-0xoglutalate:Ferredoxin Oxidoreductases from Hydrogenobacter thermophiles TK-6," Biochem. Biophys. Res. Comm. 2002;292:280-286.
Zhang, Q., et al., "2-Oxoacid:Ferredoxin Oxidoreductase from the Thermoacidophilic Archaeon, *Sulfolobus* sp. Strain 7," J. Biochem. 1996;120(3):587-599.
International Search Report for PCT Patent App. No. PCT/JP2008/054735 (Jun. 24, 2008).
NCBI Reference Sequence: ZP_01094415.1; ferredoxin oxidoreductase beta subunit [Blastopirellula marina DSM 3645]; GenBank Database.
NCBI Reference Sequence: ZP_01094416.1; 2-oxoglutarate ferredoxin oxidoreductase alpha subunit [Blastopirellula marina DSM 3645]; GenBank Database.
Yun, N-R., et al., "The Genes for Anabolic 2-0xoglutarate: Ferredoxin Oxidoreductase from *Hydrogenobacter thermophilus* TK-6," Biochem. Biophys. Res. Comm. 2001;282:589-594.
The First Office Action for Chinese Patent App. No. 200880008072.3 (May 25, 2011) with English translation thereof.
Dörner, E., et al., "Properties of 2-Oxoglutarate:Ferredoxin Oxidoreductase from *Thauera aromatica* and Its Role in Enzymatic Reduction of the Aromatic Ring," J. Bacteriol. 2002 184(14):3975-3983.

\* cited by examiner

SEQUENCE LISTING

```
<160> NUMBER OF SEQ ID NOS: 77

<210> SEQ ID NO 1
<211> LENGTH: 1884
<212> TYPE: DNA
<213> ORGANISM: Chlorobium tepidum
<220> FEATURE:
```

-continued

<221> NAME/KEY: CDS
<222> LOCATION: (1)..(1884)

<400> SEQUENCE: 1

```
atg agt gac acc gta atc tta aac aac aat gac atg gta ata tca aaa      48
Met Ser Asp Thr Val Ile Leu Asn Asn Asn Asp Met Val Ile Ser Lys
1               5                   10                  15 acc aac gtg tca gtg ctt ttt gcc ggt gac tcc ggt gac ggc atg cag      96
Thr Asn Val Ser Val Leu Phe Ala Gly Asp Ser Gly Asp Gly Met Gln
            20                  25                  30 ctt acc ggc acc cag ttc gcc aac acg gtg gcc gtt tac ggc tcg gat     144
Leu Thr Gly Thr Gln Phe Ala Asn Thr Val Ala Val Tyr Gly Ser Asp
        35                  40                  45 ttg aac acc ttt ccg aac ttt cct tcg gaa atc aga cct cct gcc ggt     192
Leu Asn Thr Phe Pro Asn Phe Pro Ser Glu Ile Arg Pro Pro Ala Gly
    50                  55                  60 act gtg gca ggc gta tcg ggc ttt cag ttg cag ttt ggc aca acc ggc     240
Thr Val Ala Gly Val Ser Gly Phe Gln Leu Gln Phe Gly Thr Thr Gly
65                  70                  75                  80 gtc tat act ccg ggc gcg aag ttc gat gtc atg atc gcc atg aac gct     288
Val Tyr Thr Pro Gly Ala Lys Phe Asp Val Met Ile Ala Met Asn Ala
                85                  90                  95 gcc gcg ctg aag gca aac ctg aag aac ctg cac cat ggt ggc atc atc     336
Ala Ala Leu Lys Ala Asn Leu Lys Asn Leu His His Gly Gly Ile Ile
            100                 105                 110 att gct gat acc gac ggg ttc gac gca aag aac ctg aac ctt gct ggt     384
Ile Ala Asp Thr Asp Gly Phe Asp Ala Lys Asn Leu Asn Leu Ala Gly
        115                 120                 125 tac ggt gaa acc aac aat ccg ctc gaa gac ggc acg ctg act gat tat     432
Tyr Gly Glu Thr Asn Asn Pro Leu Glu Asp Gly Thr Leu Thr Asp Tyr
    130                 135                 140 acc gta ttc aaa att ccg gta atc agc ctc acc cgc cag gcg ctt gcc     480
Thr Val Phe Lys Ile Pro Val Ile Ser Leu Thr Arg Gln Ala Leu Ala
145                 150                 155                 160 gat aca ggc ctg agc acc aag atc atc gac cgc tgc aaa aac atg ttc     528
Asp Thr Gly Leu Ser Thr Lys Ile Ile Asp Arg Cys Lys Asn Met Phe
                165                 170                 175 gtg ctc ggc gtg ctc tac tgg ctc tac agc ctg cca ctc gaa acc acg     576
Val Leu Gly Val Leu Tyr Trp Leu Tyr Ser Leu Pro Leu Glu Thr Thr
            180                 185                 190 atc gag gca ttg cag tca aaa ttc aag aat aaa cag gac att gcc gag     624
Ile Glu Ala Leu Gln Ser Lys Phe Lys Asn Lys Gln Asp Ile Ala Glu
        195                 200                 205 gcc aac atc aaa gcc gtc aag gca ggc tac aac ttc ggc gat gaa acc     672
Ala Asn Ile Lys Ala Val Lys Ala Gly Tyr Asn Phe Gly Asp Glu Thr
    210                 215                 220 gaa atg ttc tca cag cat ggt cgt ttt tgt gtc cct ccg gcc cag aaa     720
Glu Met Phe Ser Gln His Gly Arg Phe Cys Val Pro Pro Ala Gln Lys
225                 230                 235                 240 aaa aag ggt gtt tat cgc cgc gtg act ggc aac gaa gct tcg gct atc     768
Lys Lys Gly Val Tyr Arg Arg Val Thr Gly Asn Glu Ala Ser Ala Ile
                245                 250                 255 ggt ctt gcc gct gcc gcc caa aag gct gga ctg gaa ctc ttt ctc ggc     816
Gly Leu Ala Ala Ala Ala Gln Lys Ala Gly Leu Glu Leu Phe Leu Gly
            260                 265                 270 tcc tat ccg atc acc ccg gct tcc gaa att ctc cag acc ctt gcc ggc     864
Ser Tyr Pro Ile Thr Pro Ala Ser Glu Ile Leu Gln Thr Leu Ala Gly
        275                 280                 285 ttg aaa aag tgg ggc gtc aaa acg ttc cag gct gaa gac gaa ata gcc     912
Leu Lys Lys Trp Gly Val Lys Thr Phe Gln Ala Glu Asp Glu Ile Ala
    290                 295                 300
```

```
ggt atc ctg acc agc atc ggc gcg gcc tat gga ggt gcg ctt gcc gcc      960
Gly Ile Leu Thr Ser Ile Gly Ala Ala Tyr Gly Gly Ala Leu Ala Ala
305                 310                 315                 320 acc aac acc tcc ggc ccc ggt ctg gcg ctc aaa acc gaa ggg atg ggt     1008
Thr Asn Thr Ser Gly Pro Gly Leu Ala Leu Lys Thr Glu Gly Met Gly
            325                 330                 335 ttg gcg gtt atc ctc gaa ctt ccg ctg gtg atc atc aat gtg atg cgc     1056
Leu Ala Val Ile Leu Glu Leu Pro Leu Val Ile Ile Asn Val Met Arg
        340                 345                 350 ggc ggc ccg tcc acc ggt ctg ccg acc aag ccg gag cag tcc gat ctg     1104
Gly Gly Pro Ser Thr Gly Leu Pro Thr Lys Pro Glu Gln Ser Asp Leu
    355                 360                 365 ctc atg gct atg tac gga cgt cac ggc gaa gcg ccg atg ccg gtc atc     1152
Leu Met Ala Met Tyr Gly Arg His Gly Glu Ala Pro Met Pro Val Ile
370                 375                 380 gcg gcc atg tcg ccg gtt gac tgc ttc tac gcc gcc tac gaa gcc gcg     1200
Ala Ala Met Ser Pro Val Asp Cys Phe Tyr Ala Ala Tyr Glu Ala Ala
385                 390                 395                 400 aag atc gcc gtc gag tac atg act cct gtc ctt tgc ctc acc gac ggc     1248
Lys Ile Ala Val Glu Tyr Met Thr Pro Val Leu Cys Leu Thr Asp Gly
            405                 410                 415 tac ctc gca ctc agc tct gag ccg atg ctg gtg cca tcg ccg gac gag     1296
Tyr Leu Ala Leu Ser Ser Glu Pro Met Leu Val Pro Ser Pro Asp Glu
        420                 425                 430 ctg gcc tcg atc act ccc atg ttc tcg cca gag cgc aaa gcc gac gat     1344
Leu Ala Ser Ile Thr Pro Met Phe Ser Pro Glu Arg Lys Ala Asp Asp
    435                 440                 445 ccg ccg tat ctg ccg tac aag cgc gac gag cgc tgc gtc agg ccg tgg     1392
Pro Pro Tyr Leu Pro Tyr Lys Arg Asp Glu Arg Cys Val Arg Pro Trp
450                 455                 460 ggc atc ccc ggc aca cct ggt ctc gaa cac cgc atc ggc ggt ctc gaa     1440
Gly Ile Pro Gly Thr Pro Gly Leu Glu His Arg Ile Gly Gly Leu Glu
465                 470                 475                 480 aag cag aat gaa acc ggc cac gtt tcg cac gat ccg gaa aac cat gca     1488
Lys Gln Asn Glu Thr Gly His Val Ser His Asp Pro Glu Asn His Ala
            485                 490                 495 ctc atg acc aga ttg cgt gct gaa aag gtt gca aag gtc gcc gat att     1536
Leu Met Thr Arg Leu Arg Ala Glu Lys Val Ala Lys Val Ala Asp Ile
        500                 505                 510 att cct gat ctc acc atc gac aac ggc ccg gaa aaa ggc gat ctg ctc     1584
Ile Pro Asp Leu Thr Ile Asp Asn Gly Pro Glu Lys Gly Asp Leu Leu
    515                 520                 525 gtc ctc ggc tgg ggt tcg acc tat ggc gcc atc aag aaa gcc gtc gag     1632
Val Leu Gly Trp Gly Ser Thr Tyr Gly Ala Ile Lys Lys Ala Val Glu
530                 535                 540 cag gct cgc gaa ggc gga ctt gac gtt gcc cac gcg cac ctc cgc tat     1680
Gln Ala Arg Glu Gly Gly Leu Asp Val Ala His Ala His Leu Arg Tyr
545                 550                 555                 560 atc aac ccg ttc ccg aaa aat ctc ggc gcg atg ctc gga aac ttc aaa     1728
Ile Asn Pro Phe Pro Lys Asn Leu Gly Ala Met Leu Gly Asn Phe Lys
            565                 570                 575 aaa gtg ctg att ccc gaa aac aac tgc ggg cag ctg ctc agc ctc atc     1776
Lys Val Leu Ile Pro Glu Asn Asn Cys Gly Gln Leu Leu Ser Leu Ile
        580                 585                 590 agg gac aag ttc ctc atc gaa ccg gtc ggc ttc agc aag gtt cag ggc     1824
Arg Asp Lys Phe Leu Ile Glu Pro Val Gly Phe Ser Lys Val Gln Gly
    595                 600                 605 ctg ccg ttc aac gag atg gaa atc gaa gaa aaa atc acc gat atc tta     1872
Leu Pro Phe Asn Glu Met Glu Ile Glu Glu Lys Ile Thr Asp Ile Leu
610                 615                 620
```

```
            aag gag ctc tga                                                 1884
            Lys Glu Leu
            625
```

<210> SEQ ID NO 2
<211> LENGTH: 627
<212> TYPE: PRT
<213> ORGANISM: Chlorobium tepidum

<400> SEQUENCE: 2

```
Met Ser Asp Thr Val Ile Leu Asn Asn Asp Met Val Ile Ser Lys
1               5                   10                  15

Thr Asn Val Ser Val Leu Phe Ala Gly Asp Ser Gly Asp Gly Met Gln
            20                  25                  30

Leu Thr Gly Thr Gln Phe Ala Asn Thr Val Ala Val Tyr Gly Ser Asp
            35                  40                  45

Leu Asn Thr Phe Pro Asn Phe Pro Ser Glu Ile Arg Pro Pro Ala Gly
50                  55                  60

Thr Val Ala Gly Val Ser Gly Phe Gln Leu Gln Phe Gly Thr Thr Gly
65                  70                  75                  80

Val Tyr Thr Pro Gly Ala Lys Phe Asp Val Met Ile Ala Met Asn Ala
                85                  90                  95

Ala Ala Leu Lys Ala Asn Leu Lys Asn Leu His His Gly Gly Ile Ile
            100                 105                 110

Ile Ala Asp Thr Asp Gly Phe Asp Ala Lys Asn Leu Asn Leu Ala Gly
            115                 120                 125

Tyr Gly Glu Thr Asn Asn Pro Leu Glu Asp Gly Thr Leu Thr Asp Tyr
            130                 135                 140

Thr Val Phe Lys Ile Pro Val Ile Ser Leu Thr Arg Gln Ala Leu Ala
145                 150                 155                 160

Asp Thr Gly Leu Ser Thr Lys Ile Ile Asp Arg Cys Lys Asn Met Phe
                165                 170                 175

Val Leu Gly Val Leu Tyr Trp Leu Tyr Ser Leu Pro Leu Glu Thr Thr
            180                 185                 190

Ile Glu Ala Leu Gln Ser Lys Phe Lys Asn Lys Gln Asp Ile Ala Glu
            195                 200                 205

Ala Asn Ile Lys Ala Val Lys Ala Gly Tyr Asn Phe Gly Asp Glu Thr
            210                 215                 220

Glu Met Phe Ser Gln His Gly Arg Phe Cys Val Pro Pro Ala Gln Lys
225                 230                 235                 240

Lys Lys Gly Val Tyr Arg Arg Val Thr Gly Asn Glu Ala Ser Ala Ile
                245                 250                 255

Gly Leu Ala Ala Ala Ala Gln Lys Ala Gly Leu Glu Leu Phe Leu Gly
            260                 265                 270

Ser Tyr Pro Ile Thr Pro Ala Ser Glu Ile Leu Gln Thr Leu Ala Gly
            275                 280                 285

Leu Lys Lys Trp Gly Val Lys Thr Phe Gln Ala Glu Asp Glu Ile Ala
            290                 295                 300

Gly Ile Leu Thr Ser Ile Gly Ala Ala Tyr Gly Ala Leu Ala Ala
305                 310                 315                 320

Thr Asn Thr Ser Gly Pro Gly Leu Ala Leu Lys Thr Glu Gly Met Gly
                325                 330                 335

Leu Ala Val Ile Leu Glu Leu Pro Leu Val Ile Asn Val Met Arg
            340                 345                 350

Gly Gly Pro Ser Thr Gly Leu Pro Thr Lys Pro Glu Gln Ser Asp Leu
```

```
                   355                 360                 365
Leu Met Ala Met Tyr Gly Arg His Gly Glu Ala Pro Met Pro Val Ile
    370                 375                 380

Ala Ala Met Ser Pro Val Asp Cys Phe Tyr Ala Ala Tyr Glu Ala Ala
385                 390                 395                 400

Lys Ile Ala Val Glu Tyr Met Thr Pro Val Leu Cys Leu Thr Asp Gly
                405                 410                 415

Tyr Leu Ala Leu Ser Ser Glu Pro Met Leu Val Pro Ser Pro Asp Glu
            420                 425                 430

Leu Ala Ser Ile Thr Pro Met Phe Ser Pro Glu Arg Lys Ala Asp Asp
        435                 440                 445

Pro Pro Tyr Leu Pro Tyr Lys Arg Asp Glu Arg Cys Val Arg Pro Trp
    450                 455                 460

Gly Ile Pro Gly Thr Pro Gly Leu Glu His Arg Ile Gly Gly Leu Glu
465                 470                 475                 480

Lys Gln Asn Glu Thr Gly His Val Ser His Asp Pro Glu Asn His Ala
                485                 490                 495

Leu Met Thr Arg Leu Arg Ala Glu Lys Val Ala Lys Val Ala Asp Ile
            500                 505                 510

Ile Pro Asp Leu Thr Ile Asp Asn Gly Pro Glu Lys Gly Asp Leu Leu
        515                 520                 525

Val Leu Gly Trp Gly Ser Thr Tyr Gly Ala Ile Lys Lys Ala Val Glu
    530                 535                 540

Gln Ala Arg Glu Gly Gly Leu Asp Val Ala His Ala His Leu Arg Tyr
545                 550                 555                 560

Ile Asn Pro Phe Pro Lys Asn Leu Gly Ala Met Leu Gly Asn Phe Lys
                565                 570                 575

Lys Val Leu Ile Pro Glu Asn Asn Cys Gly Gln Leu Leu Ser Leu Ile
            580                 585                 590

Arg Asp Lys Phe Leu Ile Glu Pro Val Gly Phe Ser Lys Val Gln Gly
        595                 600                 605

Leu Pro Phe Asn Glu Met Glu Ile Glu Glu Lys Ile Thr Asp Ile Leu
    610                 615                 620

Lys Glu Leu
625

<210> SEQ ID NO 3
<211> LENGTH: 1029
<212> TYPE: DNA
<213> ORGANISM: Chlorobium tepidum
<220> FEATURE:
<221> NAME/KEY: CDS
<222> LOCATION: (1)..(1029)

<400> SEQUENCE: 3 atg acc gat aca cat acc tgc ctt acc gcc aag gat ttc acg tcg aac      48
Met Thr Asp Thr His Thr Cys Leu Thr Ala Lys Asp Phe Thr Ser Asn
1               5                   10                  15 cag gaa ccg aaa tgg tgc ccc ggc tgt ggt gac ttc atg gtt ctc cag      96
Gln Glu Pro Lys Trp Cys Pro Gly Cys Gly Asp Phe Met Val Leu Gln
            20                  25                  30 caa ctc aag aac gcg atg gct gaa ctg tgc ctg aaa acc gaa gag gtt     144
Gln Leu Lys Asn Ala Met Ala Glu Leu Cys Leu Lys Thr Glu Glu Val
        35                  40                  45 gtc gtg gta tcg ggc att ggc tgc tcg tca agg ctg cca tac tat atc     192
Val Val Val Ser Gly Ile Gly Cys Ser Ser Arg Leu Pro Tyr Tyr Ile
    50                  55                  60
```

```
aac acc tac ggc gtg cac ggc atc cac ggg cgc gcc atg gcg atg gct        240
Asn Thr Tyr Gly Val His Gly Ile His Gly Arg Ala Met Ala Met Ala
 65                  70                  75                  80 tcc ggt ctg aag gtt gcc cgc cct gac ctc agc gtc tgg gtc ggc acc        288
Ser Gly Leu Lys Val Ala Arg Pro Asp Leu Ser Val Trp Val Gly Thr
                 85                  90                  95 ggc gat ggc gac gcc ctc tcc atc ggc ggc aac cat tac atc cac acg        336
Gly Asp Gly Asp Ala Leu Ser Ile Gly Gly Asn His Tyr Ile His Thr
            100                 105                 110 gtc aga cgg aac ctc gac atc aac gtc gtg ctg ttc aac aac gag att        384
Val Arg Arg Asn Leu Asp Ile Asn Val Val Leu Phe Asn Asn Glu Ile
        115                 120                 125 tac ggc ctg acc aag gga cag tac tcg ccg acc tcg aaa gtg ggt ttg        432
Tyr Gly Leu Thr Lys Gly Gln Tyr Ser Pro Thr Ser Lys Val Gly Leu
    130                 135                 140 aga acc gtc acc tct ccg acc ggc gtg gtg gat tat ccg atc aac acc        480
Arg Thr Val Thr Ser Pro Thr Gly Val Val Asp Tyr Pro Ile Asn Thr
145                 150                 155                 160 atc gcc ctc acc ctt ggc gca gga ggc acc ttc gtg gcc cgc gtc atg        528
Ile Ala Leu Thr Leu Gly Ala Gly Gly Thr Phe Val Ala Arg Val Met
                165                 170                 175 gat cgc gac ggc aag ctg atg aag gag att ttc aag cgc gcc cac aac        576
Asp Arg Asp Gly Lys Leu Met Lys Glu Ile Phe Lys Arg Ala His Asn
            180                 185                 190 cac aaa ggc acc tcg atc gtc gag att tac cag aac tgc ccg att ttc        624
His Lys Gly Thr Ser Ile Val Glu Ile Tyr Gln Asn Cys Pro Ile Phe
        195                 200                 205 aac gac ggc gcg ttt aga gcc ttc agc gac aag gag cgg aag gac gac        672
Asn Asp Gly Ala Phe Arg Ala Phe Ser Asp Lys Glu Arg Lys Asp Asp
    210                 215                 220 acg acg ctt tac ctc gaa cag ggc cag ccg ctg gtg ttc ggt gcg aac        720
Thr Thr Leu Tyr Leu Glu Gln Gly Gln Pro Leu Val Phe Gly Ala Asn
225                 230                 235                 240 ggc tcg aag ggc atc tac ctc gac ggt ttc aaa cca acg gtg att gac        768
Gly Ser Lys Gly Ile Tyr Leu Asp Gly Phe Lys Pro Thr Val Ile Asp
                245                 250                 255 ctc gaa aaa tcg ggc gtt tca aaa gat gac ctc tgg att cac gac gaa        816
Leu Glu Lys Ser Gly Val Ser Lys Asp Asp Leu Trp Ile His Asp Glu
            260                 265                 270 aac gac ctc atc aag gca aac atc ctg tcg cgc ttc ttc gac gat ccg        864
Asn Asp Leu Ile Lys Ala Asn Ile Leu Ser Arg Phe Phe Asp Asp Pro
        275                 280                 285 aac agc acc gag gag ttc ctc ccg agg ccg ttc ggt atc ttc tat gtg        912
Asn Ser Thr Glu Glu Phe Leu Pro Arg Pro Phe Gly Ile Phe Tyr Val
    290                 295                 300 gag gat cgc ttc acc tac gaa cag gct ctg agc gcc cag atc gac aag        960
Glu Asp Arg Phe Thr Tyr Glu Gln Ala Leu Ser Ala Gln Ile Asp Lys
305                 310                 315                 320 gcg cag gaa aaa ggc gaa ggc acc ctc gaa gaa ctg ctt gct ggc aac       1008
Ala Gln Glu Lys Gly Glu Gly Thr Leu Glu Glu Leu Leu Ala Gly Asn
                325                 330                 335 agc acc tgg acg atc aac tga                                           1029
Ser Thr Trp Thr Ile Asn
            340

<210> SEQ ID NO 4
<211> LENGTH: 342
<212> TYPE: PRT
<213> ORGANISM: Chlorobium tepidum

<400> SEQUENCE: 4
```

```
Met Thr Asp Thr His Thr Cys Leu Thr Ala Lys Asp Phe Thr Ser Asn
1               5                   10                  15

Gln Glu Pro Lys Trp Cys Pro Gly Cys Gly Asp Phe Met Val Leu Gln
            20                  25                  30

Gln Leu Lys Asn Ala Met Ala Glu Leu Cys Leu Lys Thr Glu Glu Val
        35                  40                  45

Val Val Val Ser Gly Ile Gly Cys Ser Ser Arg Leu Pro Tyr Tyr Ile
    50                  55                  60

Asn Thr Tyr Gly Val His Gly Ile His Gly Arg Ala Met Ala Met Ala
65                  70                  75                  80

Ser Gly Leu Lys Val Ala Arg Pro Asp Leu Ser Val Trp Val Gly Thr
            85                  90                  95

Gly Asp Gly Asp Ala Leu Ser Ile Gly Gly Asn His Tyr Ile His Thr
            100                 105                 110

Val Arg Arg Asn Leu Asp Ile Asn Val Val Leu Phe Asn Asn Glu Ile
        115                 120                 125

Tyr Gly Leu Thr Lys Gly Gln Tyr Ser Pro Thr Ser Lys Val Gly Leu
    130                 135                 140

Arg Thr Val Thr Ser Pro Thr Gly Val Val Asp Tyr Pro Ile Asn Thr
145                 150                 155                 160

Ile Ala Leu Thr Leu Gly Ala Gly Gly Thr Phe Val Ala Arg Val Met
                165                 170                 175

Asp Arg Asp Gly Lys Leu Met Lys Glu Ile Phe Lys Arg Ala His Asn
            180                 185                 190

His Lys Gly Thr Ser Ile Val Glu Ile Tyr Gln Asn Cys Pro Ile Phe
        195                 200                 205

Asn Asp Gly Ala Phe Arg Ala Phe Ser Asp Lys Glu Arg Lys Asp Asp
210                 215                 220

Thr Thr Leu Tyr Leu Glu Gln Gly Gln Pro Leu Val Phe Gly Ala Asn
225                 230                 235                 240

Gly Ser Lys Gly Ile Tyr Leu Asp Gly Phe Lys Pro Thr Val Ile Asp
                245                 250                 255

Leu Glu Lys Ser Gly Val Ser Lys Asp Asp Leu Trp Ile His Asp Glu
            260                 265                 270

Asn Asp Leu Ile Lys Ala Asn Ile Leu Ser Arg Phe Phe Asp Asp Pro
        275                 280                 285

Asn Ser Thr Glu Glu Phe Leu Pro Arg Pro Phe Gly Ile Phe Tyr Val
    290                 295                 300

Glu Asp Arg Phe Thr Tyr Glu Gln Ala Leu Ser Ala Gln Ile Asp Lys
305                 310                 315                 320

Ala Gln Glu Lys Gly Glu Gly Thr Leu Glu Glu Leu Leu Ala Gly Asn
                325                 330                 335

Ser Thr Trp Thr Ile Asn
            340
```

<210> SEQ ID NO 5
<211> LENGTH: 747
<212> TYPE: DNA
<213> ORGANISM: Escherichia coli
<220> FEATURE:
<221> NAME/KEY: CDS
<222> LOCATION: (1)..(747)

<400> SEQUENCE: 5

```
atg gct gat tgg gta aca ggc aaa gtc act aaa gtg cag aac tgg acc      48
Met Ala Asp Trp Val Thr Gly Lys Val Thr Lys Val Gln Asn Trp Thr
1               5                   10                  15
```

```
gac gcc ctg ttt agt ctc acc gtt cac gcc ccc gtg ctt ccg ttt acc      96
Asp Ala Leu Phe Ser Leu Thr Val His Ala Pro Val Leu Pro Phe Thr
         20                  25                  30 gcc ggg caa ttt acc aag ctt ggc ctt gaa atc gac ggc gaa cgc gtc     144
Ala Gly Gln Phe Thr Lys Leu Gly Leu Glu Ile Asp Gly Glu Arg Val
             35                  40                  45 cag cgc gcc tac tcc tat gta aac tcg ccc gat aat ccc gat ctg gag     192
Gln Arg Ala Tyr Ser Tyr Val Asn Ser Pro Asp Asn Pro Asp Leu Glu
 50                  55                  60 ttt tac ctg gtc acc gtc ccc gat ggc aaa tta agc cca cga ctg gcg     240
Phe Tyr Leu Val Thr Val Pro Asp Gly Lys Leu Ser Pro Arg Leu Ala
 65                  70                  75                  80 gca ctg aaa cca ggc gat gaa gtg cag gtg gtt agc gaa gcg gca gga     288
Ala Leu Lys Pro Gly Asp Glu Val Gln Val Val Ser Glu Ala Ala Gly
                     85                  90                  95 ttc ttt gtg ctc gat gaa gtg ccg cac tgc gaa acg cta tgg atg ctg     336
Phe Phe Val Leu Asp Glu Val Pro His Cys Glu Thr Leu Trp Met Leu
                 100                 105                 110 gca acc ggt aca gcg att ggc cct tat tta tcg att ctg caa cta ggt     384
Ala Thr Gly Thr Ala Ile Gly Pro Tyr Leu Ser Ile Leu Gln Leu Gly
             115                 120                 125 aaa gat tta gat cgc ttc aaa aat ctg gtc ctg gtg cac gcc gca cgt     432
Lys Asp Leu Asp Arg Phe Lys Asn Leu Val Leu Val His Ala Ala Arg
130                 135                 140 tat gcc gcc gac tta agc tat ttg cca ctg atg cag gaa ctg gaa aaa     480
Tyr Ala Ala Asp Leu Ser Tyr Leu Pro Leu Met Gln Glu Leu Glu Lys
145                 150                 155                 160 cgc tac gaa gga aaa ctg cgc att cag acg gtg gtc agt cgg gaa acg     528
Arg Tyr Glu Gly Lys Leu Arg Ile Gln Thr Val Val Ser Arg Glu Thr
                 165                 170                 175 gca gcg ggg tcg ctc acc gga cgg ata ccg gca tta att gaa agt ggg     576
Ala Ala Gly Ser Leu Thr Gly Arg Ile Pro Ala Leu Ile Glu Ser Gly
             180                 185                 190 gaa ctg gaa agc acg att ggc ctg ccg atg aat aaa gaa acc agc cat     624
Glu Leu Glu Ser Thr Ile Gly Leu Pro Met Asn Lys Glu Thr Ser His
         195                 200                 205 gtg atg ctg tgc ggc aat cca cag atg gtg cgc gat aca caa cag ttg     672
Val Met Leu Cys Gly Asn Pro Gln Met Val Arg Asp Thr Gln Gln Leu
 210                 215                 220 ctg aaa gag acc cgg cag atg acg aaa cat tta cgt cgc cga ccg ggc     720
Leu Lys Glu Thr Arg Gln Met Thr Lys His Leu Arg Arg Arg Pro Gly
225                 230                 235                 240 cat atg aca gcg gag cat tac tgg taa                                 747
His Met Thr Ala Glu His Tyr Trp
                 245

<210> SEQ ID NO 6
<211> LENGTH: 248
<212> TYPE: PRT
<213> ORGANISM: Escherichia coli

<400> SEQUENCE: 6

Met Ala Asp Trp Val Thr Gly Lys Val Thr Lys Val Gln Asn Trp Thr
 1               5                  10                  15

Asp Ala Leu Phe Ser Leu Thr Val His Ala Pro Val Leu Pro Phe Thr
             20                  25                  30

Ala Gly Gln Phe Thr Lys Leu Gly Leu Glu Ile Asp Gly Glu Arg Val
         35                  40                  45

Gln Arg Ala Tyr Ser Tyr Val Asn Ser Pro Asp Asn Pro Asp Leu Glu
     50                  55                  60
```

```
Phe Tyr Leu Val Thr Val Pro Asp Gly Lys Leu Ser Pro Arg Leu Ala
 65                  70                  75                  80

Ala Leu Lys Pro Gly Asp Glu Val Gln Val Ser Glu Ala Ala Gly
                 85                  90                  95

Phe Phe Val Leu Asp Glu Val Pro His Cys Glu Thr Leu Trp Met Leu
            100                 105                 110

Ala Thr Gly Thr Ala Ile Gly Pro Tyr Leu Ser Ile Leu Gln Leu Gly
                115                 120                 125

Lys Asp Leu Asp Arg Phe Lys Asn Leu Val Leu Val His Ala Ala Arg
130                 135                 140

Tyr Ala Ala Asp Leu Ser Tyr Leu Pro Leu Met Gln Glu Leu Glu Lys
145                 150                 155                 160

Arg Tyr Glu Gly Lys Leu Arg Ile Gln Thr Val Val Ser Arg Glu Thr
                165                 170                 175

Ala Ala Gly Ser Leu Thr Gly Arg Ile Pro Ala Leu Ile Glu Ser Gly
            180                 185                 190

Glu Leu Glu Ser Thr Ile Gly Leu Pro Met Asn Lys Glu Thr Ser His
        195                 200                 205

Val Met Leu Cys Gly Asn Pro Gln Met Val Arg Asp Thr Gln Gln Leu
210                 215                 220

Leu Lys Glu Thr Arg Gln Met Thr Lys His Leu Arg Arg Arg Pro Gly
225                 230                 235                 240

His Met Thr Ala Glu His Tyr Trp
                245

<210> SEQ ID NO 7
<211> LENGTH: 3558
<212> TYPE: DNA
<213> ORGANISM: Chlorobium tepidum
<220> FEATURE:
<221> NAME/KEY: CDS
<222> LOCATION: (1)..(3558)

<400> SEQUENCE: 7 atg acc cgg aca ttc aag aca atg gag ggg aat gaa gct ctt gct cat      48
Met Thr Arg Thr Phe Lys Thr Met Glu Gly Asn Glu Ala Leu Ala His
  1               5                  10                  15 gtc gcc tat cgc act aat gaa gtc atc tcg ata tac ccg att acc ccg      96
Val Ala Tyr Arg Thr Asn Glu Val Ile Ser Ile Tyr Pro Ile Thr Pro
             20                  25                  30 gca tct ccg atg gga gag tac tcc gac gca tgg gcc gct gtc gat gta     144
Ala Ser Pro Met Gly Glu Tyr Ser Asp Ala Trp Ala Ala Val Asp Val
         35                  40                  45 aaa aat atc tgg ggt acc gtg cca ctc gtc aat gag atg cag agc gaa     192
Lys Asn Ile Trp Gly Thr Val Pro Leu Val Asn Glu Met Gln Ser Glu
 50                  55                  60 gcc ggt gcc gcc gcc gcc gtt cac ggc gcg ttg cag acc ggc gcg ctg     240
Ala Gly Ala Ala Ala Ala Val His Gly Ala Leu Gln Thr Gly Ala Leu
 65                  70                  75                  80 acg acc acc ttc acg gcc tct cag ggt ctc tta ctg atg atc ccg aac     288
Thr Thr Thr Phe Thr Ala Ser Gln Gly Leu Leu Leu Met Ile Pro Asn
             85                  90                  95 atg tac aag atc gcc ggt gaa ctg acc ccc tgc gtg att cac gtg tca     336
Met Tyr Lys Ile Ala Gly Glu Leu Thr Pro Cys Val Ile His Val Ser
            100                 105                 110 gcc cgt tcg ctg gcc gcg cag gcg ctc tcg ata ttc tgc gac cac ggt     384
Ala Arg Ser Leu Ala Ala Gln Ala Leu Ser Ile Phe Cys Asp His Gly
            115                 120                 125
```

```
gac gtg atg tcg gtc agg ggc acc ggc ttc gcg ctg ctc gct tcc tgt        432
Asp Val Met Ser Val Arg Gly Thr Gly Phe Ala Leu Leu Ala Ser Cys
    130             135                 140 tcg gta cag gag gta atg gac atg gcg ctg att tcg cag gcc gca acg        480
Ser Val Gln Glu Val Met Asp Met Ala Leu Ile Ser Gln Ala Ala Thr
145                 150                 155                 160 ctc gaa tcg cgc gtg cca ttc ctg cac ttc ttc gac ggc ttc cgc acg        528
Leu Glu Ser Arg Val Pro Phe Leu His Phe Phe Asp Gly Phe Arg Thr
                    165                 170                 175 tcg cac gaa atc tcg aaa atc gag gtg ctc tcg gac gaa cag att cgc        576
Ser His Glu Ile Ser Lys Ile Glu Val Leu Ser Asp Glu Gln Ile Arg
                180                 185                 190 tcg atg atc aac gac gag ctg gtc ttc gca cac cgc atg cgc cgc atg        624
Ser Met Ile Asn Asp Glu Leu Val Phe Ala His Arg Met Arg Arg Met
            195                 200                 205 tcg cct gat gca ccg atc atc cgc ggt acc tcg cag aat ccg gac gtc        672
Ser Pro Asp Ala Pro Ile Ile Arg Gly Thr Ser Gln Asn Pro Asp Val
        210                 215                 220 tat ttc cag gca cgc gag agc gtc aac aaa tat tat gag gcc tgc ccg        720
Tyr Phe Gln Ala Arg Glu Ser Val Asn Lys Tyr Tyr Glu Ala Cys Pro
225                 230                 235                 240 tca atc acc cag aag gcg atg gac cag ttc gcc aaa ctg act ggg cgc        768
Ser Ile Thr Gln Lys Ala Met Asp Gln Phe Ala Lys Leu Thr Gly Arg
                    245                 250                 255 agc tat aaa ctt tac cag tac tac ggc gct ccg gat gcc gac cgt atc        816
Ser Tyr Lys Leu Tyr Gln Tyr Tyr Gly Ala Pro Asp Ala Asp Arg Ile
                260                 265                 270 atc atc atg atg ggg tca ggt gcc gag acc gct ctc gaa act gtc gaa        864
Ile Ile Met Met Gly Ser Gly Ala Glu Thr Ala Leu Glu Thr Val Glu
            275                 280                 285 tac ctc aac aac cac ggc gaa aag gtc ggt ctg gtc aag gta cgc ctt        912
Tyr Leu Asn Asn His Gly Glu Lys Val Gly Leu Val Lys Val Arg Leu
        290                 295                 300 ttc agg cca ttc gac gtt gca acc ttc atc gca tcg cta cca tcg agc        960
Phe Arg Pro Phe Asp Val Ala Thr Phe Ile Ala Ser Leu Pro Ser Ser
305                 310                 315                 320 gtg aag agt atc gcg gtg ctc gac cgt gtc aag gaa cca ggc agc gct       1008
Val Lys Ser Ile Ala Val Leu Asp Arg Val Lys Glu Pro Gly Ser Ala
                    325                 330                 335 ggc gaa ccg ctc tat ctc gat gta gtc aac gcc gta gcc gaa tcg tac       1056
Gly Glu Pro Leu Tyr Leu Asp Val Val Asn Ala Val Ala Glu Ser Tyr
                340                 345                 350 cag gaa ggc aaa tgc gct tcg atg cca agc gtt ttg ggt ggg cgc tat       1104
Gln Glu Gly Lys Cys Ala Ser Met Pro Ser Val Leu Gly Gly Arg Tyr
            355                 360                 365 ggc ctg tcg tcg aag gag ttc act ccg gcg atg gtc aag gcg atc ttc       1152
Gly Leu Ser Ser Lys Glu Phe Thr Pro Ala Met Val Lys Ala Ile Phe
        370                 375                 380 gac aat atg aac gcg gaa tct cca aag aat cac ttc acc gtt ggc atc       1200
Asp Asn Met Asn Ala Glu Ser Pro Lys Asn His Phe Thr Val Gly Ile
385                 390                 395                 400 gac gat gac gta acc aag aag agc ctc gcc tac gac gag acc ttc tcg       1248
Asp Asp Asp Val Thr Lys Lys Ser Leu Ala Tyr Asp Glu Thr Phe Ser
                    405                 410                 415 att gag ccg gac tcg gtc ttc cgc gcc ctc ttc tac ggc ctc ggt tca       1296
Ile Glu Pro Asp Ser Val Phe Arg Ala Leu Phe Tyr Gly Leu Gly Ser
                420                 425                 430 gac ggc acg gtc ggt gca aac aag aac tcg atc aag atc att ggc gaa       1344
Asp Gly Thr Val Gly Ala Asn Lys Asn Ser Ile Lys Ile Ile Gly Glu
            435                 440                 445
```

```
aac acc gac aac tac gcg cag ggc ttc ttc gtc tac gac tcc aag aaa    1392
Asn Thr Asp Asn Tyr Ala Gln Gly Phe Phe Val Tyr Asp Ser Lys Lys
    450                 455                 460 gcc ggt tcg atc acg acc tcg cac ctg cgg ttc ggc ccg gag cag atc    1440
Ala Gly Ser Ile Thr Thr Ser His Leu Arg Phe Gly Pro Glu Gln Ile
465                 470                 475                 480 cgc tcg acc tac ctc atc acc gag gcg cag ttc gtc ggc tgc cac cac    1488
Arg Ser Thr Tyr Leu Ile Thr Glu Ala Gln Phe Val Gly Cys His His
                485                 490                 495 tgg gtc ttt ctc gaa atg atc gac gtt gcc aag aac ctc aag cag ggt    1536
Trp Val Phe Leu Glu Met Ile Asp Val Ala Lys Asn Leu Lys Gln Gly
            500                 505                 510 ggt acg ctg ctc atc aac tcg gcc tat gcg ccg gat gtg gtg tgg agc    1584
Gly Thr Leu Leu Ile Asn Ser Ala Tyr Ala Pro Asp Val Val Trp Ser
        515                 520                 525 aag ctc ccg cgt ccg gtg cag cag cac ttg atc gac aag cag gcg aag    1632
Lys Leu Pro Arg Pro Val Gln Gln His Leu Ile Asp Lys Gln Ala Lys
    530                 535                 540 ctc tac acc atc gat gcc tac aag gtc gcc cac gaa agc ggc atg ggt    1680
Leu Tyr Thr Ile Asp Ala Tyr Lys Val Ala His Glu Ser Gly Met Gly
545                 550                 555                 560 cag cgc atc aac act atc atg cag gcc tgt ttc ttc gcc att tcg ggc    1728
Gln Arg Ile Asn Thr Ile Met Gln Ala Cys Phe Phe Ala Ile Ser Gly
                565                 570                 575 gtg ctg ccg cgt gaa gag gca atc gaa aag atc aag gac gcg atc cgc    1776
Val Leu Pro Arg Glu Glu Ala Ile Glu Lys Ile Lys Asp Ala Ile Arg
            580                 585                 590 cac acc tac ggc aaa aag ggc gat gag gtc gtt cag cag aac atc aag    1824
His Thr Tyr Gly Lys Lys Gly Asp Glu Val Val Gln Gln Asn Ile Lys
        595                 600                 605 gca gtt gac aac acg ctt gcc aac ctg cat gaa gtg aaa atc ggc gct    1872
Ala Val Asp Asn Thr Leu Ala Asn Leu His Glu Val Lys Ile Gly Ala
    610                 615                 620 gtg gca gac agc acc aag gag ctg cgc tcg ccc atc gtt ggc gac gcg    1920
Val Ala Asp Ser Thr Lys Glu Leu Arg Ser Pro Ile Val Gly Asp Ala
625                 630                 635                 640 cca gag ttc gtc tgt aac gtg ctg gca aag att att gcc ggc gag ggc    1968
Pro Glu Phe Val Cys Asn Val Leu Ala Lys Ile Ile Ala Gly Glu Gly
                645                 650                 655 gac tcg att ccg gtc agc aag ctg cct gcc gat gga acc tat ccg ctc    2016
Asp Ser Ile Pro Val Ser Lys Leu Pro Ala Asp Gly Thr Tyr Pro Leu
            660                 665                 670 ggc acc acg aag ttc gag aaa cgc aac ctc gcg cag gag att ccg gtc    2064
Gly Thr Thr Lys Phe Glu Lys Arg Asn Leu Ala Gln Glu Ile Pro Val
        675                 680                 685 tgg gct ccg gag ctg tgc atc gag tgt ggc aag tgc tcg atg gtc tgc    2112
Trp Ala Pro Glu Leu Cys Ile Glu Cys Gly Lys Cys Ser Met Val Cys
    690                 695                 700 ccg cac gct gcc atc cgc atc aag gtt tac gag ccg aag cac ctc gaa    2160
Pro His Ala Ala Ile Arg Ile Lys Val Tyr Glu Pro Lys His Leu Glu
705                 710                 715                 720 aac gcc ccg gca acc ttc aag agc ctc gat gcg aaa gca aaa aac tgg    2208
Asn Ala Pro Ala Thr Phe Lys Ser Leu Asp Ala Lys Ala Lys Asn Trp
                725                 730                 735 gag ggc atg cgc tat acg gtt cag att gca ccg gaa gat tgt acc ggc    2256
Glu Gly Met Arg Tyr Thr Val Gln Ile Ala Pro Glu Asp Cys Thr Gly
            740                 745                 750 tgc caa ctc tgc gtc aac gcc tgc ccc gca aga gac aag cag gtt gaa    2304
Cys Gln Leu Cys Val Asn Ala Cys Pro Ala Arg Asp Lys Gln Val Glu
        755                 760                 765
```

```
ggc cgc aaa gcg ctc aac atg cac gag cag gct ccg ctg cgc gaa acc    2352
Gly Arg Lys Ala Leu Asn Met His Glu Gln Ala Pro Leu Arg Glu Thr
        770                 775                 780 gaa tct gcc tgc tgg agc ttc ttc atc aat ctc ccg gaa ttc gac cgc    2400
Glu Ser Ala Cys Trp Ser Phe Phe Ile Asn Leu Pro Glu Phe Asp Arg
785                 790                 795                 800 aac aag atc aac cag cgc ctc atc aaa gag cag cag ctt cag cag cca    2448
Asn Lys Ile Asn Gln Arg Leu Ile Lys Glu Gln Gln Leu Gln Gln Pro
                805                 810                 815 ctc ttc gag ttc tcg ggc gca tgc tcg ggc tgc ggc gaa acg cca tac    2496
Leu Phe Glu Phe Ser Gly Ala Cys Ser Gly Cys Gly Glu Thr Pro Tyr
                820                 825                 830 gtc aag ctg atg act cag ctc ttc ggt gat cgc ctc gtt atc ggc aac    2544
Val Lys Leu Met Thr Gln Leu Phe Gly Asp Arg Leu Val Ile Gly Asn
                835                 840                 845 gcc acc ggc tgc tcg tcg atc tac ggc ggc aac ctg ccg acc acg ccg    2592
Ala Thr Gly Cys Ser Ser Ile Tyr Gly Gly Asn Leu Pro Thr Thr Pro
                850                 855                 860 tat gca gcc aac ccg cag ggc ctt ggg cca acg tgg tcg aac tcg ctt    2640
Tyr Ala Ala Asn Pro Gln Gly Leu Gly Pro Thr Trp Ser Asn Ser Leu
865                 870                 875                 880 ttc gag gac acg gca gag ttc gcg ctt ggt ttc cgg ata tcg atc gac    2688
Phe Glu Asp Thr Ala Glu Phe Ala Leu Gly Phe Arg Ile Ser Ile Asp
                885                 890                 895 aag cag cag caa ttt gcc aaa gag ctg gtc aaa aag ctc gct ggt gac    2736
Lys Gln Gln Gln Phe Ala Lys Glu Leu Val Lys Lys Leu Ala Gly Asp
                900                 905                 910 atc ggt gaa aac ctt gcc acc gcc att ctc aac gcc acg cag aac agt    2784
Ile Gly Glu Asn Leu Ala Thr Ala Ile Leu Asn Ala Thr Gln Asn Ser
                915                 920                 925 gaa ccg gag att ttc gag cag cgt gag cgc gtg gcc gtg ctg aag gat    2832
Glu Pro Glu Ile Phe Glu Gln Arg Glu Arg Val Ala Val Leu Lys Asp
        930                 935                 940 aag ctc cag cag atg aaa tcc gac gat gcc aag aac ctg ctt gct gtg    2880
Lys Leu Gln Gln Met Lys Ser Asp Asp Ala Lys Asn Leu Leu Ala Val
945                 950                 955                 960 gct gac atg ctg gtc aag aag agc gtg tgg gct gtc ggc ggc gac ggc    2928
Ala Asp Met Leu Val Lys Lys Ser Val Trp Ala Val Gly Gly Asp Gly
                965                 970                 975 tgg gcc tac gat atc ggt tac ggg ggt ctc gac cac gtc acc gca tcg    2976
Trp Ala Tyr Asp Ile Gly Tyr Gly Gly Leu Asp His Val Thr Ala Ser
                980                 985                 990 ggc aag aac gtc aac atg ctc gtg  ctc gac acc gag gtc  tat tcc aat   3024
Gly Lys Asn Val Asn Met Leu Val  Leu Asp Thr Glu Val  Tyr Ser Asn
                995                  1000                1005 acc ggc  ggt cag gcc tcc aag  gct acg ccg aaa gcc  gcg atc gcc      3069
Thr Gly  Gly Gln Ala Ser Lys  Ala Thr Pro Lys Ala  Ala Ile Ala
    1010                1015                1020 aag ttt  gcc gct gcg ggg cgc  atc gct acc aag aaa  gac ctt ggt      3114
Lys Phe  Ala Ala Ala Gly Arg  Ile Ala Thr Lys Lys  Asp Leu Gly
    1025                1030                1035 ctg atc  tcg atg agc tac ggc  aat gcc tat gtg gcc  agt gtt gca      3159
Leu Ile  Ser Met Ser Tyr Gly  Asn Ala Tyr Val Ala  Ser Val Ala
    1040                1045                1050 ctt ggc  gca cgt gac gag cag  aca ctc aga gct ttc  atc gaa gcc      3204
Leu Gly  Ala Arg Asp Glu Gln  Thr Leu Arg Ala Phe  Ile Glu Ala
    1055                1060                1065 gag gcg  tac gat ggc ccg tcg  att atc atc gcc tac  tcg cac tgc      3249
Glu Ala  Tyr Asp Gly Pro Ser  Ile Ile Ile Ala Tyr  Ser His Cys
    1070                1075                1080
```

| | | | | | | | | | | |
|---|---|---|---|---|---|---|---|---|---|---|
| att | gca | cac | ggc | ttt | gac | ttg | tct | atg | ggt | ctg | gag | cac | cag | aaa | 3294 |
| Ile | Ala | His | Gly | Phe | Asp | Leu | Ser | Met | Gly | Leu | Glu | His | Gln | Lys |
| 1085 | | | | 1090 | | | | | 1095 | | | | | |

| gca | gcg | gtc | gat | tcc | ggc | cac | tgg | ctg | ctg | tat | cgc | tac | aat | ccc | 3339 |
|---|---|---|---|---|---|---|---|---|---|---|---|---|---|---|---|
| Ala | Ala | Val | Asp | Ser | Gly | His | Trp | Leu | Leu | Tyr | Arg | Tyr | Asn | Pro |
| 1100 | | | | | 1105 | | | | | 1110 | | | | |

| gac | aga | ctc | aag | gag | gga | ctg | aat | ccg | ctg | cag | ctc | gac | tcc | aaa | 3384 |
|---|---|---|---|---|---|---|---|---|---|---|---|---|---|---|---|
| Asp | Arg | Leu | Lys | Glu | Gly | Leu | Asn | Pro | Leu | Gln | Leu | Asp | Ser | Lys |
| 1115 | | | | | 1120 | | | | | 1125 | | | | |

| aag | ccg | aaa | atg | ccg | gtc | gcg | gag | ttc | ctg | aac | atg | gag | aac | cgc | 3429 |
|---|---|---|---|---|---|---|---|---|---|---|---|---|---|---|---|
| Lys | Pro | Lys | Met | Pro | Val | Ala | Glu | Phe | Leu | Asn | Met | Glu | Asn | Arg |
| 1130 | | | | | 1135 | | | | | 1140 | | | | |

| ttc | aga | ata | ctg | aag | aag | acc | cac | ccc | gat | ctg | gcc | aag | aag | tac | 3474 |
|---|---|---|---|---|---|---|---|---|---|---|---|---|---|---|---|
| Phe | Arg | Ile | Leu | Lys | Lys | Thr | His | Pro | Asp | Leu | Ala | Lys | Lys | Tyr |
| 1145 | | | | | 1150 | | | | | 1155 | | | | |

| ttc | gag | gca | atc | cag | cac | gag | gtc | aat | gcc | cgc | tgg | gca | cac | tac | 3519 |
|---|---|---|---|---|---|---|---|---|---|---|---|---|---|---|---|
| Phe | Glu | Ala | Ile | Gln | His | Glu | Val | Asn | Ala | Arg | Trp | Ala | His | Tyr |
| 1160 | | | | | 1165 | | | | | 1170 | | | | |

| gaa | cac | ctc | gcc | aac | cgt | tcg | att | gaa | ggc | gaa | gca | taa | | | 3558 |
|---|---|---|---|---|---|---|---|---|---|---|---|---|---|---|---|
| Glu | His | Leu | Ala | Asn | Arg | Ser | Ile | Glu | Gly | Glu | Ala | | | |
| 1175 | | | | | 1180 | | | | | 1185 | | | | |

<210> SEQ ID NO 8
<211> LENGTH: 1185
<212> TYPE: PRT
<213> ORGANISM: Chlorobium tepidum

<400> SEQUENCE: 8

```
Met Thr Arg Thr Phe Lys Thr Met Glu Gly Asn Glu Ala Leu Ala His
1               5                   10                  15

Val Ala Tyr Arg Thr Asn Glu Val Ile Ser Ile Tyr Pro Ile Thr Pro
            20                  25                  30

Ala Ser Pro Met Gly Glu Tyr Ser Asp Ala Trp Ala Ala Val Asp Val
        35                  40                  45

Lys Asn Ile Trp Gly Thr Val Pro Leu Val Asn Glu Met Gln Ser Glu
    50                  55                  60

Ala Gly Ala Ala Ala Val His Gly Ala Leu Gln Thr Gly Ala Leu
65                  70                  75                  80

Thr Thr Thr Phe Thr Ala Ser Gln Gly Leu Leu Leu Met Ile Pro Asn
                85                  90                  95

Met Tyr Lys Ile Ala Gly Glu Leu Thr Pro Cys Val Ile His Val Ser
            100                 105                 110

Ala Arg Ser Leu Ala Ala Gln Ala Leu Ser Ile Phe Cys Asp His Gly
        115                 120                 125

Asp Val Met Ser Val Arg Gly Thr Gly Phe Ala Leu Leu Ala Ser Cys
    130                 135                 140

Ser Val Gln Glu Val Met Asp Met Ala Leu Ile Ser Gln Ala Ala Thr
145                 150                 155                 160

Leu Glu Ser Arg Val Pro Phe Leu His Phe Phe Asp Gly Phe Arg Thr
                165                 170                 175

Ser His Glu Ile Ser Lys Ile Glu Val Leu Ser Asp Gly Gln Ile Arg
            180                 185                 190

Ser Met Ile Asn Asp Glu Leu Val Phe Ala His Arg Met Arg Arg Met
        195                 200                 205

Ser Pro Asp Ala Pro Ile Ile Arg Gly Thr Ser Gln Asn Pro Asp Val
    210                 215                 220

Tyr Phe Gln Ala Arg Glu Ser Val Asn Lys Tyr Tyr Glu Ala Cys Pro
225                 230                 235                 240
```

```
Ser Ile Thr Gln Lys Ala Met Asp Gln Phe Ala Lys Leu Thr Gly Arg
            245                 250                 255
Ser Tyr Lys Leu Tyr Gln Tyr Gly Ala Pro Asp Ala Asp Arg Ile
        260                 265                 270
Ile Ile Met Met Gly Ser Gly Ala Glu Thr Ala Leu Glu Thr Val Glu
            275                 280                 285
Tyr Leu Asn Asn His Gly Glu Lys Val Gly Leu Val Lys Val Arg Leu
        290                 295                 300
Phe Arg Pro Phe Asp Val Ala Thr Phe Ile Ala Ser Leu Pro Ser Ser
305                 310                 315                 320
Val Lys Ser Ile Ala Val Leu Asp Arg Val Lys Glu Pro Gly Ser Ala
            325                 330                 335
Gly Glu Pro Leu Tyr Leu Asp Val Val Asn Ala Val Ala Glu Ser Tyr
            340                 345                 350
Gln Glu Gly Lys Cys Ala Ser Met Pro Ser Val Leu Gly Gly Arg Tyr
            355                 360                 365
Gly Leu Ser Ser Lys Glu Phe Thr Pro Ala Met Val Lys Ala Ile Phe
        370                 375                 380
Asp Asn Met Asn Ala Glu Ser Pro Lys Asn His Phe Thr Val Gly Ile
385                 390                 395                 400
Asp Asp Asp Val Thr Lys Lys Ser Leu Ala Tyr Asp Glu Thr Phe Ser
                405                 410                 415
Ile Glu Pro Asp Ser Val Phe Arg Ala Leu Phe Tyr Gly Leu Gly Ser
            420                 425                 430
Asp Gly Thr Val Gly Ala Asn Lys Asn Ser Ile Lys Ile Ile Gly Glu
        435                 440                 445
Asn Thr Asp Asn Tyr Ala Gln Gly Phe Phe Val Tyr Asp Ser Lys Lys
        450                 455                 460
Ala Gly Ser Ile Thr Thr Ser His Leu Arg Phe Gly Pro Glu Gln Ile
465                 470                 475                 480
Arg Ser Thr Tyr Leu Ile Thr Glu Ala Gln Phe Val Gly Cys His His
                485                 490                 495
Trp Val Phe Leu Glu Met Ile Asp Val Ala Lys Asn Leu Lys Gln Gly
            500                 505                 510
Gly Thr Leu Leu Ile Asn Ser Ala Tyr Ala Pro Asp Val Val Trp Ser
        515                 520                 525
Lys Leu Pro Arg Pro Val Gln Gln His Leu Ile Asp Lys Gln Ala Lys
        530                 535                 540
Leu Tyr Thr Ile Asp Ala Tyr Lys Val Ala His Glu Ser Gly Met Gly
545                 550                 555                 560
Gln Arg Ile Asn Thr Ile Met Gln Ala Cys Phe Phe Ala Ile Ser Gly
                565                 570                 575
Val Leu Pro Arg Glu Glu Ala Ile Glu Lys Ile Lys Asp Ala Ile Arg
            580                 585                 590
His Thr Tyr Gly Lys Lys Gly Asp Glu Val Val Gln Gln Asn Ile Lys
        595                 600                 605
Ala Val Asp Asn Thr Leu Ala Asn Leu His Glu Val Lys Ile Gly Ala
        610                 615                 620
Val Ala Asp Ser Thr Lys Glu Leu Arg Ser Pro Ile Val Gly Asp Ala
625                 630                 635                 640
Pro Glu Phe Val Cys Asn Val Leu Ala Lys Ile Ile Ala Gly Glu Gly
                645                 650                 655
Asp Ser Ile Pro Val Ser Lys Leu Pro Ala Asp Gly Thr Tyr Pro Leu
```

```
                    660             665             670
Gly Thr Thr Lys Phe Glu Lys Arg Asn Leu Ala Gln Glu Ile Pro Val
                675             680             685

Trp Ala Pro Glu Leu Cys Ile Glu Cys Gly Lys Cys Ser Met Val Cys
        690             695             700

Pro His Ala Ala Ile Arg Ile Lys Val Tyr Glu Pro Lys His Leu Glu
705             710             715             720

Asn Ala Pro Ala Thr Phe Lys Ser Leu Asp Ala Lys Ala Lys Asn Trp
                725             730             735

Glu Gly Met Arg Tyr Thr Val Gln Ile Ala Pro Glu Asp Cys Thr Gly
            740             745             750

Cys Gln Leu Cys Val Asn Ala Cys Pro Ala Arg Asp Lys Gln Val Glu
        755             760             765

Gly Arg Lys Ala Leu Asn Met His Glu Gln Ala Pro Leu Arg Glu Thr
    770             775             780

Glu Ser Ala Cys Trp Ser Phe Phe Ile Asn Leu Pro Glu Phe Asp Arg
785             790             795             800

Asn Lys Ile Asn Gln Arg Leu Ile Lys Glu Gln Leu Gln Gln Pro
                805             810             815

Leu Phe Glu Phe Ser Gly Ala Cys Ser Gly Cys Gly Glu Thr Pro Tyr
            820             825             830

Val Lys Leu Met Thr Gln Leu Phe Gly Asp Arg Leu Val Ile Gly Asn
                835             840             845

Ala Thr Gly Cys Ser Ser Ile Tyr Gly Gly Asn Leu Pro Thr Thr Pro
            850             855             860

Tyr Ala Ala Asn Pro Gln Gly Leu Gly Pro Thr Trp Ser Asn Ser Leu
865             870             875             880

Phe Glu Asp Thr Ala Glu Phe Ala Leu Gly Phe Arg Ile Ser Ile Asp
                885             890             895

Lys Gln Gln Gln Phe Ala Lys Glu Leu Val Lys Leu Ala Gly Asp
            900             905             910

Ile Gly Glu Asn Leu Ala Thr Ala Ile Leu Asn Ala Thr Gln Asn Ser
                915             920             925

Glu Pro Glu Ile Phe Glu Gln Arg Glu Arg Val Ala Val Leu Lys Asp
    930             935             940

Lys Leu Gln Gln Met Lys Ser Asp Asp Ala Lys Asn Leu Leu Ala Val
945             950             955             960

Ala Asp Met Leu Val Lys Lys Ser Val Trp Ala Val Gly Gly Asp Gly
            965             970             975

Trp Ala Tyr Asp Ile Gly Tyr Gly Gly Leu Asp His Val Thr Ala Ser
            980             985             990

Gly Lys Asn Val Asn Met Leu Val  Leu Asp Thr Glu Val  Tyr Ser Asn
            995         1000            1005

Thr Gly  Gly Gln Ala Ser Lys  Ala Thr Pro Lys Ala  Ala Ile Ala
    1010            1015            1020

Lys Phe  Ala Ala Ala Gly Arg  Ile Ala Thr Lys Lys  Asp Leu Gly
    1025            1030            1035

Leu Ile  Ser Met Ser Tyr Gly  Asn Ala Tyr Val Ala  Ser Val Ala
    1040            1045            1050

Leu Gly  Ala Arg Asp Glu Gln  Thr Leu Arg Ala Phe  Ile Glu Ala
    1055            1060            1065

Glu Ala  Tyr Asp Gly Pro Ser  Ile Ile Ile Ala Tyr  Ser His Cys
    1070            1075            1080
```

-continued

```
Ile Ala His Gly Phe Asp Leu Ser Met Gly Leu Glu His Gln Lys
    1085                1090                1095

Ala Ala Val Asp Ser Gly His Trp Leu Leu Tyr Arg Tyr Asn Pro
    1100                1105                1110

Asp Arg Leu Lys Glu Gly Leu Asn Pro Leu Gln Leu Asp Ser Lys
    1115                1120                1125

Lys Pro Lys Met Pro Val Ala Glu Phe Leu Asn Met Glu Asn Arg
    1130                1135                1140

Phe Arg Ile Leu Lys Lys Thr His Pro Asp Leu Ala Lys Lys Tyr
    1145                1150                1155

Phe Glu Ala Ile Gln His Glu Val Asn Ala Arg Trp Ala His Tyr
    1160                1165                1170

Glu His Leu Ala Asn Arg Ser Ile Glu Gly Glu Ala
    1175                1180                1185
```

<210> SEQ ID NO 9
<211> LENGTH: 336
<212> TYPE: DNA
<213> ORGANISM: Escherichia coli
<220> FEATURE:
<221> NAME/KEY: CDS
<222> LOCATION: (1)..(336)

<400> SEQUENCE: 9

```
atg cca aag att gtt att ttg cct cat cag gat ctc tgc cct gat ggc    48
Met Pro Lys Ile Val Ile Leu Pro His Gln Asp Leu Cys Pro Asp Gly
1               5                   10                  15 gct gtt ctg gaa gct aat agc ggt gaa acc att ctc gac gca gct ctg    96
Ala Val Leu Glu Ala Asn Ser Gly Glu Thr Ile Leu Asp Ala Ala Leu
            20                  25                  30 cgt aac ggt atc gag att gaa cac gcc tgt gaa aaa tcc tgt gct tgc   144
Arg Asn Gly Ile Glu Ile Glu His Ala Cys Glu Lys Ser Cys Ala Cys
        35                  40                  45 acc acc tgc cac tgc atc gtt cgt gaa ggt ttt gac tca ctg ccg gaa   192
Thr Thr Cys His Cys Ile Val Arg Glu Gly Phe Asp Ser Leu Pro Glu
    50                  55                  60 agc tca gag cag gaa gac gac atg ctg gac aaa gcc tgg gga ctg gag   240
Ser Ser Glu Gln Glu Asp Asp Met Leu Asp Lys Ala Trp Gly Leu Glu
65                  70                  75                  80 ccg gaa agc cgt tta agc tgc cag gcg cgc gtt acc gac gaa gat tta   288
Pro Glu Ser Arg Leu Ser Cys Gln Ala Arg Val Thr Asp Glu Asp Leu
                85                  90                  95 gta gtc gaa atc ccg cgt tac act atc aac cat gcg cgt gag cat taa   336
Val Val Glu Ile Pro Arg Tyr Thr Ile Asn His Ala Arg Glu His
            100                 105                 110
```

<210> SEQ ID NO 10
<211> LENGTH: 111
<212> TYPE: PRT
<213> ORGANISM: Escherichia coli

<400> SEQUENCE: 10

```
Met Pro Lys Ile Val Ile Leu Pro His Gln Asp Leu Cys Pro Asp Gly
1               5                   10                  15

Ala Val Leu Glu Ala Asn Ser Gly Glu Thr Ile Leu Asp Ala Ala Leu
            20                  25                  30

Arg Asn Gly Ile Glu Ile Glu His Ala Cys Glu Lys Ser Cys Ala Cys
        35                  40                  45

Thr Thr Cys His Cys Ile Val Arg Glu Gly Phe Asp Ser Leu Pro Glu
    50                  55                  60
```

```
Ser Ser Glu Gln Glu Asp Asp Met Leu Asp Lys Ala Trp Gly Leu Glu
 65                  70                  75                  80

Pro Glu Ser Arg Leu Ser Cys Gln Ala Arg Val Thr Asp Glu Asp Leu
                 85                  90                  95

Val Val Glu Ile Pro Arg Tyr Thr Ile Asn His Ala Arg Glu His
            100                 105                 110

<210> SEQ ID NO 11
<211> LENGTH: 261
<212> TYPE: DNA
<213> ORGANISM: Escherichia coli
<220> FEATURE:
<221> NAME/KEY: CDS
<222> LOCATION: (1)..(261)

<400> SEQUENCE: 11 atg gcg ttg tta atc act aaa aaa tgc atc aat tgt gat atg tgt gaa      48
Met Ala Leu Leu Ile Thr Lys Lys Cys Ile Asn Cys Asp Met Cys Glu
 1               5                  10                  15 ccc gaa tgc ccg aat gag gcg att tca atg gga gat cat atc tac gag      96
Pro Glu Cys Pro Asn Glu Ala Ile Ser Met Gly Asp His Ile Tyr Glu
                 20                  25                  30 att aac agc gat aag tgt acc gaa tgc gta ggg cac tac gag aca cca     144
Ile Asn Ser Asp Lys Cys Thr Glu Cys Val Gly His Tyr Glu Thr Pro
            35                  40                  45 acc tgc cag aag gtg tgc ccg atc ccc aat act att gtg aaa gat ccg     192
Thr Cys Gln Lys Val Cys Pro Ile Pro Asn Thr Ile Val Lys Asp Pro
     50                  55                  60 gcg cat gtc gag aca gaa gaa cag ttg tgg gat aaa ttt gtg ctg atg     240
Ala His Val Glu Thr Glu Glu Gln Leu Trp Asp Lys Phe Val Leu Met
 65                  70                  75                  80 cac cac gcg gat aaa att taa                                         261
His His Ala Asp Lys Ile
                 85

<210> SEQ ID NO 12
<211> LENGTH: 86
<212> TYPE: PRT
<213> ORGANISM: Escherichia coli

<400> SEQUENCE: 12

Met Ala Leu Leu Ile Thr Lys Lys Cys Ile Asn Cys Asp Met Cys Glu
 1               5                  10                  15

Pro Glu Cys Pro Asn Glu Ala Ile Ser Met Gly Asp His Ile Tyr Glu
                 20                  25                  30

Ile Asn Ser Asp Lys Cys Thr Glu Cys Val Gly His Tyr Glu Thr Pro
            35                  40                  45

Thr Cys Gln Lys Val Cys Pro Ile Pro Asn Thr Ile Val Lys Asp Pro
     50                  55                  60

Ala His Val Glu Thr Glu Glu Gln Leu Trp Asp Lys Phe Val Leu Met
 65                  70                  75                  80

His His Ala Asp Lys Ile
                 85

<210> SEQ ID NO 13
<211> LENGTH: 531
<212> TYPE: DNA
<213> ORGANISM: Escherichia coli
<220> FEATURE:
<221> NAME/KEY: CDS
<222> LOCATION: (1)..(531)

<400> SEQUENCE: 13
```

```
atg gct atc act ggc atc ttt ttc ggc agc gac acc ggt aat acc gaa    48
Met Ala Ile Thr Gly Ile Phe Phe Gly Ser Asp Thr Gly Asn Thr Glu
1               5                   10                  15 aat atc gca aaa atg att caa aaa cag ctt ggt aaa gac gtt gcc gat    96
Asn Ile Ala Lys Met Ile Gln Lys Gln Leu Gly Lys Asp Val Ala Asp
            20                  25                  30 gtc cat gac att gca aaa agc agc aaa gaa gat ctg gaa gct tat gac   144
Val His Asp Ile Ala Lys Ser Ser Lys Glu Asp Leu Glu Ala Tyr Asp
        35                  40                  45 att ctg ctg ctg ggc atc cca acc tgg tat tac ggc gaa gcg cag tgt   192
Ile Leu Leu Leu Gly Ile Pro Thr Trp Tyr Tyr Gly Glu Ala Gln Cys
50                  55                  60 gac tgg gat gac ttc ttc ccg act ctc gaa gag att gat ttc aac ggc   240
Asp Trp Asp Asp Phe Phe Pro Thr Leu Glu Glu Ile Asp Phe Asn Gly
65                  70                  75                  80 aaa ctg gtt gcg ctg ttt ggt tgt ggt gac cag gaa gat tac gcc gaa   288
Lys Leu Val Ala Leu Phe Gly Cys Gly Asp Gln Glu Asp Tyr Ala Glu
                85                  90                  95 tat ttc tgc gac gca ttg ggc acc atc cgc gac atc att gaa ccg cgc   336
Tyr Phe Cys Asp Ala Leu Gly Thr Ile Arg Asp Ile Ile Glu Pro Arg
            100                 105                 110 ggt gca acc atc gtt ggt cac tgg cca act gcg ggc tat cat ttc gaa   384
Gly Ala Thr Ile Val Gly His Trp Pro Thr Ala Gly Tyr His Phe Glu
        115                 120                 125 gca tca aaa ggt ctg gca gat gac gac cac ttt gtc ggt ctg gct atc   432
Ala Ser Lys Gly Leu Ala Asp Asp Asp His Phe Val Gly Leu Ala Ile
130                 135                 140 gac gaa gac cgt cag ccg gaa ctg acc gct gaa cgt gta gaa aaa tgg   480
Asp Glu Asp Arg Gln Pro Glu Leu Thr Ala Glu Arg Val Glu Lys Trp
145                 150                 155                 160 gtt aaa cag att tct gaa gag ttg cat ctc gac gaa att ctc aat gcc   528
Val Lys Gln Ile Ser Glu Glu Leu His Leu Asp Glu Ile Leu Asn Ala
                165                 170                 175 tga                                                               531
```

<210> SEQ ID NO 14
<211> LENGTH: 176
<212> TYPE: PRT
<213> ORGANISM: Escherichia coli

<400> SEQUENCE: 14

```
Met Ala Ile Thr Gly Ile Phe Phe Gly Ser Asp Thr Gly Asn Thr Glu
1               5                   10                  15

Asn Ile Ala Lys Met Ile Gln Lys Gln Leu Gly Lys Asp Val Ala Asp
            20                  25                  30

Val His Asp Ile Ala Lys Ser Ser Lys Glu Asp Leu Glu Ala Tyr Asp
        35                  40                  45

Ile Leu Leu Leu Gly Ile Pro Thr Trp Tyr Tyr Gly Glu Ala Gln Cys
50                  55                  60

Asp Trp Asp Asp Phe Phe Pro Thr Leu Glu Glu Ile Asp Phe Asn Gly
65                  70                  75                  80

Lys Leu Val Ala Leu Phe Gly Cys Gly Asp Gln Glu Asp Tyr Ala Glu
                85                  90                  95

Tyr Phe Cys Asp Ala Leu Gly Thr Ile Arg Asp Ile Ile Glu Pro Arg
            100                 105                 110

Gly Ala Thr Ile Val Gly His Trp Pro Thr Ala Gly Tyr His Phe Glu
        115                 120                 125

Ala Ser Lys Gly Leu Ala Asp Asp Asp His Phe Val Gly Leu Ala Ile
```

```
                130                 135                 140
Asp Glu Asp Arg Gln Pro Glu Leu Thr Ala Glu Arg Val Glu Lys Trp
145                 150                 155                 160

Val Lys Gln Ile Ser Glu Glu Leu His Leu Asp Glu Ile Leu Asn Ala
                165                 170                 175

<210> SEQ ID NO 15
<211> LENGTH: 522
<212> TYPE: DNA
<213> ORGANISM: Escherichia coli
<220> FEATURE:
<221> NAME/KEY: CDS
<222> LOCATION: (1)..(522)

<400> SEQUENCE: 15 atg aat atg ggt ctt ttt tac ggt tcc agc acc tgt tac acc gaa atg    48
Met Asn Met Gly Leu Phe Tyr Gly Ser Ser Thr Cys Tyr Thr Glu Met
1               5                   10                  15 gcg gca gaa aaa atc cgc gat att atc ggc cca gaa ctg gtg acc tta    96
Ala Ala Glu Lys Ile Arg Asp Ile Ile Gly Pro Glu Leu Val Thr Leu
                20                  25                  30 cat aac ctc aag gac gac tcc ccg aaa tta atg gag cag tac gat gtg   144
His Asn Leu Lys Asp Asp Ser Pro Lys Leu Met Glu Gln Tyr Asp Val
            35                  40                  45 ctc att ctg ggt atc ccg acc tgg gat ttt ggt gaa atc cag gaa gac   192
Leu Ile Leu Gly Ile Pro Thr Trp Asp Phe Gly Glu Ile Gln Glu Asp
        50                  55                  60 tgg gaa gcc gtc tgg gat cag ctc gac gac ctg aac ctt gaa ggt aaa   240
Trp Glu Ala Val Trp Asp Gln Leu Asp Asp Leu Asn Leu Glu Gly Lys
65                  70                  75                  80 att gtt gcg ctg tat ggg ctt ggc gat caa ctg gga tac ggc gag tgg   288
Ile Val Ala Leu Tyr Gly Leu Gly Asp Gln Leu Gly Tyr Gly Glu Trp
                85                  90                  95 ttc ctc gat gcg ctc ggt atg ctg cat gac aaa ctc tcg acc aaa ggc   336
Phe Leu Asp Ala Leu Gly Met Leu His Asp Lys Leu Ser Thr Lys Gly
            100                 105                 110 gtg aag ttc gtc ggc tac tgg cca acg gaa gga tat gaa ttt acc agc   384
Val Lys Phe Val Gly Tyr Trp Pro Thr Glu Gly Tyr Glu Phe Thr Ser
        115                 120                 125 ccg aaa ccg gtg att gct gac ggg caa ctg ttc gtg ggt ctg gcg ctg   432
Pro Lys Pro Val Ile Ala Asp Gly Gln Leu Phe Val Gly Leu Ala Leu
    130                 135                 140 gat gaa act aac cag tat gac ctt agc gac gag cgt att cag agc tgg   480
Asp Glu Thr Asn Gln Tyr Asp Leu Ser Asp Glu Arg Ile Gln Ser Trp
145                 150                 155                 160 tgc gag caa atc ctc aac gaa atg gca gag cat tac gcc tga           522
Cys Glu Gln Ile Leu Asn Glu Met Ala Glu His Tyr Ala
                165                 170

<210> SEQ ID NO 16
<211> LENGTH: 173
<212> TYPE: PRT
<213> ORGANISM: Escherichia coli

<400> SEQUENCE: 16

Met Asn Met Gly Leu Phe Tyr Gly Ser Ser Thr Cys Tyr Thr Glu Met
1               5                   10                  15

Ala Ala Glu Lys Ile Arg Asp Ile Ile Gly Pro Glu Leu Val Thr Leu
                20                  25                  30

His Asn Leu Lys Asp Asp Ser Pro Lys Leu Met Glu Gln Tyr Asp Val
            35                  40                  45
```

```
Leu Ile Leu Gly Ile Pro Thr Trp Asp Phe Gly Glu Ile Gln Glu Asp
         50                  55                  60

Trp Glu Ala Val Trp Asp Gln Leu Asp Asp Leu Asn Leu Glu Gly Lys
 65                  70                  75                  80

Ile Val Ala Leu Tyr Gly Leu Gly Asp Gln Leu Gly Tyr Gly Glu Trp
                 85                  90                  95

Phe Leu Asp Ala Leu Gly Met Leu His Asp Lys Leu Ser Thr Lys Gly
            100                 105                 110

Val Lys Phe Val Gly Tyr Trp Pro Thr Glu Gly Tyr Glu Phe Thr Ser
        115                 120                 125

Pro Lys Pro Val Ile Ala Asp Gly Gln Leu Phe Val Gly Leu Ala Leu
    130                 135                 140

Asp Glu Thr Asn Gln Tyr Asp Leu Ser Asp Glu Arg Ile Gln Ser Trp
145                 150                 155                 160

Cys Glu Gln Ile Leu Asn Glu Met Ala Glu His Tyr Ala
                165                 170
```

```
<210> SEQ ID NO 17
<211> LENGTH: 189
<212> TYPE: DNA
<213> ORGANISM: Chlorobium tepidum
<220> FEATURE:
<221> NAME/KEY: CDS
<222> LOCATION: (1)..(189)

<400> SEQUENCE: 17 atg gca ctg tat atc acc gaa gaa tgc acc tac tgc ggt gct tgc gaa      48
Met Ala Leu Tyr Ile Thr Glu Glu Cys Thr Tyr Cys Gly Ala Cys Glu
 1               5                  10                  15 ccc gaa tgc ccg acc aac gct atc tcc gct ggc agc gag atc tac gtt      96
Pro Glu Cys Pro Thr Asn Ala Ile Ser Ala Gly Ser Glu Ile Tyr Val
             20                  25                  30 atc gat gcc gca tcc tgc aac gag tgc gcc ggt ttt gct gac tct cct     144
Ile Asp Ala Ala Ser Cys Asn Glu Cys Ala Gly Phe Ala Asp Ser Pro
         35                  40                  45 gct tgc gtt gct gtc tgc ccg gca gag tgc atc gtt cag ggc tga         189
Ala Cys Val Ala Val Cys Pro Ala Glu Cys Ile Val Gln Gly
     50                  55                  60
```

```
<210> SEQ ID NO 18
<211> LENGTH: 62
<212> TYPE: PRT
<213> ORGANISM: Chlorobium tepidum

<400> SEQUENCE: 18

Met Ala Leu Tyr Ile Thr Glu Glu Cys Thr Tyr Cys Gly Ala Cys Glu
 1               5                  10                  15

Pro Glu Cys Pro Thr Asn Ala Ile Ser Ala Gly Ser Glu Ile Tyr Val
             20                  25                  30

Ile Asp Ala Ala Ser Cys Asn Glu Cys Ala Gly Phe Ala Asp Ser Pro
         35                  40                  45

Ala Cys Val Ala Val Cys Pro Ala Glu Cys Ile Val Gln Gly
     50                  55                  60
```

```
<210> SEQ ID NO 19
<211> LENGTH: 189
<212> TYPE: DNA
<213> ORGANISM: Chlorobium tepidum
<220> FEATURE:
<221> NAME/KEY: CDS
<222> LOCATION: (1)..(189)
```

<400> SEQUENCE: 19

```
atg gca cac cgt att acc gat gaa tgc acc tac tgt gca gcc tgc gag      48
Met Ala His Arg Ile Thr Asp Glu Cys Thr Tyr Cys Ala Ala Cys Glu
1               5                  10                  15 ccg gaa tgt ccg gtc agc gcg atc tcc gct ggc gac tct att tac gtg      96
Pro Glu Cys Pro Val Ser Ala Ile Ser Ala Gly Asp Ser Ile Tyr Val
            20                  25                  30 atc gac gag aat gta tgc gtg gat tgt atc ggc tat cac gac gag cct     144
Ile Asp Glu Asn Val Cys Val Asp Cys Ile Gly Tyr His Asp Glu Pro
        35                  40                  45 gcc tgt gtg gcc gtc tgc ccg gtg gac tgc att atc aag gta tag         189
Ala Cys Val Ala Val Cys Pro Val Asp Cys Ile Ile Lys Val
    50                  55                  60
```

<210> SEQ ID NO 20
<211> LENGTH: 62
<212> TYPE: PRT
<213> ORGANISM: Chlorobium tepidum

<400> SEQUENCE: 20

```
Met Ala His Arg Ile Thr Asp Glu Cys Thr Tyr Cys Ala Ala Cys Glu
1               5                  10                  15

Pro Glu Cys Pro Val Ser Ala Ile Ser Ala Gly Asp Ser Ile Tyr Val
            20                  25                  30

Ile Asp Glu Asn Val Cys Val Asp Cys Ile Gly Tyr His Asp Glu Pro
        35                  40                  45

Ala Cys Val Ala Val Cys Pro Val Asp Cys Ile Ile Lys Val
    50                  55                  60
```

<210> SEQ ID NO 21
<211> LENGTH: 52
<212> TYPE: DNA
<213> ORGANISM: Artificial
<220> FEATURE:
<223> OTHER INFORMATION: primer

<400> SEQUENCE: 21
tttggatcct aaggaggaat gacccatgag tgacaccgta atcttaaaca ac      52

<210> SEQ ID NO 22
<211> LENGTH: 36
<212> TYPE: DNA
<213> ORGANISM: Artificial
<220> FEATURE:
<223> OTHER INFORMATION: primer

<400> SEQUENCE: 22
aaaggatcct cgtgatcagt tgatcgtcca ggtgct      36

<210> SEQ ID NO 23
<211> LENGTH: 51
<212> TYPE: DNA
<213> ORGANISM: Artificial
<220> FEATURE:
<223> OTHER INFORMATION: primer

<400> SEQUENCE: 23
ttttctagat aaggaggaat gacgtatgac ccggacattc aagacaatgg a      51

<210> SEQ ID NO 24
<211> LENGTH: 39
<212> TYPE: DNA
<213> ORGANISM: Artificial
<220> FEATURE:

-continued

<223> OTHER INFORMATION: primer

<400> SEQUENCE: 24
aaatctagat tcagcttatg cttcgccttc aatcgaacg                              39

<210> SEQ ID NO 25
<211> LENGTH: 53
<212> TYPE: DNA
<213> ORGANISM: Artificial
<220> FEATURE:
<223> OTHER INFORMATION: primer

<400> SEQUENCE: 25
tttcccgggt aaggaggaat gaaccatggc acaccgtatt accgatgaat gca             53

<210> SEQ ID NO 26
<211> LENGTH: 40
<212> TYPE: DNA
<213> ORGANISM: Artificial
<220> FEATURE:
<223> OTHER INFORMATION: primer

<400> SEQUENCE: 26
aaacccgggt cgacggtggc tataccttga taatgcagtc                             40

<210> SEQ ID NO 27
<211> LENGTH: 43
<212> TYPE: DNA
<213> ORGANISM: Artificial
<220> FEATURE:
<223> OTHER INFORMATION: primer

<400> SEQUENCE: 27
atgaaactcg ccgtttatag cacaatgaag cctgcttttt tat                         43

<210> SEQ ID NO 28
<211> LENGTH: 43
<212> TYPE: DNA
<213> ORGANISM: Artificial
<220> FEATURE:
<223> OTHER INFORMATION: primer

<400> SEQUENCE: 28
ttaaaccagt tcgttcgggc aggttcgctc aagttagtat aaa                         43

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
atgaattttt caatatcgcc                                                   20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
aattacagtt tctgactcag                                                   20

<210> SEQ ID NO 31

```
<211> LENGTH: 344
<212> TYPE: DNA
<213> ORGANISM: Escherichia coli

<400> SEQUENCE: 31
aagctttacg cgaacgagcc atgacattgc tgacgactct ggcagtggca gatgacataa       60
aactggtcga ctggttacaa caacgcctgg ggcttttaga gcaacgagac acggcaatgt      120
tgcaccgttt gctgcatgat attgaaaaaa atatcaccaa ataaaaaacg ccttagtaag      180 tattttcag cttttcattc tgactgcaac gggcaatatg tctctgtgtg gattaaaaaa       240
agagtgtctg atagcagctt ctgaactggt tacctgccgt gagtaaatta aaattttatt      300
gacttaggtc actaaatact ttaaccaata taggcgactc taga                       344

<210> SEQ ID NO 32
<211> LENGTH: 35
<212> TYPE: DNA
<213> ORGANISM: Artificial
<220> FEATURE:
<223> OTHER INFORMATION: primer

<400> SEQUENCE: 32
ctctctggcg gtaccctgat tgatttgatc gattg                                  35

<210> SEQ ID NO 33
<211> LENGTH: 33
<212> TYPE: DNA
<213> ORGANISM: Artificial
<220> FEATURE:
<223> OTHER INFORMATION: primer

<400> SEQUENCE: 33
gagagacggt accttaccag taatgctccg ctg                                    33

<210> SEQ ID NO 34
<211> LENGTH: 35
<212> TYPE: DNA
<213> ORGANISM: Artificial
<220> FEATURE:
<223> OTHER INFORMATION: primer

<400> SEQUENCE: 34
ctctctggcg aattcttcaa taagtttcaa gaggt                                  35

<210> SEQ ID NO 35
<211> LENGTH: 36
<212> TYPE: DNA
<213> ORGANISM: Artificial
<220> FEATURE:
<223> OTHER INFORMATION: primer

<400> SEQUENCE: 35
agagaggccg aattctcagg cattgagaat ttcgtc                                 36

<210> SEQ ID NO 36
<211> LENGTH: 35
<212> TYPE: DNA
<213> ORGANISM: Artificial
<220> FEATURE:
<223> OTHER INFORMATION: primer

<400> SEQUENCE: 36
ctctctggcg aattcagaat cgagaagctt acgtt                                  35

<210> SEQ ID NO 37
```

```
<211> LENGTH: 35
<212> TYPE: DNA
<213> ORGANISM: Artificial
<220> FEATURE:
<223> OTHER INFORMATION: primer

<400> SEQUENCE: 37
ctctctggcg aattctcagg cgtaatgctc tgcca                              35

<210> SEQ ID NO 38
<211> LENGTH: 30
<212> TYPE: DNA
<213> ORGANISM: Artificial
<220> FEATURE:
<223> OTHER INFORMATION: primer

<400> SEQUENCE: 38
gcgcgaattc gggcgatgat gttgacgcca                                    30

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
gcgcgaattc gtcccatact aacctctgtt                                    30

<210> SEQ ID NO 40
<211> LENGTH: 36
<212> TYPE: DNA
<213> ORGANISM: Artificial
<220> FEATURE:
<223> OTHER INFORMATION: primer

<400> SEQUENCE: 40
ctctctggcg aattctgttg ttttgagagt ttcctt                             36

<210> SEQ ID NO 41
<211> LENGTH: 34
<212> TYPE: DNA
<213> ORGANISM: Artificial
<220> FEATURE:
<223> OTHER INFORMATION: primer

<400> SEQUENCE: 41
agagaggccg aattcttaaa ttttatccgc gtgg                               34

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42
cccaagcttc tgcccctgac actaagaca                                     29

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
```

-continued

```
cgaggtaacg ttcaagacct                                              20

<210> SEQ ID NO 44
<211> LENGTH: 40
<212> TYPE: DNA
<213> ORGANISM: Artificial
<220> FEATURE:
<223> OTHER INFORMATION: primer

<400> SEQUENCE: 44
aggtcttgaa cgttacctcg atccataacg ggcagggcgc                         40

<210> SEQ ID NO 45
<211> LENGTH: 29
<212> TYPE: DNA
<213> ORGANISM: Artificial
<220> FEATURE:
<223> OTHER INFORMATION: primer

<400> SEQUENCE: 45
gggtctagac cactttgtca gtttcgatt                                     29

<210> SEQ ID NO 46
<211> LENGTH: 4556
<212> TYPE: DNA
<213> ORGANISM: Pantoea ananatis
<220> FEATURE:
<221> NAME/KEY: CDS
<222> LOCATION: (2)..(121)
<220> FEATURE:
<221> NAME/KEY: CDS
<222> LOCATION: (322)..(3129)
<220> FEATURE:
<221> NAME/KEY: CDS
<222> LOCATION: (3145)..(4368)
<220> FEATURE:
<221> NAME/KEY: CDS
<222> LOCATION: (4437)..(4556)

<400> SEQUENCE: 46 t gca ttc agc gtt ttc cgc tgt cac agc atc atg aac tgt gta agt gtt    49
  Ala Phe Ser Val Phe Arg Cys His Ser Ile Met Asn Cys Val Ser Val
  1               5                  10                 15 tgt cct aaa ggg cta aac ccg acg cgc gct atc ggc cac att aag tcg      97
Cys Pro Lys Gly Leu Asn Pro Thr Arg Ala Ile Gly His Ile Lys Ser
            20                  25                  30 atg ctg ctg caa cgc agc gcg tag ttataccacc gggaacctca ggttcccggt    151
Met Leu Leu Gln Arg Ser Ala
        35 attttacgga agcctctgta aacgcggtcc caaccacgtt tacaaaggtt cccttacggg    211 ccgggcgcgc gctgcgcaca gtgctcgtat cgctgaactc actacggcaa accgcgaaag    271 cggcaacaaa tgaaacctca aaaagcata acattgctta aggatcaca atg cag        327
                                                      Met Gln
                                                          40 aac agc gcg atg aag ccc tgg ctg gac tcc tcc tgg ctg gcc ggc gcg      375
Asn Ser Ala Met Lys Pro Trp Leu Asp Ser Ser Trp Leu Ala Gly Ala
        45                  50                  55 aat cag tct tac ata gag caa ctc tat gag gat ttc ctg acc gat cct      423
Asn Gln Ser Tyr Ile Glu Gln Leu Tyr Glu Asp Phe Leu Thr Asp Pro
    60                  65                  70 gac tct gtg gat gca gtg tgg cgc tcg atg ttc caa cag tta cca ggc      471
Asp Ser Val Asp Ala Val Trp Arg Ser Met Phe Gln Gln Leu Pro Gly
75                  80                  85 acg gga gtg aaa cct gag cag ttc cac tcc gca act cgc gaa tat ttc      519
Thr Gly Val Lys Pro Glu Gln Phe His Ser Ala Thr Arg Glu Tyr Phe
            90                  95                 100
```

```
                90                  95                 100                 105
cgt cgc ctg gcg aaa gac gca tct cgt tac acc tcc tca gtt acc gat           567
Arg Arg Leu Ala Lys Asp Ala Ser Arg Tyr Thr Ser Ser Val Thr Asp
                    110                 115                 120 ccg gca acc aac tcc aaa caa gtg aaa gtg ctg cag ctg att aac gcg           615
Pro Ala Thr Asn Ser Lys Gln Val Lys Val Leu Gln Leu Ile Asn Ala
                125                 130                 135 ttt cgt ttc cgc gga cat cag gaa gca aat ctc gat ccg ctt ggc ctg           663
Phe Arg Phe Arg Gly His Gln Glu Ala Asn Leu Asp Pro Leu Gly Leu
            140                 145                 150 tgg aaa cag gac cgc gtt gcc gat ctc gat cct gcc ttt cac gat ctg           711
Trp Lys Gln Asp Arg Val Ala Asp Leu Asp Pro Ala Phe His Asp Leu
        155                 160                 165 acc gac gcc gat ttt cag gaa agc ttt aac gta ggt tct ttt gcc att           759
Thr Asp Ala Asp Phe Gln Glu Ser Phe Asn Val Gly Ser Phe Ala Ile
170                 175                 180                 185 ggc aaa gaa acc atg aag ctg gcc gat ctg ttc gac gcg ctg aag cag           807
Gly Lys Glu Thr Met Lys Leu Ala Asp Leu Phe Asp Ala Leu Lys Gln
                190                 195                 200 acc tac tgt ggc tcg att ggt gca gag tat atg cac atc aat aac acc           855
Thr Tyr Cys Gly Ser Ile Gly Ala Glu Tyr Met His Ile Asn Asn Thr
            205                 210                 215 gaa gag aaa cgc tgg atc cag cag cgt atc gaa tcc ggt gcg agc cag           903
Glu Glu Lys Arg Trp Ile Gln Gln Arg Ile Glu Ser Gly Ala Ser Gln
        220                 225                 230 acg tca ttc agt ggc gaa gag aaa aaa ggt ttc ctg aaa gag ctg acc           951
Thr Ser Phe Ser Gly Glu Glu Lys Lys Gly Phe Leu Lys Glu Leu Thr
    235                 240                 245 gcg gca gaa ggg ctg gaa aaa tat ctg ggc gcg aaa ttc ccg ggt gca           999
Ala Ala Glu Gly Leu Glu Lys Tyr Leu Gly Ala Lys Phe Pro Gly Ala
250                 255                 260                 265 aaa cgt ttc tcg ctg gaa ggc ggt gat gcg ctg gtg ccg atg ctg cgc          1047
Lys Arg Phe Ser Leu Glu Gly Gly Asp Ala Leu Val Pro Met Leu Arg
                270                 275                 280 gag atg att cgt cat gcg ggc aaa agc ggc aca cgt gaa gtg gta ctg          1095
Glu Met Ile Arg His Ala Gly Lys Ser Gly Thr Arg Glu Val Val Leu
            285                 290                 295 ggg atg gcg cac cgt ggc cgt ctt aac gta ctg att aac gta ctg ggt          1143
Gly Met Ala His Arg Gly Arg Leu Asn Val Leu Ile Asn Val Leu Gly
        300                 305                 310 aaa aag cca cag gat ctg ttc gac gaa ttc tcc ggt aaa cac aaa gag          1191
Lys Lys Pro Gln Asp Leu Phe Asp Glu Phe Ser Gly Lys His Lys Glu
    315                 320                 325 cat ctg ggc acc ggt gat gtg aag tat cac atg ggc ttc tct tcg gat          1239
His Leu Gly Thr Gly Asp Val Lys Tyr His Met Gly Phe Ser Ser Asp
330                 335                 340                 345 att gaa acc gaa ggt ggt ctg gtg cat ctg gcg ctg gcg ttt aac ccg          1287
Ile Glu Thr Glu Gly Gly Leu Val His Leu Ala Leu Ala Phe Asn Pro
                350                 355                 360 tct cac ctg gaa att gtc agc ccg gtg gtc atg gga tcg gta cgt gca          1335
Ser His Leu Glu Ile Val Ser Pro Val Val Met Gly Ser Val Arg Ala
            365                 370                 375 cgt ctc gat cgt ctg gcc gaa ccg gtc agc aat aaa gtg ttg cct atc          1383
Arg Leu Asp Arg Leu Ala Glu Pro Val Ser Asn Lys Val Leu Pro Ile
        380                 385                 390 acc att cac ggt gat gcg gcg gtg att ggt cag ggc gtg gtt cag gaa          1431
Thr Ile His Gly Asp Ala Ala Val Ile Gly Gln Gly Val Val Gln Glu
    395                 400                 405 acc ctg aac atg tct cag gcg cgc ggc tac gaa gtg ggc ggc acg gta          1479
Thr Leu Asn Met Ser Gln Ala Arg Gly Tyr Glu Val Gly Gly Thr Val
```

```
                410                 415                 420                 425
cgt atc gtc att aac aac cag gtt ggt ttt acc acc tcc aac ccg aaa       1527
Arg Ile Val Ile Asn Asn Gln Val Gly Phe Thr Thr Ser Asn Pro Lys
                    430                 435                 440 gat gcg cgt tca acc ccg tac tgt act gac atc ggc aag atg gtg ctg       1575
Asp Ala Arg Ser Thr Pro Tyr Cys Thr Asp Ile Gly Lys Met Val Leu
                445                 450                 455 gca ccg att ttc cac gtc aat gct gac gat ccg gaa gcg gtg gcc ttt       1623
Ala Pro Ile Phe His Val Asn Ala Asp Asp Pro Glu Ala Val Ala Phe
            460                 465                 470 gtt acc cgc ctg gcg ctg gac tat cgc aac acc ttc aaa cgc gat gtg       1671
Val Thr Arg Leu Ala Leu Asp Tyr Arg Asn Thr Phe Lys Arg Asp Val
        475                 480                 485 ttt atc gat ctg gtg tgc tat cgc cgt cat ggt cac aac gag gcg gat       1719
Phe Ile Asp Leu Val Cys Tyr Arg Arg His Gly His Asn Glu Ala Asp
490                 495                 500                 505 gag cca agt gct acc cag ccg ttg atg tac cag aaa atc aaa aag cat       1767
Glu Pro Ser Ala Thr Gln Pro Leu Met Tyr Gln Lys Ile Lys Lys His
                    510                 515                 520 ccg acg ccg cgt aaa att tac gcc gat cgt ctg gaa ggc gaa ggt gtc       1815
Pro Thr Pro Arg Lys Ile Tyr Ala Asp Arg Leu Glu Gly Glu Gly Val
                525                 530                 535 gcg tcg cag gaa gat gcc acc gag atg gtg aac ctg tac cgc gat gcg       1863
Ala Ser Gln Glu Asp Ala Thr Glu Met Val Asn Leu Tyr Arg Asp Ala
            540                 545                 550 ctc gat gcg ggc gaa tgc gtg gtg ccg gaa tgg cgt ccg atg agc ctg       1911
Leu Asp Ala Gly Glu Cys Val Val Pro Glu Trp Arg Pro Met Ser Leu
        555                 560                 565 cac tcc ttc acg tgg tcg cct tat ctg aac cac gaa tgg gat gag cct       1959
His Ser Phe Thr Trp Ser Pro Tyr Leu Asn His Glu Trp Asp Glu Pro
570                 575                 580                 585 tat ccg gca cag gtt gac atg aaa cgc ctg aag gaa ctg gca ttg cgt       2007
Tyr Pro Ala Gln Val Asp Met Lys Arg Leu Lys Glu Leu Ala Leu Arg
                    590                 595                 600 atc agc cag gtc cct gag cag att gaa gtg cag tcg cgc gtg gcc aag       2055
Ile Ser Gln Val Pro Glu Gln Ile Glu Val Gln Ser Arg Val Ala Lys
                605                 610                 615 atc tat aac gat cgc aag ctg atg gcc gaa ggc gag aaa gcg ttc gac       2103
Ile Tyr Asn Asp Arg Lys Leu Met Ala Glu Gly Glu Lys Ala Phe Asp
            620                 625                 630 tgg ggc ggt gcc gag aat ctg gcg tac gcc acg ctg gtg gat gaa ggt       2151
Trp Gly Gly Ala Glu Asn Leu Ala Tyr Ala Thr Leu Val Asp Glu Gly
        635                 640                 645 att ccg gtt cgc ctc tcg ggt gaa gac tcc ggt cgt gga acc ttc ttc       2199
Ile Pro Val Arg Leu Ser Gly Glu Asp Ser Gly Arg Gly Thr Phe Phe
650                 655                 660                 665 cat cgc cac gcg gtc gtg cac aac cag gct aac ggt tca acc tat acg       2247
His Arg His Ala Val Val His Asn Gln Ala Asn Gly Ser Thr Tyr Thr
                    670                 675                 680 ccg ctg cac cat att cat aac agc cag ggc gag ttc aaa gtc tgg gat       2295
Pro Leu His His Ile His Asn Ser Gln Gly Glu Phe Lys Val Trp Asp
                685                 690                 695 tcg gtg ctg tct gaa gaa gcg gtg ctg gcg ttt gaa tac ggt tac gcc       2343
Ser Val Leu Ser Glu Glu Ala Val Leu Ala Phe Glu Tyr Gly Tyr Ala
            700                 705                 710 acg gct gag ccg cgc gtg ctg acc atc tgg gaa gcg cag ttt ggt gac       2391
Thr Ala Glu Pro Arg Val Leu Thr Ile Trp Glu Ala Gln Phe Gly Asp
        715                 720                 725 ttt gcc aac ggt gct cag gtg gtg att gac cag ttc atc agc tct ggc       2439
Phe Ala Asn Gly Ala Gln Val Val Ile Asp Gln Phe Ile Ser Ser Gly
```

```
                                        -continued
  730                 735                 740                 745 gaa cag aag tgg ggc cgt atg tgt ggc ctg gtg atg ttg ctg ccg cat    2487
Glu Gln Lys Trp Gly Arg Met Cys Gly Leu Val Met Leu Leu Pro His
            750                 755                 760 ggc tac gaa ggt cag gga ccg gaa cac tcc tct gcc cgt ctg gaa cgc    2535
Gly Tyr Glu Gly Gln Gly Pro Glu His Ser Ser Ala Arg Leu Glu Arg
        765                 770                 775 tat ctg caa ctt tgc gcc gag cag aac atg cag gtt tgc gtc ccg tcg    2583
Tyr Leu Gln Leu Cys Ala Glu Gln Asn Met Gln Val Cys Val Pro Ser
    780                 785                 790 acg ccg gct cag gtg tat cac atg ctg cgc cgt cag gcg ctg cgc ggg    2631
Thr Pro Ala Gln Val Tyr His Met Leu Arg Arg Gln Ala Leu Arg Gly
795                 800                 805 atg cgc cgt ccg ctg gtg gtg atg tcg ccg aag tcg ctg tta cgc cat    2679
Met Arg Arg Pro Leu Val Val Met Ser Pro Lys Ser Leu Leu Arg His
810                 815                 820                 825 cca ctg gcg atc tcg tcg ctg gat gaa ctg gca aac ggc agt ttc cag    2727
Pro Leu Ala Ile Ser Ser Leu Asp Glu Leu Ala Asn Gly Ser Phe Gln
            830                 835                 840 ccg gcc att ggt gag atc gac gat ctg gat ccg cag ggc gtg aaa cgc    2775
Pro Ala Ile Gly Glu Ile Asp Asp Leu Asp Pro Gln Gly Val Lys Arg
        845                 850                 855 gtc gtg ctg tgc tcc ggt aag gtt tac tac gat ctg ctg gaa cag cgt    2823
Val Val Leu Cys Ser Gly Lys Val Tyr Tyr Asp Leu Leu Glu Gln Arg
    860                 865                 870 cgt aaa gac gag aaa acc gat gtt gcc atc gtg cgc atc gaa cag ctt    2871
Arg Lys Asp Glu Lys Thr Asp Val Ala Ile Val Arg Ile Glu Gln Leu
875                 880                 885 tac ccg ttc ccg cat cag gcg gta cag gaa gca ttg aaa gcc tat tct    2919
Tyr Pro Phe Pro His Gln Ala Val Gln Glu Ala Leu Lys Ala Tyr Ser
890                 895                 900                 905 cac gta cag gac ttt gtc tgg tgc cag gaa gag cct ctg aac cag ggc    2967
His Val Gln Asp Phe Val Trp Cys Gln Glu Glu Pro Leu Asn Gln Gly
            910                 915                 920 gcc tgg tac tgt agc cag cat cat ttc cgt gat gtc gtg ccg ttt ggt    3015
Ala Trp Tyr Cys Ser Gln His His Phe Arg Asp Val Val Pro Phe Gly
        925                 930                 935 gcc acc ctg cgt tat gca ggt cgc ccg gca tcg gct tct ccg gcc gtg    3063
Ala Thr Leu Arg Tyr Ala Gly Arg Pro Ala Ser Ala Ser Pro Ala Val
    940                 945                 950 ggt tat atg tcc gta cac caa caa cag cag caa gac ctg gtt aat gac    3111
Gly Tyr Met Ser Val His Gln Gln Gln Gln Gln Asp Leu Val Asn Asp
955                 960                 965 gca ctg aac gtc aat taa ttaaaaggaa agata atg agt agc gta gat att    3162
Ala Leu Asn Val Asn               Met Ser Ser Val Asp Ile
970                               975                 980 ctc gtt ccc gac ctg cct gaa tcg gtt gca gat gcc aca gta gca acc    3210
Leu Val Pro Asp Leu Pro Glu Ser Val Ala Asp Ala Thr Val Ala Thr
            985                 990                 995 tgg cac aag aaa cca ggc gat gca gtc agc cgc gat gaa gtc atc        3255
Trp His Lys Lys Pro Gly Asp Ala Val Ser Arg Asp Glu Val Ile
        1000                1005                1010 gtc gaa att gaa act gac aaa gtc gtg ctg gaa gtg ccg gca tct        3300
Val Glu Ile Glu Thr Asp Lys Val Val Leu Glu Val Pro Ala Ser
    1015                1020                1025 gcc gat ggc gtg ctg gaa gcc gtg ctg gaa gac gaa ggg gca acc        3345
Ala Asp Gly Val Leu Glu Ala Val Leu Glu Asp Glu Gly Ala Thr
1030                1035                1040 gtt acg tcc cgc cag atc ctg ggt cgc ctg aaa gaa ggc aac agt        3390
Val Thr Ser Arg Gln Ile Leu Gly Arg Leu Lys Glu Gly Asn Ser
```

-continued

| | | | | | | | | | | | | | |
|---|---|---|---|---|---|---|---|---|---|---|---|---|---|
| | | 1045 | | | | 1050 | | | | | 1055 | | |
| gcg | ggt | aaa | gaa | agc | agt | gcc | aaa | gcg | gaa | agc | aat | gac | acc | acg | 3435 |
| Ala | Gly | Lys | Glu | Ser | Ser | Ala | Lys | Ala | Glu | Ser | Asn | Asp | Thr | Thr | |
| | 1060 | | | | | 1065 | | | | | 1070 | | | |
| cca | gcc | cag | cgt | cag | aca | gcg | tcg | ctt | gaa | gaa | gag | agc | agc | gat | 3480 |
| Pro | Ala | Gln | Arg | Gln | Thr | Ala | Ser | Leu | Glu | Glu | Glu | Ser | Ser | Asp | |
| | 1075 | | | | | 1080 | | | | | 1085 | | | |
| gcg | ctc | agc | ccg | gcg | atc | cgt | cgc | ctg | att | gcg | gag | cat | aat | ctt | 3525 |
| Ala | Leu | Ser | Pro | Ala | Ile | Arg | Arg | Leu | Ile | Ala | Glu | His | Asn | Leu | |
| | 1090 | | | | | 1095 | | | | | 1100 | | | |
| gac | gct | gcg | cag | atc | aaa | ggc | acc | ggc | gta | ggc | gga | cgt | tta | acg | 3570 |
| Asp | Ala | Ala | Gln | Ile | Lys | Gly | Thr | Gly | Val | Gly | Gly | Arg | Leu | Thr | |
| | 1105 | | | | | 1110 | | | | | 1115 | | | |
| cgt | gaa | gac | gtt | gaa | aaa | cat | ctg | gcg | aac | aaa | ccg | cag | gct | gag | 3615 |
| Arg | Glu | Asp | Val | Glu | Lys | His | Leu | Ala | Asn | Lys | Pro | Gln | Ala | Glu | |
| | 1120 | | | | | 1125 | | | | | 1130 | | | |
| aaa | gcc | gcc | gcg | cca | gcg | gcg | ggt | gca | gca | acg | gct | cag | cag | cct | 3660 |
| Lys | Ala | Ala | Ala | Pro | Ala | Ala | Gly | Ala | Ala | Thr | Ala | Gln | Gln | Pro | |
| | 1135 | | | | | 1140 | | | | | 1145 | | | |
| gtt | gcc | aac | cgc | agc | gaa | aaa | cgt | gtt | ccg | atg | acg | cgt | tta | cgt | 3705 |
| Val | Ala | Asn | Arg | Ser | Glu | Lys | Arg | Val | Pro | Met | Thr | Arg | Leu | Arg | |
| | 1150 | | | | | 1155 | | | | | 1160 | | | |
| aag | cgc | gtc | gcg | gag | cgt | ctg | ctg | gaa | gcc | aag | aac | agc | acc | gcc | 3750 |
| Lys | Arg | Val | Ala | Glu | Arg | Leu | Leu | Glu | Ala | Lys | Asn | Ser | Thr | Ala | |
| | 1165 | | | | | 1170 | | | | | 1175 | | | |
| atg | ttg | acg | acc | ttc | aac | gaa | atc | aac | atg | aag | ccg | att | atg | gat | 3795 |
| Met | Leu | Thr | Thr | Phe | Asn | Glu | Ile | Asn | Met | Lys | Pro | Ile | Met | Asp | |
| | 1180 | | | | | 1185 | | | | | 1190 | | | |
| ctg | cgt | aag | cag | tac | ggc | gat | gcg | ttc | gag | aag | cgt | cac | ggt | gtg | 3840 |
| Leu | Arg | Lys | Gln | Tyr | Gly | Asp | Ala | Phe | Glu | Lys | Arg | His | Gly | Val | |
| | 1195 | | | | | 1200 | | | | | 1205 | | | |
| cgt | ctg | ggc | ttt | atg | tct | ttc | tac | atc | aag | gcc | gtg | gtc | gaa | gcg | 3885 |
| Arg | Leu | Gly | Phe | Met | Ser | Phe | Tyr | Ile | Lys | Ala | Val | Val | Glu | Ala | |
| | 1210 | | | | | 1215 | | | | | 1220 | | | |
| ctg | aag | cgt | tat | cca | gaa | gtc | aac | gcc | tct | atc | gat | ggc | gaa | gac | 3930 |
| Leu | Lys | Arg | Tyr | Pro | Glu | Val | Asn | Ala | Ser | Ile | Asp | Gly | Glu | Asp | |
| | 1225 | | | | | 1230 | | | | | 1235 | | | |
| gtg | gtg | tac | cac | aac | tat | ttc | gat | gtg | agt | att | gcc | gtc | tct | acg | 3975 |
| Val | Val | Tyr | His | Asn | Tyr | Phe | Asp | Val | Ser | Ile | Ala | Val | Ser | Thr | |
| | 1240 | | | | | 1245 | | | | | 1250 | | | |
| cca | cgc | gga | ctg | gtg | acg | cct | gtc | ctg | cgt | gac | gtt | gat | gcg | ctg | 4020 |
| Pro | Arg | Gly | Leu | Val | Thr | Pro | Val | Leu | Arg | Asp | Val | Asp | Ala | Leu | |
| | 1255 | | | | | 1260 | | | | | 1265 | | | |
| agc | atg | gct | gac | atc | gag | aag | aaa | att | aaa | gaa | ctg | gca | gtg | aaa | 4065 |
| Ser | Met | Ala | Asp | Ile | Glu | Lys | Lys | Ile | Lys | Glu | Leu | Ala | Val | Lys | |
| | 1270 | | | | | 1275 | | | | | 1280 | | | |
| ggc | cgt | gac | ggc | aag | ctg | acg | gtt | gac | gat | ctg | acg | ggc | ggt | aac | 4110 |
| Gly | Arg | Asp | Gly | Lys | Leu | Thr | Val | Asp | Asp | Leu | Thr | Gly | Gly | Asn | |
| | 1285 | | | | | 1290 | | | | | 1295 | | | |
| ttt | acc | atc | acc | aac | ggt | ggt | gtg | ttc | ggt | tcg | ctg | atg | tct | acg | 4155 |
| Phe | Thr | Ile | Thr | Asn | Gly | Gly | Val | Phe | Gly | Ser | Leu | Met | Ser | Thr | |
| | 1300 | | | | | 1305 | | | | | 1310 | | | |
| cca | atc | atc | aac | ccg | cca | cag | agc | gcg | att | ctg | ggc | atg | cac | gcc | 4200 |
| Pro | Ile | Ile | Asn | Pro | Pro | Gln | Ser | Ala | Ile | Leu | Gly | Met | His | Ala | |
| | 1315 | | | | | 1320 | | | | | 1325 | | | |
| att | aaa | gat | cgt | cct | atg | gcg | gtc | aat | ggt | cag | gtt | gtg | atc | ctg | 4245 |
| Ile | Lys | Asp | Arg | Pro | Met | Ala | Val | Asn | Gly | Gln | Val | Val | Ile | Leu | |
| | 1330 | | | | | 1335 | | | | | 1340 | | | |
| cca | atg | atg | tac | ctg | gct | ctc | tcc | tac | gat | cac | cgt | tta | atc | gat | 4290 |
| Pro | Met | Met | Tyr | Leu | Ala | Leu | Ser | Tyr | Asp | His | Arg | Leu | Ile | Asp | |

-continued

```
                       1345                1350                1355
ggt cgt gaa tct gtc ggc tat ctg gtc gcg gtt aaa gag atg ctg      4335
Gly Arg Glu Ser Val Gly Tyr Leu Val Ala Val Lys Glu Met Leu
            1360                1365                1370 gaa gat ccg gcg cgt ctg ctg ctg gat gtc tga ttcatcactg           4378
Glu Asp Pro Ala Arg Leu Leu Leu Asp Val
            1375                1380 ggcacgcgtt gcgtgcccaa tctcaatact cttttcagat ctgaatggat agaacatc  4436 atg aac tta cac gaa tac cag gct aaa cag ctg ttt gca cgg tat      4481
Met Asn Leu His Glu Tyr Gln Ala Lys Gln Leu Phe Ala Arg Tyr
            1385                1390                1395 ggc atg cca gca ccg acc ggc tac gcc tgt act aca cca cgt gaa      4526
Gly Met Pro Ala Pro Thr Gly Tyr Ala Cys Thr Thr Pro Arg Glu
            1400                1405                1410 gca gaa gaa gcg gca tcg aaa atc ggt gca                          4556
Ala Glu Glu Ala Ala Ser Lys Ile Gly Ala
            1415                1420
```

<210> SEQ ID NO 47
<211> LENGTH: 39
<212> TYPE: PRT
<213> ORGANISM: Pantoea ananatis

<400> SEQUENCE: 47

Ala Phe Ser Val Phe Arg Cys His Ser Ile Met Asn Cys Val Ser Val
1               5                   10                  15

Cys Pro Lys Gly Leu Asn Pro Thr Arg Ala Ile Gly His Ile Lys Ser
            20                  25                  30

Met Leu Leu Gln Arg Ser Ala
        35

<210> SEQ ID NO 48
<211> LENGTH: 935
<212> TYPE: PRT
<213> ORGANISM: Pantoea ananatis

<400> SEQUENCE: 48

Met Gln Asn Ser Ala Met Lys Pro Trp Leu Asp Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn

```
                   165                 170                 175
Asn Thr Glu Glu Lys Arg Trp Ile Gln Gln Arg Ile Glu Ser Gly Ala
                180                 185                 190

Ser Gln Thr Ser Phe Ser Gly Glu Glu Lys Lys Gly Phe Leu Lys Glu
            195                 200                 205

Leu Thr Ala Ala Glu Gly Leu Glu Lys Tyr Leu Gly Ala Lys Phe Pro
        210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
                260                 265                 270

Leu Gly Lys Lys Pro Gln Asp Leu Phe Asp Glu Phe Ser Gly Lys His
            275                 280                 285

Lys Glu His Leu Gly Thr Gly Asp Val Lys Tyr His Met Gly Phe Ser
        290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
                340                 345                 350

Pro Ile Thr Ile His Gly Asp Ala Ala Ile Gly Gln Gly Val Val
            355                 360                 365

Gln Glu Thr Leu Asn Met Ser Gln Ala Arg Gly Tyr Glu Val Gly Gly
        370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
                420                 425                 430

Ala Phe Val Thr Arg Leu Ala Leu Asp Tyr Arg Asn Thr Phe Lys Arg
            435                 440                 445

Asp Val Phe Ile Asp Leu Val Cys Tyr Arg Arg His Gly His Asn Glu
        450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
                485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
        515                 520                 525

Ser Leu His Ser Phe Thr Trp Ser Pro Tyr Leu Asn His Glu Trp Asp
530                 535                 540

Glu Pro Tyr Pro Ala Gln Val Asp Met Lys Arg Leu Lys Glu Leu Ala
545                 550                 555                 560

Leu Arg Ile Ser Gln Val Pro Glu Gln Ile Glu Val Gln Ser Arg Val
                565                 570                 575

Ala Lys Ile Tyr Asn Asp Arg Lys Leu Met Ala Glu Gly Glu Lys Ala
            580                 585                 590
```

```
Phe Asp Trp Gly Gly Ala Glu Asn Leu Ala Tyr Ala Thr Leu Val Asp
            595                 600                 605

Glu Gly Ile Pro Val Arg Leu Ser Gly Glu Asp Ser Gly Arg Gly Thr
        610                 615                 620

Phe Phe His Arg His Ala Val His Asn Gln Ala Asn Gly Ser Thr
625                 630                 635                 640

Tyr Thr Pro Leu His His Ile His Asn Ser Gln Gly Glu Phe Lys Val
                645                 650                 655

Trp Asp Ser Val Leu Ser Glu Glu Ala Val Leu Ala Phe Glu Tyr Gly
            660                 665                 670

Tyr Ala Thr Ala Glu Pro Arg Val Leu Thr Ile Trp Glu Ala Gln Phe
        675                 680                 685

Gly Asp Phe Ala Asn Gly Ala Gln Val Val Ile Asp Gln Phe Ile Ser
690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
                725                 730                 735

Glu Arg Tyr Leu Gln Leu Cys Ala Glu Gln Asn Met Gly Val Cys Val
            740                 745                 750

Pro Ser Thr Pro Ala Gln Val Tyr His Met Leu Arg Arg Gln Ala Leu
        755                 760                 765

Arg Gly Met Arg Arg Pro Leu Val Val Met Ser Pro Lys Ser Leu Leu
770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
                805                 810                 815

Lys Arg Val Val Leu Cys Ser Gly Lys Val Tyr Tyr Asp Leu Leu Glu
            820                 825                 830

Gln Arg Arg Lys Asp Glu Lys Thr Asp Val Ala Ile Val Arg Ile Glu
        835                 840                 845

Gln Leu Tyr Pro Phe Pro His Gln Ala Val Gln Glu Ala Leu Lys Ala
850                 855                 860

Tyr Ser His Val Gln Asp Phe Val Trp Cys Gln Glu Glu Pro Leu Asn
865                 870                 875                 880

Gln Gly Ala Trp Tyr Cys Ser Gln His His Phe Arg Asp Val Val Pro
                885                 890                 895

Phe Gly Ala Thr Leu Arg Tyr Ala Gly Arg Pro Ala Ser Ala Ser Pro
            900                 905                 910

Ala Val Gly Tyr Met Ser Val His Gln Gln Gln Gln Gln Asp Leu Val
        915                 920                 925

Asn Asp Ala Leu Asn Val Asn
930                 935

<210> SEQ ID NO 49
<211> LENGTH: 407
<212> TYPE: PRT
<213> ORGANISM: Pantoea ananatis

<400> SEQUENCE: 49

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Ser
            20                  25                  30
```

Arg Asp Glu Val Ile Val Glu Ile Glu Thr Asp Lys Val Val Leu Glu
            35                  40                  45

Val Pro Ala Ser Ala Asp Gly Val Leu Glu Ala Val Leu Glu Asp Glu
 50                  55                  60

Gly Ala Thr Val Thr Ser Arg Gln Ile Leu Gly Arg Leu Lys Glu Gly
 65                  70                  75                  80

Asn Ser Ala Gly Lys Glu Ser Ser Ala Lys Ala Glu Ser Asn Asp Thr
                 85                  90                  95

Thr Pro Ala Gln Arg Gln Thr Ala Ser Leu Glu Glu Glu Ser Ser Asp
                100                 105                 110

Ala Leu Ser Pro Ala Ile Arg Arg Leu Ile Ala Glu His Asn Leu Asp
            115                 120                 125

Ala Ala Gln Ile Lys Gly Thr Gly Val Gly Gly Arg Leu Thr Arg Glu
130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Lys Ile Lys Glu Leu
290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
370                 375                 380

Glu Ser Val Gly Tyr Leu Val Ala Val Lys Glu Met Leu Glu Asp Pro
385                 390                 395                 400

Ala Arg Leu Leu Leu Asp Val
                405

<210> SEQ ID NO 50
<211> LENGTH: 40
<212> TYPE: PRT
<213> ORGANISM: Pantoea ananatis

<400> SEQUENCE: 50

| Met | Asn | Leu | His | Glu | Tyr | Gln | Ala | Lys | Gln | Leu | Phe | Ala | Arg | Tyr | Gly |
|---|---|---|---|---|---|---|---|---|---|---|---|---|---|---|---|
| 1 | | | | 5 | | | | | 10 | | | | | 15 | |

| Met | Pro | Ala | Pro | Thr | Gly | Tyr | Ala | Cys | Thr | Thr | Pro | Arg | Glu | Ala | Glu |
|---|---|---|---|---|---|---|---|---|---|---|---|---|---|---|---|
| | | | 20 | | | | | 25 | | | | | 30 | | |

| Glu | Ala | Ala | Ser | Lys | Ile | Gly | Ala |
|---|---|---|---|---|---|---|---|
| | | 35 | | | | 40 | |

<210> SEQ ID NO 51
<211> LENGTH: 4394
<212> TYPE: DNA
<213> ORGANISM: Corynebacterium glutamicum
<220> FEATURE:
<221> NAME/KEY: CDS
<222> LOCATION: (443)..(4213)

<400> SEQUENCE: 51

```
gtcgacaagc aaaatcgaag cggcagcacg ccgcgtcgga gccttaaacg ccatcgccgc      60
catccctgat ggtttcaatc atcaagtcgg tgaacgcggg cgcaacctgt catccggaca     120
gcgccaactg atcgcgctgg cgcgcgccga actcatcgag ccttccatca tgcttctcga     180
cgaagccacc tccaccctcg accccgccac cgaagccgtt atcctcaacg cctccgatcg     240
agtcactaag ggacgcacca gcatcatcgt cgcgcaccgc ttggcaaccg ctaaaagggc     300
cgaccgtatt cttgttgttg aacaaggacg tatcattgag gacggatctc acgacgcgtt     360
gttgtctgct aacggcacct acgcccgcat gtggcattta atggcctgac acgttatttt     420
taggagaact gtcaacaaat ta                                              442
```

| | | | atg | cta | caa | ctg | ggg | ctt | agg | cat | aat | cag | 472 |
|---|---|---|---|---|---|---|---|---|---|---|---|---|---|
| | | | Met | Leu | Gln | Leu | Gly | Leu | Arg | His | Asn | Gln | |
| | | | 1 | | | | 5 | | | | | 10 | |

| cca | acg | acc | aac | gtt | aca | gtg | gat | aaa | ata | aag | ctc | aat | aaa | ccc | tca | 520 |
|---|---|---|---|---|---|---|---|---|---|---|---|---|---|---|---|---|
| Pro | Thr | Thr | Asn | Val | Thr | Val | Asp | Lys | Ile | Lys | Leu | Asn | Lys | Pro | Ser | |
| | | | | 15 | | | | | 20 | | | | | 25 | | |

| aga | agc | aag | gaa | aag | agg | cga | gta | cct | gcc | gtg | agc | agc | gct | agt | act | 568 |
|---|---|---|---|---|---|---|---|---|---|---|---|---|---|---|---|---|
| Arg | Ser | Lys | Glu | Lys | Arg | Arg | Val | Pro | Ala | Val | Ser | Ser | Ala | Ser | Thr | |
| | | | 30 | | | | | 35 | | | | | 40 | | | |

| ttc | ggc | cag | aat | gcg | tgg | ctg | gta | gac | gag | atg | ttc | cag | cag | ttc | cag | 616 |
|---|---|---|---|---|---|---|---|---|---|---|---|---|---|---|---|---|
| Phe | Gly | Gln | Asn | Ala | Trp | Leu | Val | Asp | Glu | Met | Phe | Gln | Gln | Phe | Gln | |
| | | 45 | | | | | 50 | | | | | 55 | | | | |

| aag | gac | ccc | aag | tcc | gtg | gac | aag | gaa | tgg | aga | gaa | ctc | ttt | gag | gcg | 664 |
|---|---|---|---|---|---|---|---|---|---|---|---|---|---|---|---|---|
| Lys | Asp | Pro | Lys | Ser | Val | Asp | Lys | Glu | Trp | Arg | Glu | Leu | Phe | Glu | Ala | |
| 60 | | | | | 65 | | | | | 70 | | | | | | |

| cag | ggg | gga | cca | aat | gct | acc | ccc | gct | aca | aca | gaa | gca | cag | cct | tca | 712 |
|---|---|---|---|---|---|---|---|---|---|---|---|---|---|---|---|---|
| Gln | Gly | Gly | Pro | Asn | Ala | Thr | Pro | Ala | Thr | Thr | Glu | Ala | Gln | Pro | Ser | |
| 75 | | | | 80 | | | | | 85 | | | | | 90 | | |

| gcg | ccc | aag | gag | tct | gcg | aaa | cca | gca | cca | aag | gct | gcc | cct | gca | gcc | 760 |
|---|---|---|---|---|---|---|---|---|---|---|---|---|---|---|---|---|
| Ala | Pro | Lys | Glu | Ser | Ala | Lys | Pro | Ala | Pro | Lys | Ala | Ala | Pro | Ala | Ala | |
| | | | | 95 | | | | | 100 | | | | | 105 | | |

| aag | gca | gca | ccg | cgc | gta | gaa | acc | aag | ccg | gcc | gcc | aag | acc | gcc | cct | 808 |
|---|---|---|---|---|---|---|---|---|---|---|---|---|---|---|---|---|
| Lys | Ala | Ala | Pro | Arg | Val | Glu | Thr | Lys | Pro | Ala | Ala | Lys | Thr | Ala | Pro | |
| | | | 110 | | | | | 115 | | | | | 120 | | | |

| aag | gcc | aag | gag | tcc | tca | gtg | cca | cag | caa | cct | aag | ctt | ccg | gag | cca | 856 |
|---|---|---|---|---|---|---|---|---|---|---|---|---|---|---|---|---|
| Lys | Ala | Lys | Glu | Ser | Ser | Val | Pro | Gln | Gln | Pro | Lys | Leu | Pro | Glu | Pro | |
| | | 125 | | | | | 130 | | | | | 135 | | | | |

| gga | caa | acc | cca | atc | agg | ggt | att | ttc | aag | tcc | atc | gcg | aag | aac | atg | 904 |
|---|---|---|---|---|---|---|---|---|---|---|---|---|---|---|---|---|
| Gly | Gln | Thr | Pro | Ile | Arg | Gly | Ile | Phe | Lys | Ser | Ile | Ala | Lys | Asn | Met | |
| 140 | | | | | 145 | | | | | 150 | | | | | | |

| gat | atc | tcc | ctg | gaa | atc | cca | acc | gca | acc | tcg | gtt | cgc | gat | atg | cca | 952 |
|---|---|---|---|---|---|---|---|---|---|---|---|---|---|---|---|---|
| Asp | Ile | Ser | Leu | Glu | Ile | Pro | Thr | Ala | Thr | Ser | Val | Arg | Asp | Met | Pro | |
| 155 | | | | 160 | | | | | 165 | | | | | 170 | | |

| gct | cgc | ctc | atg | ttc | gaa | aac | cgc | gcg | atg | gta | aac | gat | cag | ctc | aag | 1000 |
|---|---|---|---|---|---|---|---|---|---|---|---|---|---|---|---|---|
| Ala | Arg | Leu | Met | Phe | Glu | Asn | Arg | Ala | Met | Val | Asn | Asp | Gln | Leu | Lys | |

```
                        175                 180                 185
cgc acc cgc ggt ggc aag atc tcc ttc acc cac atc att ggc tac gcc      1048
Arg Thr Arg Gly Gly Lys Ile Ser Phe Thr His Ile Ile Gly Tyr Ala
            190                 195                 200 atg gtg aag gca gtc atg gct cac ccg gac atg aac aac tcc tac gac      1096
Met Val Lys Ala Val Met Ala His Pro Asp Met Asn Asn Ser Tyr Asp
                205                 210                 215 gtc atc gac ggc aag cca acc ctg atc gtg cct gag cac atc aac ctg      1144
Val Ile Asp Gly Lys Pro Thr Leu Ile Val Pro Glu His Ile Asn Leu
        220                 225                 230 ggc ctt gcc atc gac ctt cct cag aag gac ggc tcc cgc gca ctt gtc      1192
Gly Leu Ala Ile Asp Leu Pro Gln Lys Asp Gly Ser Arg Ala Leu Val
235                 240                 245                 250 gta gca gcc atc aag gaa acc gag aag atg aac ttc tcc gag ttc ctc      1240
Val Ala Ala Ile Lys Glu Thr Glu Lys Met Asn Phe Ser Glu Phe Leu
                255                 260                 265 gca gca tac gaa gac atc gtg aca cgc tcc cgc aag ggc aag ctc acc      1288
Ala Ala Tyr Glu Asp Ile Val Thr Arg Ser Arg Lys Gly Lys Leu Thr
            270                 275                 280 atg gat gac tac cag ggc gtt acc gtt tcc ttg acc aac cca ggt ggc      1336
Met Asp Asp Tyr Gln Gly Val Thr Val Ser Leu Thr Asn Pro Gly Gly
        285                 290                 295 atc ggt acc cgc cac tct gtc cca cgt ctg acc aag ggc cag ggc acc      1384
Ile Gly Thr Arg His Ser Val Pro Arg Leu Thr Lys Gly Gln Gly Thr
300                 305                 310 atc atc ggt gtc ggt tcc atg gat tac cca gca gag ttc cag ggc gct      1432
Ile Ile Gly Val Gly Ser Met Asp Tyr Pro Ala Glu Phe Gln Gly Ala
315                 320                 325                 330 tcc gaa gac cgc ctt gca gag ctc ggc gtt gga aag ctt gtc acc atc      1480
Ser Glu Asp Arg Leu Ala Glu Leu Gly Val Gly Lys Leu Val Thr Ile
                335                 340                 345 acc tcc acc tac gat cac cgc gtg atc cag ggt gct gtg tcc ggt gaa      1528
Thr Ser Thr Tyr Asp His Arg Val Ile Gln Gly Ala Val Ser Gly Glu
            350                 355                 360 ttc ctg cgt acc atg tct cgc ctg ctc acc gat gat tcc ttc tgg gat      1576
Phe Leu Arg Thr Met Ser Arg Leu Leu Thr Asp Asp Ser Phe Trp Asp
        365                 370                 375 gag atc ttc gac gca atg aac gtt cct tac acc cca atg cgt tgg gca      1624
Glu Ile Phe Asp Ala Met Asn Val Pro Tyr Thr Pro Met Arg Trp Ala
380                 385                 390 cag gac gtt cca aac acc ggt gtt gat aag aac acc cgc gtc atg cag      1672
Gln Asp Val Pro Asn Thr Gly Val Asp Lys Asn Thr Arg Val Met Gln
395                 400                 405                 410 ctc att gag gca tac cgc tcc cgt gga cac ctc atc gct gac acc aac      1720
Leu Ile Glu Ala Tyr Arg Ser Arg Gly His Leu Ile Ala Asp Thr Asn
                415                 420                 425 cca ctt tca tgg gtt cag cct ggc atg cca gtt cca gac cac cgc gac      1768
Pro Leu Ser Trp Val Gln Pro Gly Met Pro Val Pro Asp His Arg Asp
            430                 435                 440 ctc gac atc gag acc cac agc ctg acc atc tgg gat ctg gac cgt acc      1816
Leu Asp Ile Glu Thr His Ser Leu Thr Ile Trp Asp Leu Asp Arg Thr
        445                 450                 455 ttc agc gtc ggt ggc ttc ggc ggc aag gag acc atg acc ctg cgc gag      1864
Phe Ser Val Gly Gly Phe Gly Gly Lys Glu Thr Met Thr Leu Arg Glu
460                 465                 470 gta ctg tcc cgc ctg cgc gct gcc tac acc ttg aag gtc ggc tcc gaa      1912
Val Leu Ser Arg Leu Arg Ala Ala Tyr Thr Leu Lys Val Gly Ser Glu
475                 480                 485                 490 tac acc cac atc ctg gac cgc gac gag cgc acc tgg ctg cag gac cgc      1960
Tyr Thr His Ile Leu Asp Arg Asp Glu Arg Thr Trp Leu Gln Asp Arg
```

-continued

```
              495                  500                  505
ctc gaa gcc gga atg cca aag cca acc cag gca gag cag aag tac atc    2008
Leu Glu Ala Gly Met Pro Lys Pro Thr Gln Ala Glu Gln Lys Tyr Ile
            510                  515                  520 ctg cag aag ctg aac gcc gca gag gct ttc gag aac ttc ctg cag acc    2056
Leu Gln Lys Leu Asn Ala Ala Glu Ala Phe Glu Asn Phe Leu Gln Thr
            525                  530                  535 aag tac gtc ggc cag aag cgc ttc tcc ctc gaa ggt gca gaa gct ctc    2104
Lys Tyr Val Gly Gln Lys Arg Phe Ser Leu Glu Gly Ala Glu Ala Leu
            540                  545                  550 atc cca ctg atg gac tcc gcc atc gac acc gcc gca ggc cag ggc ctc    2152
Ile Pro Leu Met Asp Ser Ala Ile Asp Thr Ala Ala Gly Gln Gly Leu
555                  560                  565                  570 gac gaa gtt gtc atc ggt atg cca cac cgt ggt cgc ctc aac gtg ctg    2200
Asp Glu Val Val Ile Gly Met Pro His Arg Gly Arg Leu Asn Val Leu
                    575                  580                  585 ttc aac atc gtg ggc aag cca ctg gca tcc atc ttc aac gag ttt gaa    2248
Phe Asn Ile Val Gly Lys Pro Leu Ala Ser Ile Phe Asn Glu Phe Glu
                590                  595                  600 ggc caa atg gag cag ggc cag atc ggt ggc tcc ggt gac gtg aag tac    2296
Gly Gln Met Glu Gln Gly Gln Ile Gly Gly Ser Gly Asp Val Lys Tyr
            605                  610                  615 cac ctc ggt tcc gaa ggc cag cac ctg cag atg ttc ggc gac ggc gag    2344
His Leu Gly Ser Glu Gly Gln His Leu Gln Met Phe Gly Asp Gly Glu
            620                  625                  630 atc aag gtc tcc ctg act gct aac ccg tcc cac ctg gaa gct gtt aac    2392
Ile Lys Val Ser Leu Thr Ala Asn Pro Ser His Leu Glu Ala Val Asn
635                  640                  645                  650 cca gtg atg gaa ggt atc gtc cgc gca aag cag gac tac ctg gac aag    2440
Pro Val Met Glu Gly Ile Val Arg Ala Lys Gln Asp Tyr Leu Asp Lys
                    655                  660                  665 ggc gta gac ggc aag act gtt gtg cca ctg ctg ctc cac ggt gac gct    2488
Gly Val Asp Gly Lys Thr Val Val Pro Leu Leu Leu His Gly Asp Ala
                670                  675                  680 gca ttc gca ggc ctg ggc atc gtg cca gaa acc atc aac ctg gct aag    2536
Ala Phe Ala Gly Leu Gly Ile Val Pro Glu Thr Ile Asn Leu Ala Lys
            685                  690                  695 ctg cgt ggc tac gac gtc gga ggc acc atc cac atc gtg gtg aac aac    2584
Leu Arg Gly Tyr Asp Val Gly Gly Thr Ile His Ile Val Val Asn Asn
            700                  705                  710 cag atc ggc ttc acc acc acc cca gac tcc agc cgc tcc atg cac tac    2632
Gln Ile Gly Phe Thr Thr Thr Pro Asp Ser Ser Arg Ser Met His Tyr
715                  720                  725                  730 gca acc gac tac gcc aag gca ttc ggc tgc cca gtc ttc cac gtc aat    2680
Ala Thr Asp Tyr Ala Lys Ala Phe Gly Cys Pro Val Phe His Val Asn
                    735                  740                  745 ggt gat gac cca gag gca gtt gtc tgg gtt ggc cag ctg gca acc gag    2728
Gly Asp Asp Pro Glu Ala Val Val Trp Val Gly Gln Leu Ala Thr Glu
                750                  755                  760 tac cgt cgt cgc ttc ggc aag gac gtc ttc atc gac ctc gtt tgc tac    2776
Tyr Arg Arg Arg Phe Gly Lys Asp Val Phe Ile Asp Leu Val Cys Tyr
            765                  770                  775 cgc ctc cgc ggc cac aac gaa gct gat gat cct tcc atg acc cag cca    2824
Arg Leu Arg Gly His Asn Glu Ala Asp Asp Pro Ser Met Thr Gln Pro
            780                  785                  790 aag atg tat gag ctc atc acc ggc cgc gag acc gtt cgt gct cag tac    2872
Lys Met Tyr Glu Leu Ile Thr Gly Arg Glu Thr Val Arg Ala Gln Tyr
795                  800                  805                  810 acc gaa gac ctg ctc gga cgt gga gac ctc tcc aac gaa gat gca gaa    2920
Thr Glu Asp Leu Leu Gly Arg Gly Asp Leu Ser Asn Glu Asp Ala Glu
```

-continued

|  |  |
|---|---|
| gca gtc gtc cgc gac ttc cac gac cag atg gaa tct gtg ttc aac gaa<br>Ala Val Val Arg Asp Phe His Asp Gln Met Glu Ser Val Phe Asn Glu<br>              830                        835                      840 | 2968 |
| gtc aag gaa ggc ggc aag aag cag gct gag gca cag acc ggc atc acc<br>Val Lys Glu Gly Gly Lys Lys Gln Ala Glu Ala Gln Thr Gly Ile Thr<br>        845                      850                      855 | 3016 |
| ggc tcc cag aag ctt cca cac ggc ctt gag acc aac atc tcc cgt gaa<br>Gly Ser Gln Lys Leu Pro His Gly Leu Glu Thr Asn Ile Ser Arg Glu<br>            860                      865                      870 | 3064 |
| gag ctc ctg gaa ctg gga cag gct ttc gcc aac acc cca gaa ggc ttc<br>Glu Leu Leu Glu Leu Gly Gln Ala Phe Ala Asn Thr Pro Glu Gly Phe<br>875                    880                      885                  890 | 3112 |
| aac tac cac cca cgt gtg gct cca gtt gct aag aag cgc gtc tcc tct<br>Asn Tyr His Pro Arg Val Ala Pro Val Ala Lys Lys Arg Val Ser Ser<br>                895                      900                      905 | 3160 |
| gtc acc gaa ggt ggc atc gac tgg gca tgg ggc gag ctc ctc gcc ttc<br>Val Thr Glu Gly Gly Ile Asp Trp Ala Trp Gly Glu Leu Leu Ala Phe<br>            910                      915                      920 | 3208 |
| ggt tcc ctg gct aac tcc ggc cgc ttg gtt cgc ctt gca ggt gaa gat<br>Gly Ser Leu Ala Asn Ser Gly Arg Leu Val Arg Leu Ala Gly Glu Asp<br>        925                      930                      935 | 3256 |
| tcc cgc cgc ggt acc ttc acc cag cgc cac gca gtt gcc atc gac cca<br>Ser Arg Arg Gly Thr Phe Thr Gln Arg His Ala Val Ala Ile Asp Pro<br>940                    945                      950 | 3304 |
| gcg acc gct gaa gag ttc aac cca ctc cac gag ctt gca cag tcc aag<br>Ala Thr Ala Glu Glu Phe Asn Pro Leu His Glu Leu Ala Gln Ser Lys<br>955                    960                      965                  970 | 3352 |
| ggc aac aac ggt aag ttc ctg gtc tac aac tcc gca ctg acc gag tac<br>Gly Asn Asn Gly Lys Phe Leu Val Tyr Asn Ser Ala Leu Thr Glu Tyr<br>                975                      980                      985 | 3400 |
| gca ggc atg ggc ttc gag tac ggc tac tcc gta gga aac gaa gac tcc<br>Ala Gly Met Gly Phe Glu Tyr Gly Tyr Ser Val Gly Asn Glu Asp Ser<br>            990                      995                     1000 | 3448 |
| gtc gtt gca tgg gaa gca cag ttc ggc gac ttc gcc aac ggc gct<br>Val Val Ala Trp Glu Ala Gln Phe Gly Asp Phe Ala Asn Gly Ala<br>               1005                  1010               1015 | 3493 |
| cag acc atc atc gat gag tac gtc tcc tca ggc gaa gct aag tgg<br>Gln Thr Ile Ile Asp Glu Tyr Val Ser Ser Gly Glu Ala Lys Trp<br>               1020                  1025               1030 | 3538 |
| ggc cag acc tcc aag ctg atc ctt ctg ctg cct cac ggc tac gaa<br>Gly Gln Thr Ser Lys Leu Ile Leu Leu Leu Pro His Gly Tyr Glu<br>               1035                  1040               1045 | 3583 |
| ggc cag ggc cca gac cac tct tcc gca cgt atc gag cgc ttc ctg<br>Gly Gln Gly Pro Asp His Ser Ser Ala Arg Ile Glu Arg Phe Leu<br>               1050                  1055               1060 | 3628 |
| cag ctg tgc gct gag ggt tcc atg act gtt gct cag cca tcc acc<br>Gln Leu Cys Ala Glu Gly Ser Met Thr Val Ala Gln Pro Ser Thr<br>               1065                  1070               1075 | 3673 |
| cca gca aac cac ttc cac ctg ctg cgt cgt cac gct ctg tcc gac<br>Pro Ala Asn His Phe His Leu Leu Arg Arg His Ala Leu Ser Asp<br>               1080                  1085               1090 | 3718 |
| ctg aag cgt cca ctg gtt atc ttc acc ccg aag tcc atg ctg cgt<br>Leu Lys Arg Pro Leu Val Ile Phe Thr Pro Lys Ser Met Leu Arg<br>               1095                  1100               1105 | 3763 |
| aac aag gct gct gcc tcc gca cca gaa gac ttc act gag gtc acc<br>Asn Lys Ala Ala Ala Ser Ala Pro Glu Asp Phe Thr Glu Val Thr<br>               1110                  1115               1120 | 3808 |
| aag ttc caa tcc gtg atc gac gat cca aac gtt gca gat gca gcc<br>Lys Phe Gln Ser Val Ile Asp Asp Pro Asn Val Ala Asp Ala Ala | 3853 |

```
            1125                1130                1135
aag gtg aag aag gtc atg ctg gtc tcc ggc aag ctg tac tac gaa    3898
Lys Val Lys Lys Val Met Leu Val Ser Gly Lys Leu Tyr Tyr Glu
    1140                1145                1150 ttg gca aag cgc aag gag aag gac gga cgc gac gac atc gcg atc    3943
Leu Ala Lys Arg Lys Glu Lys Asp Gly Arg Asp Asp Ile Ala Ile
    1155                1160                1165 gtt cgt atc gaa atg ctc cac cca att ccg ttc aac cgc atc tcc    3988
Val Arg Ile Glu Met Leu His Pro Ile Pro Phe Asn Arg Ile Ser
    1170                1175                1180 gag gct ctt gcc ggc tac cct aac gct gag gaa gtc ctc ttc gtt    4033
Glu Ala Leu Ala Gly Tyr Pro Asn Ala Glu Glu Val Leu Phe Val
    1185                1190                1195 cag gat gag cca gca aac cag ggc cca tgg ccg ttc tac cag gag    4078
Gln Asp Glu Pro Ala Asn Gln Gly Pro Trp Pro Phe Tyr Gln Glu
    1200                1205                1210 cac ctc cca gag ctg atc ccg aac atg cca aag atg cgc cgc gtt    4123
His Leu Pro Glu Leu Ile Pro Asn Met Pro Lys Met Arg Arg Val
    1215                1220                1225 tcc cgc cgc gct cag tcc tcc acc gca act ggt gtt gct aag gtg    4168
Ser Arg Arg Ala Gln Ser Ser Thr Ala Thr Gly Val Ala Lys Val
    1230                1235                1240 cac cag ctg gag gag aag cag ctt atc gac gag gct ttc gag gct    4213
His Gln Leu Glu Glu Lys Gln Leu Ile Asp Glu Ala Phe Glu Ala
    1245                1250                1255 taagtcttta tagtcctgca ctagcctaga gggccttatg cagtgtgaat cacacagcat    4273
aaggcccttt ttgctgccgt ggttgcctaa ggtggaaggc atgaaacgaa tctgtgcggt    4333
cacgatctct tcagtacttt tgctaagtgg ctgctcctcc acttccacca cgcagctcga    4393
g                                                                    4394
```

<210> SEQ ID NO 52
<211> LENGTH: 1257
<212> TYPE: PRT
<213> ORGANISM: Corynebacterium glutamicum

<400> SEQUENCE: 52

```
Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
                20                  25                  30

Arg Val Pro Ala Val Ser Ser Ala Ser Thr Phe Gly Gln Asn Ala Trp
            35                  40                  45

Leu Val Asp Glu Met Phe Gln Gln Phe Gln Lys Asp Pro Lys Ser Val
        50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
            100                 105                 110

Glu Thr Lys Pro Ala Ala Lys Thr Ala Pro Lys Ala Lys Glu Ser Ser
        115                 120                 125

Val Pro Gln Gln Pro Lys Leu Pro Glu Pro Gly Gln Thr Pro Ile Arg
    130                 135                 140

Gly Ile Phe Lys Ser Ile Ala Lys Asn Met Asp Ile Ser Leu Glu Ile
145                 150                 155                 160
```

```
Pro Thr Ala Thr Ser Val Arg Asp Met Pro Ala Arg Leu Met Phe Glu
            165                 170                 175

Asn Arg Ala Met Val Asn Asp Gln Leu Lys Arg Thr Arg Gly Gly Lys
            180                 185                 190

Ile Ser Phe Thr His Ile Ile Gly Tyr Ala Met Val Lys Ala Val Met
            195                 200                 205

Ala His Pro Asp Met Asn Asn Ser Tyr Asp Val Ile Asp Gly Lys Pro
            210                 215                 220

Thr Leu Ile Val Pro Glu His Ile Asn Leu Gly Leu Ala Ile Asp Leu
225                 230                 235                 240

Pro Gln Lys Asp Gly Ser Arg Ala Leu Val Ala Ala Ile Lys Glu
            245                 250                 255

Thr Glu Lys Met Asn Phe Ser Glu Phe Leu Ala Ala Tyr Glu Asp Ile
            260                 265                 270

Val Thr Arg Ser Arg Lys Gly Lys Leu Thr Met Asp Asp Tyr Gln Gly
            275                 280                 285

Val Thr Val Ser Leu Thr Asn Pro Gly Gly Ile Gly Thr Arg His Ser
            290                 295                 300

Val Pro Arg Leu Thr Lys Gly Gln Gly Thr Ile Ile Gly Val Gly Ser
305                 310                 315                 320

Met Asp Tyr Pro Ala Glu Phe Gln Gly Ala Ser Glu Asp Arg Leu Ala
            325                 330                 335

Glu Leu Gly Val Gly Lys Leu Val Thr Ile Thr Ser Thr Tyr Asp His
            340                 345                 350

Arg Val Ile Gln Gly Ala Val Ser Gly Glu Phe Leu Arg Thr Met Ser
            355                 360                 365

Arg Leu Leu Thr Asp Asp Ser Phe Trp Asp Glu Ile Phe Asp Ala Met
            370                 375                 380

Asn Val Pro Tyr Thr Pro Met Arg Trp Ala Gln Asp Val Pro Asn Thr
385                 390                 395                 400

Gly Val Asp Lys Asn Thr Arg Val Met Gln Leu Ile Glu Ala Tyr Arg
            405                 410                 415

Ser Arg Gly His Leu Ile Ala Asp Thr Asn Pro Leu Ser Trp Val Gln
            420                 425                 430

Pro Gly Met Pro Val Pro Asp His Arg Asp Leu Asp Ile Glu Thr His
            435                 440                 445

Ser Leu Thr Ile Trp Asp Leu Asp Arg Thr Phe Ser Val Gly Gly Phe
450                 455                 460

Gly Gly Lys Glu Thr Met Thr Leu Arg Glu Val Leu Ser Arg Leu Arg
465                 470                 475                 480

Ala Ala Tyr Thr Leu Lys Val Gly Ser Glu Tyr Thr His Ile Leu Asp
            485                 490                 495

Arg Asp Glu Arg Thr Trp Leu Gln Asp Arg Leu Glu Ala Gly Met Pro
            500                 505                 510

Lys Pro Thr Gln Ala Glu Gln Lys Tyr Ile Leu Gln Lys Leu Asn Ala
            515                 520                 525

Ala Glu Ala Phe Glu Asn Phe Leu Gln Thr Lys Tyr Val Gly Gln Lys
            530                 535                 540

Arg Phe Ser Leu Glu Gly Ala Glu Ala Leu Ile Pro Leu Met Asp Ser
545                 550                 555                 560

Ala Ile Asp Thr Ala Ala Gly Gln Gly Leu Asp Glu Val Val Ile Gly
            565                 570                 575

Met Pro His Arg Gly Arg Leu Asn Val Leu Phe Asn Ile Val Gly Lys
            580                 585                 590
```

```
Pro Leu Ala Ser Ile Phe Asn Glu Phe Glu Gly Gln Met Glu Gln Gly
            595                 600                 605

Gln Ile Gly Gly Ser Gly Asp Val Lys Tyr His Leu Gly Ser Glu Gly
        610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
                660                 665                 670

Val Val Pro Leu Leu His Gly Asp Ala Ala Phe Ala Gly Leu Gly
            675                 680                 685

Ile Val Pro Glu Thr Ile Asn Leu Ala Lys Leu Arg Gly Tyr Asp Val
        690                 695                 700

Gly Gly Thr Ile His Ile Val Val Asn Asn Gln Ile Gly Phe Thr Thr
705                 710                 715                 720

Thr Pro Asp Ser Ser Arg Ser Met His Tyr Ala Thr Asp Tyr Ala Lys
                725                 730                 735

Ala Phe Gly Cys Pro Val Phe His Val Asn Gly Asp Asp Pro Glu Ala
                740                 745                 750

Val Val Trp Val Gly Gln Leu Ala Thr Glu Tyr Arg Arg Arg Phe Gly
            755                 760                 765

Lys Asp Val Phe Ile Asp Leu Val Cys Tyr Arg Leu Arg Gly His Asn
770                 775                 780

Glu Ala Asp Asp Pro Ser Met Thr Gln Pro Lys Met Tyr Glu Leu Ile
785                 790                 795                 800

Thr Gly Arg Glu Thr Val Arg Ala Gln Tyr Thr Glu Asp Leu Leu Gly
                805                 810                 815

Arg Gly Asp Leu Ser Asn Glu Asp Ala Glu Ala Val Val Arg Asp Phe
                820                 825                 830

His Asp Gln Met Glu Ser Val Phe Asn Glu Val Lys Glu Gly Gly Lys
                835                 840                 845

Lys Gln Ala Glu Ala Gln Thr Gly Ile Thr Gly Ser Gln Lys Leu Pro
850                 855                 860

His Gly Leu Glu Thr Asn Ile Ser Arg Glu Glu Leu Leu Glu Leu Gly
865                 870                 875                 880

Gln Ala Phe Ala Asn Thr Pro Glu Gly Phe Asn Tyr His Pro Arg Val
                885                 890                 895

Ala Pro Val Ala Lys Lys Arg Val Ser Ser Val Thr Glu Gly Gly Ile
                900                 905                 910

Asp Trp Ala Trp Gly Glu Leu Leu Ala Phe Gly Ser Leu Ala Asn Ser
            915                 920                 925

Gly Arg Leu Val Arg Leu Ala Gly Glu Asp Ser Arg Arg Gly Thr Phe
        930                 935                 940

Thr Gln Arg His Ala Val Ala Ile Asp Pro Ala Thr Ala Glu Glu Phe
945                 950                 955                 960

Asn Pro Leu His Glu Leu Ala Gln Ser Lys Gly Asn Asn Gly Lys Phe
                965                 970                 975

Leu Val Tyr Asn Ser Ala Leu Thr Glu Tyr Ala Gly Met Gly Phe Glu
                980                 985                 990

Tyr Gly Tyr Ser Val Gly Asn Glu  Asp Ser Val Val Ala  Trp Glu Ala
            995                 1000                 1005

Gln Phe  Gly Asp Phe Ala Asn  Gly Ala Gln Thr Ile  Ile Asp Glu
```

-continued

```
                    1010                1015                1020

Tyr Val Ser Ser Gly Glu Ala Lys Trp Gly Gln Thr Ser Lys Leu
        1025                1030                1035

Ile Leu Leu Leu Pro His Gly Tyr Glu Gly Gln Gly Pro Asp His
        1040                1045                1050

Ser Ser Ala Arg Ile Glu Arg Phe Leu Gln Leu Cys Ala Glu Gly
        1055                1060                1065

Ser Met Thr Val Ala Gln Pro Ser Thr Pro Ala Asn His Phe His
        1070                1075                1080

Leu Leu Arg Arg His Ala Leu Ser Asp Leu Lys Arg Pro Leu Val
        1085                1090                1095

Ile Phe Thr Pro Lys Ser Met Leu Arg Asn Lys Ala Ala Ala Ser
        1100                1105                1110

Ala Pro Glu Asp Phe Thr Glu Val Thr Lys Phe Gln Ser Val Ile
        1115                1120                1125

Asp Asp Pro Asn Val Ala Asp Ala Ala Lys Val Lys Lys Val Met
        1130                1135                1140

Leu Val Ser Gly Lys Leu Tyr Tyr Glu Leu Ala Lys Arg Lys Glu
        1145                1150                1155

Lys Asp Gly Arg Asp Asp Ile Ala Ile Val Arg Ile Glu Met Leu
        1160                1165                1170

His Pro Ile Pro Phe Asn Arg Ile Ser Glu Ala Leu Ala Gly Tyr
        1175                1180                1185

Pro Asn Ala Glu Glu Val Leu Phe Val Gln Asp Glu Pro Ala Asn
        1190                1195                1200

Gln Gly Pro Trp Pro Phe Tyr Gln Glu His Leu Pro Glu Leu Ile
        1205                1210                1215

Pro Asn Met Pro Lys Met Arg Arg Val Ser Arg Arg Ala Gln Ser
        1220                1225                1230

Ser Thr Ala Thr Gly Val Ala Lys Val His Gln Leu Glu Glu Lys
        1235                1240                1245

Gln Leu Ile Asp Glu Ala Phe Glu Ala
        1250                1255

<210> SEQ ID NO 53
<211> LENGTH: 2028
<212> TYPE: DNA
<213> ORGANISM: Corynebacterium glutamicum
<220> FEATURE:
<221> NAME/KEY: CDS
<222> LOCATION: (1)..(2028)

<400> SEQUENCE: 53 atg gcg ttc tcc gta gag atg ccc gag ctg ggc gaa tca gta acc gaa      48
Met Ala Phe Ser Val Glu Met Pro Glu Leu Gly Glu Ser Val Thr Glu
1               5                   10                  15 ggc acg atc acc cag tgg ttg aag tct gtt ggt gac act gtt gag gta      96
Gly Thr Ile Thr Gln Trp Leu Lys Ser Val Gly Asp Thr Val Glu Val
            20                  25                  30 gat gag ccg ttg ctc gag gtc tca act gac aag gtc gac acc gag att     144
Asp Glu Pro Leu Leu Glu Val Ser Thr Asp Lys Val Asp Thr Glu Ile
        35                  40                  45 ccc tct cct gtc gcc ggt gtc atc cta gag att aag gct gaa gag gat     192
Pro Ser Pro Val Ala Gly Val Ile Leu Glu Ile Lys Ala Glu Glu Asp
    50                  55                  60 gac acc gtc gac gtc ggc ggt gtc att gca ata atc ggc gat gct gat     240
Asp Thr Val Asp Val Gly Gly Val Ile Ala Ile Ile Gly Asp Ala Asp
65                  70                  75                  80
```

| | | | |
|---|---|---|---|
| gag act cct gcc aac gaa gct cct gcc gac gag gca cca gct cct gcc<br>Glu Thr Pro Ala Asn Glu Ala Pro Ala Asp Glu Ala Pro Ala Pro Ala<br>85 90 95 | | | 288 |
| gaa gag gaa gaa cca gtt aag gaa gag cca aag aag gag gca gct cct<br>Glu Glu Glu Glu Pro Val Lys Glu Glu Pro Lys Lys Glu Ala Ala Pro<br>100 105 110 | | | 336 |
| gaa gct cca gca gca act ggc gcc gca acc gat gtg gaa atg cca gaa<br>Glu Ala Pro Ala Ala Thr Gly Ala Ala Thr Asp Val Glu Met Pro Glu<br>115 120 125 | | | 384 |
| ctc ggc gaa tcc gtc acc gaa ggc acc att acc cag tgg ctc aag gct<br>Leu Gly Glu Ser Val Thr Glu Gly Thr Ile Thr Gln Trp Leu Lys Ala<br>130 135 140 | | | 432 |
| gtc ggc gac acc gtc gaa gta gac gaa cca ctt ctt gag gtc tcc acc<br>Val Gly Asp Thr Val Glu Val Asp Glu Pro Leu Leu Glu Val Ser Thr<br>145 150 155 160 | | | 480 |
| gac aag gtc gac acc gaa atc cca tcc cca gta gca ggc acc atc gtg<br>Asp Lys Val Asp Thr Glu Ile Pro Ser Pro Val Ala Gly Thr Ile Val<br>165 170 175 | | | 528 |
| gag atc ctt gca gac gaa gac gac acc gtc gac gtc ggc gca gtc atc<br>Glu Ile Leu Ala Asp Glu Asp Asp Thr Val Asp Val Gly Ala Val Ile<br>180 185 190 | | | 576 |
| gcc cgc atc ggt gac gca aac gca gct gca gca cct gcc gaa gag gaa<br>Ala Arg Ile Gly Asp Ala Asn Ala Ala Ala Ala Pro Ala Glu Glu Glu<br>195 200 205 | | | 624 |
| gca gct cct gcc gaa gag gaa gaa cca gtt aag gaa gag cca aag aag<br>Ala Ala Pro Ala Glu Glu Glu Glu Pro Val Lys Glu Glu Pro Lys Lys<br>210 215 220 | | | 672 |
| gag gca gct cct gaa gct cca gca gca act ggc gcc gca acc gat gtg<br>Glu Ala Ala Pro Glu Ala Pro Ala Ala Thr Gly Ala Ala Thr Asp Val<br>225 230 235 240 | | | 720 |
| gaa atg cca gaa ctc ggc gaa tcc gtc acc gaa ggc acc att acc cag<br>Glu Met Pro Glu Leu Gly Glu Ser Val Thr Glu Gly Thr Ile Thr Gln<br>245 250 255 | | | 768 |
| tgg ctc aag gct gtc ggc gac acc gtc gaa gta gac gaa cca ctt ctt<br>Trp Leu Lys Ala Val Gly Asp Thr Val Glu Val Asp Glu Pro Leu Leu<br>260 265 270 | | | 816 |
| gag gtc tcc acc gac aag gtc gac acc gaa atc cca tcc cca gta gca<br>Glu Val Ser Thr Asp Lys Val Asp Thr Glu Ile Pro Ser Pro Val Ala<br>275 280 285 | | | 864 |
| ggc acc atc gtg gag atc ctt gca gac gaa gac gac acc gtc gac gtc<br>Gly Thr Ile Val Glu Ile Leu Ala Asp Glu Asp Asp Thr Val Asp Val<br>290 295 300 | | | 912 |
| ggc gca gtc atc gcc cgc atc ggt gac gca aac gca gct gca gca cct<br>Gly Ala Val Ile Ala Arg Ile Gly Asp Ala Asn Ala Ala Ala Ala Pro<br>305 310 315 320 | | | 960 |
| gcc gaa gag gaa gca gct cct gcc gaa gag gaa gaa cca gtt aag gaa<br>Ala Glu Glu Glu Ala Ala Pro Ala Glu Glu Glu Glu Pro Val Lys Glu<br>325 330 335 | | | 1008 |
| gag cca aag aag gaa gag ccc aag aag gaa gag ccc aag aag gaa gca<br>Glu Pro Lys Lys Glu Glu Pro Lys Lys Glu Glu Pro Lys Lys Glu Ala<br>340 345 350 | | | 1056 |
| gct act aca cct gct gcg gca tcc gca act gtg tcc gct tct ggc gac<br>Ala Thr Thr Pro Ala Ala Ala Ser Ala Thr Val Ser Ala Ser Gly Asp<br>355 360 365 | | | 1104 |
| aac gtt cca tac gtc acc cca ctg gtg cgc aag ctt gct gaa aag cac<br>Asn Val Pro Tyr Val Thr Pro Leu Val Arg Lys Leu Ala Glu Lys His<br>370 375 380 | | | 1152 |
| ggc gtt gac ttg aac acc gtg acc ggt acc ggt atc ggt ggc cgt atc<br>Gly Val Asp Leu Asn Thr Val Thr Gly Thr Gly Ile Gly Gly Arg Ile<br>385 390 395 400 | | | 1200 |

| | |
|---|---|
| cgc aag cag gat gtt ttg gct gct gcg aac ggc gag gct gca cct gct<br>Arg Lys Gln Asp Val Leu Ala Ala Ala Asn Gly Glu Ala Ala Pro Ala<br>                405                      410                    415 | 1248 |
| gag gct gct gct cct gtt tcc gct tgg tcc act aag tct gtt gac cct<br>Glu Ala Ala Ala Pro Val Ser Ala Trp Ser Thr Lys Ser Val Asp Pro<br>        420                      425                    430 | 1296 |
| gag aag gct aag ctc cgt ggt acc act cag aag gtc aac cgc atc cgt<br>Glu Lys Ala Lys Leu Arg Gly Thr Thr Gln Lys Val Asn Arg Ile Arg<br>435                      440                      445 | 1344 |
| gag atc acc gcg atg aag acc gtc gag gct ctg cag att tct gct cag<br>Glu Ile Thr Ala Met Lys Thr Val Glu Ala Leu Gln Ile Ser Ala Gln<br>    450                      455                    460 | 1392 |
| ctc acc cag ctg cac gag gtc gat atg act cgc gtt gct gag ctg cgt<br>Leu Thr Gln Leu His Glu Val Asp Met Thr Arg Val Ala Glu Leu Arg<br>465                      470                      475                    480 | 1440 |
| aag aag aac aag ccc gcg ttc atc gag aag cac ggt gtg aac ctc act<br>Lys Lys Asn Lys Pro Ala Phe Ile Glu Lys His Gly Val Asn Leu Thr<br>                485                      490                    495 | 1488 |
| tac ctg cca ttc ttc gtg aag gca gtt gtc gag gct ttg gtt tcc cat<br>Tyr Leu Pro Phe Phe Val Lys Ala Val Val Glu Ala Leu Val Ser His<br>        500                      505                    510 | 1536 |
| cca aac gtc aac gcg tct ttc aac gcg aag acc aag gag atg acc tac<br>Pro Asn Val Asn Ala Ser Phe Asn Ala Lys Thr Lys Glu Met Thr Tyr<br>            515                      520                    525 | 1584 |
| cac tcc tcc gtt aac ctc tcc atc gct gtt gat acc cca gct ggt ctg<br>His Ser Ser Val Asn Leu Ser Ile Ala Val Asp Thr Pro Ala Gly Leu<br>530                      535                      540 | 1632 |
| ttg acc cca gtc att cac gat gct cag gat ctc tcc atc cca gag atc<br>Leu Thr Pro Val Ile His Asp Ala Gln Asp Leu Ser Ile Pro Glu Ile<br>545                      550                      555                    560 | 1680 |
| gca aag gca att gtt gac ctg gct gat cgt tca cgc aac aac aag ctg<br>Ala Lys Ala Ile Val Asp Leu Ala Asp Arg Ser Arg Asn Asn Lys Leu<br>                565                      570                    575 | 1728 |
| aag cca aac gat ctg tcc ggt ggc acc ttc acc atc acc aac att ggt<br>Lys Pro Asn Asp Leu Ser Gly Gly Thr Phe Thr Ile Thr Asn Ile Gly<br>        580                      585                    590 | 1776 |
| tct gaa ggc gca ctg tct gat acc cca atc ctg gtt cca cca cag gct<br>Ser Glu Gly Ala Leu Ser Asp Thr Pro Ile Leu Val Pro Pro Gln Ala<br>            595                      600                    605 | 1824 |
| ggc atc ttg ggc acc ggc gcg atc gtg aag cgt cca gtt gtc atc acc<br>Gly Ile Leu Gly Thr Gly Ala Ile Val Lys Arg Pro Val Val Ile Thr<br>610                      615                      620 | 1872 |
| gag gat gga att gat tcc atc gcg atc cgt cag atg gtc ttc cta cca<br>Glu Asp Gly Ile Asp Ser Ile Ala Ile Arg Gln Met Val Phe Leu Pro<br>625                      630                      635                    640 | 1920 |
| ctg acc tac gac cac cag gtt gta gat ggc gca gat gct ggt cgc ttc<br>Leu Thr Tyr Asp His Gln Val Val Asp Gly Ala Asp Ala Gly Arg Phe<br>                645                      650                    655 | 1968 |
| ctg acc acc atc aag gac cgc ctt gag acc gct aac ttc gaa ggc gat<br>Leu Thr Thr Ile Lys Asp Arg Leu Glu Thr Ala Asn Phe Glu Gly Asp<br>        660                      665                    670 | 2016 |
| ctg cag ctc taa<br>Leu Gln Leu<br>        675 | 2028 |

<210> SEQ ID NO 54
<211> LENGTH: 675
<212> TYPE: PRT
<213> ORGANISM: Corynebacterium glutamicum

<400> SEQUENCE: 54

```
Met Ala Phe Ser Val Glu Met Pro Glu Leu Gly Glu Ser Val Thr Glu
1               5                   10                  15

Gly Thr Ile Thr Gln Trp Leu Lys Ser Val Gly Asp Thr Val Glu Val
            20                  25                  30

Asp Glu Pro Leu Leu Glu Val Ser Thr Asp Lys Val Asp Thr Glu Ile
        35                  40                  45

Pro Ser Pro Val Ala Gly Val Ile Leu Glu Ile Lys Ala Glu Glu Asp
    50                  55                  60

Asp Thr Val Asp Val Gly Gly Val Ile Ala Ile Ile Gly Asp Ala Asp
65                  70                  75                  80

Glu Thr Pro Ala Asn Glu Ala Pro Ala Asp Glu Ala Pro Ala Pro Ala
                85                  90                  95

Glu Glu Glu Glu Pro Val Lys Glu Glu Pro Lys Lys Glu Ala Ala Pro
                100                 105                 110

Glu Ala Pro Ala Ala Thr Gly Ala Ala Thr Asp Val Glu Met Pro Glu
            115                 120                 125

Leu Gly Glu Ser Val Thr Glu Gly Thr Ile Thr Gln Trp Leu Lys Ala
    130                 135                 140

Val Gly Asp Thr Val Glu Val Asp Glu Pro Leu Leu Glu Val Ser Thr
145                 150                 155                 160

Asp Lys Val Asp Thr Glu Ile Pro Ser Pro Val Ala Gly Thr Ile Val
                165                 170                 175

Glu Ile Leu Ala Asp Glu Asp Asp Thr Val Asp Val Gly Ala Val Ile
            180                 185                 190

Ala Arg Ile Gly Asp Ala Asn Ala Ala Ala Pro Ala Glu Glu Glu
            195                 200                 205

Ala Ala Pro Ala Glu Glu Glu Pro Val Lys Glu Glu Pro Lys Lys
    210                 215                 220

Glu Ala Ala Pro Glu Ala Pro Ala Ala Thr Gly Ala Ala Thr Asp Val
225                 230                 235                 240

Glu Met Pro Glu Leu Gly Glu Ser Val Thr Glu Gly Thr Ile Thr Gln
                245                 250                 255

Trp Leu Lys Ala Val Gly Asp Thr Val Glu Val Asp Glu Pro Leu Leu
            260                 265                 270

Glu Val Ser Thr Asp Lys Val Asp Thr Glu Ile Pro Ser Pro Val Ala
            275                 280                 285

Gly Thr Ile Val Glu Ile Leu Ala Asp Glu Asp Asp Thr Val Asp Val
    290                 295                 300

Gly Ala Val Ile Ala Arg Ile Gly Asp Ala Asn Ala Ala Ala Ala Pro
305                 310                 315                 320

Ala Glu Glu Glu Ala Ala Pro Ala Glu Glu Glu Pro Val Lys Glu
                325                 330                 335

Glu Pro Lys Lys Glu Glu Pro Lys Lys Glu Glu Pro Lys Lys Glu Ala
            340                 345                 350

Ala Thr Thr Pro Ala Ala Ser Ala Thr Val Ser Ala Ser Gly Asp
            355                 360                 365

Asn Val Pro Tyr Val Thr Pro Leu Val Arg Lys Leu Ala Glu Lys His
    370                 375                 380

Gly Val Asp Leu Asn Thr Val Thr Gly Thr Gly Ile Gly Gly Arg Ile
385                 390                 395                 400

Arg Lys Gln Asp Val Leu Ala Ala Ala Asn Gly Glu Ala Ala Pro Ala
                405                 410                 415

Glu Ala Ala Ala Pro Val Ser Ala Trp Ser Thr Lys Ser Val Asp Pro
```

-continued

```
                    420              425              430
Glu Lys Ala Lys Leu Arg Gly Thr Thr Gln Lys Val Asn Arg Ile Arg
            435                  440                  445
Glu Ile Thr Ala Met Lys Thr Val Glu Ala Leu Gln Ile Ser Ala Gln
        450                  455                  460
Leu Thr Gln Leu His Glu Val Asp Met Thr Arg Val Ala Glu Leu Arg
465                  470                  475                  480
Lys Lys Asn Lys Pro Ala Phe Ile Glu Lys His Gly Val Asn Leu Thr
                485                  490                  495
Tyr Leu Pro Phe Phe Val Lys Ala Val Val Glu Ala Leu Val Ser His
            500                  505                  510
Pro Asn Val Asn Ala Ser Phe Asn Ala Lys Thr Lys Glu Met Thr Tyr
        515                  520                  525
His Ser Ser Val Asn Leu Ser Ile Ala Val Asp Thr Pro Ala Gly Leu
    530                  535                  540
Leu Thr Pro Val Ile His Asp Ala Gln Asp Leu Ser Ile Pro Glu Ile
545                  550                  555                  560
Ala Lys Ala Ile Val Asp Leu Ala Asp Arg Ser Arg Asn Asn Lys Leu
                565                  570                  575
Lys Pro Asn Asp Leu Ser Gly Gly Thr Phe Thr Ile Thr Asn Ile Gly
            580                  585                  590
Ser Glu Gly Ala Leu Ser Asp Thr Pro Ile Leu Val Pro Pro Gln Ala
        595                  600                  605
Gly Ile Leu Gly Thr Gly Ala Ile Val Lys Arg Pro Val Val Ile Thr
    610                  615                  620
Glu Asp Gly Ile Asp Ser Ile Ala Ile Arg Gln Met Val Phe Leu Pro
625                  630                  635                  640
Leu Thr Tyr Asp His Gln Val Val Asp Gly Ala Asp Ala Gly Arg Phe
                645                  650                  655
Leu Thr Thr Ile Lys Asp Arg Leu Glu Thr Ala Asn Phe Glu Gly Asp
            660                  665                  670
Leu Gln Leu
        675

<210> SEQ ID NO 55
<211> LENGTH: 2802
<212> TYPE: DNA
<213> ORGANISM: Escherichia coli
<220> FEATURE:
<221> NAME/KEY: CDS
<222> LOCATION: (1)..(2802)

<400> SEQUENCE: 55 atg cag aac agc gct ttg aaa gcc tgg ttg gac tct tct tac ctc tct    48
Met Gln Asn Ser Ala Leu Lys Ala Trp Leu Asp Ser Ser Tyr Leu Ser
1               5                   10                  15 ggc gca aac cag agc tgg ata gaa cag ctc tat gaa gac ttc tta acc    96
Gly Ala Asn Gln Ser Trp Ile Glu Gln Leu Tyr Glu Asp Phe Leu Thr
            20                  25                  30 gat cct gac tcg gtt gac gct aac tgg cgt tcg acg ttc cag cag tta   144
Asp Pro Asp Ser Val Asp Ala Asn Trp Arg Ser Thr Phe Gln Gln Leu
        35                  40                  45 cct ggt acg gga gtc aaa ccg gat caa ttc cac tct caa acg cgt gaa   192
Pro Gly Thr Gly Val Lys Pro Asp Gln Phe His Ser Gln Thr Arg Glu
    50                  55                  60 tat ttc cgc cgc ctg gcg aaa gac gct tca cgt tac tct tca acg atc   240
Tyr Phe Arg Arg Leu Ala Lys Asp Ala Ser Arg Tyr Ser Ser Thr Ile
65                  70                  75                  80
```

```
tcc gac cct gac acc aat gtg aag cag gtt aaa gtc ctg cag ctc att         288
Ser Asp Pro Asp Thr Asn Val Lys Gln Val Lys Val Leu Gln Leu Ile
                85                  90                  95 aac gca tac cgc ttc cgt ggt cac cag cat gcg aat ctc gat ccg ctg         336
Asn Ala Tyr Arg Phe Arg Gly His Gln His Ala Asn Leu Asp Pro Leu
            100                 105                 110 gga ctg tgg cag caa gat aaa gtg gcc gat ctg gat ccg tct ttc cac         384
Gly Leu Trp Gln Gln Asp Lys Val Ala Asp Leu Asp Pro Ser Phe His
        115                 120                 125 gat ctg acc gaa gca gac ttc cag gag acc ttc aac gtc ggt tca ttt         432
Asp Leu Thr Glu Ala Asp Phe Gln Glu Thr Phe Asn Val Gly Ser Phe
    130                 135                 140 gcc agc ggc aaa gaa acc atg aaa ctc ggc gag ctg ctg gaa gcc ctc         480
Ala Ser Gly Lys Glu Thr Met Lys Leu Gly Glu Leu Leu Glu Ala Leu
145                 150                 155                 160 aag caa acc tac tgc ggc ccg att ggt gcc gag tat atg cac att acc         528
Lys Gln Thr Tyr Cys Gly Pro Ile Gly Ala Glu Tyr Met His Ile Thr
                165                 170                 175 agc acc gaa gaa aaa cgc tgg atc caa cag cgt atc gag tct ggt cgc         576
Ser Thr Glu Glu Lys Arg Trp Ile Gln Gln Arg Ile Glu Ser Gly Arg
            180                 185                 190 gcg act ttc aat agc gaa gag aaa aaa cgc ttc tta agc gaa ctg acc         624
Ala Thr Phe Asn Ser Glu Glu Lys Lys Arg Phe Leu Ser Glu Leu Thr
        195                 200                 205 gcc gct gaa ggt ctt gaa cgt tac ctc ggc gca aaa ttc cct ggc gca         672
Ala Ala Glu Gly Leu Glu Arg Tyr Leu Gly Ala Lys Phe Pro Gly Ala
    210                 215                 220 aaa cgc ttc tcg ctg gaa ggc ggt gac gcg tta atc ccg atg ctt aaa         720
Lys Arg Phe Ser Leu Glu Gly Gly Asp Ala Leu Ile Pro Met Leu Lys
225                 230                 235                 240 gag atg atc cgc cac gct ggc aac agc ggc acc cgc gaa gtg gtt ctc         768
Glu Met Ile Arg His Ala Gly Asn Ser Gly Thr Arg Glu Val Val Leu
                245                 250                 255 ggg atg gcg cac cgt ggt cgt ctg aac gtg ctg gtg aac gtg ctg ggt         816
Gly Met Ala His Arg Gly Arg Leu Asn Val Leu Val Asn Val Leu Gly
            260                 265                 270 aaa aaa ccg caa gac ttg ttc gac gag ttc gcc ggt aaa cat aaa gaa         864
Lys Lys Pro Gln Asp Leu Phe Asp Glu Phe Ala Gly Lys His Lys Glu
        275                 280                 285 cac ctc ggc acg ggt gac gtg aaa tac cac atg ggc ttc tcg tct gac         912
His Leu Gly Thr Gly Asp Val Lys Tyr His Met Gly Phe Ser Ser Asp
    290                 295                 300 ttc cag acc gat ggc ggc ctg gtg cac ctg gcg ctg gcg ttt aac ccg         960
Phe Gln Thr Asp Gly Gly Leu Val His Leu Ala Leu Ala Phe Asn Pro
305                 310                 315                 320 tct cac ctt gag att gta agc ccg gta gtt atc ggt tct gtt cgt gcc        1008
Ser His Leu Glu Ile Val Ser Pro Val Val Ile Gly Ser Val Arg Ala
                325                 330                 335 cgt ctg gac aga ctt gat gag ccg agc agc aac aaa gtg ctg cca atc        1056
Arg Leu Asp Arg Leu Asp Glu Pro Ser Ser Asn Lys Val Leu Pro Ile
            340                 345                 350 acc atc cac ggt gac gcc gca gtg acc ggg cag ggc gtg gtt cag gaa        1104
Thr Ile His Gly Asp Ala Ala Val Thr Gly Gln Gly Val Val Gln Glu
        355                 360                 365 acc ctg aac atg tcg aaa gcg cgt ggt tat gaa gtt ggc ggt acg gta        1152
Thr Leu Asn Met Ser Lys Ala Arg Gly Tyr Glu Val Gly Gly Thr Val
    370                 375                 380 cgt atc gtt atc aac aac cag gtt ggt ttc acc acc tct aat ccg ctg        1200
Arg Ile Val Ile Asn Asn Gln Val Gly Phe Thr Thr Ser Asn Pro Leu
385                 390                 395                 400
```

```
gat gcc cgt tct acg ccg tac tgt act gat atc ggt aag atg gtt cag      1248
Asp Ala Arg Ser Thr Pro Tyr Cys Thr Asp Ile Gly Lys Met Val Gln
            405                 410                 415 gcc ccg att ttc cac gtt aac gcg gac gat ccg gaa gcc gtt gcc ttt      1296
Ala Pro Ile Phe His Val Asn Ala Asp Asp Pro Glu Ala Val Ala Phe
        420                 425                 430 gtg acc cgt ctg gcg ctc gat ttc cgt aac acc ttt aaa cgt gat gtc      1344
Val Thr Arg Leu Ala Leu Asp Phe Arg Asn Thr Phe Lys Arg Asp Val
    435                 440                 445 ttc atc gac ctg gtg tgc tac cgc cgt cac ggc cac aac gaa gcc gac      1392
Phe Ile Asp Leu Val Cys Tyr Arg Arg His Gly His Asn Glu Ala Asp
450                 455                 460 gag ccg agc gca acc cag ccg ctg atg tat cag aaa atc aaa aaa cat      1440
Glu Pro Ser Ala Thr Gln Pro Leu Met Tyr Gln Lys Ile Lys Lys His
465                 470                 475                 480 ccg aca ccg cgc aaa atc tac gct gac aag ctg gag cag gaa aaa gtg      1488
Pro Thr Pro Arg Lys Ile Tyr Ala Asp Lys Leu Glu Gln Glu Lys Val
                485                 490                 495 gcg acg ctg gaa gat gcc acc gag atg gtt aac ctg tac cgc gat gcg      1536
Ala Thr Leu Glu Asp Ala Thr Glu Met Val Asn Leu Tyr Arg Asp Ala
            500                 505                 510 ctg gat gct ggc gat tgc gta gtg gca gag tgg cgt ccg atg aac atg      1584
Leu Asp Ala Gly Asp Cys Val Val Ala Glu Trp Arg Pro Met Asn Met
        515                 520                 525 cac tct ttc acc tgg tcg ccg tac ctc aac cac gaa tgg gac gaa gag      1632
His Ser Phe Thr Trp Ser Pro Tyr Leu Asn His Glu Trp Asp Glu Glu
    530                 535                 540 tac ccg aac aaa gtt gag atg aag cgc ctg cag gag ctg gcg aaa cgc      1680
Tyr Pro Asn Lys Val Glu Met Lys Arg Leu Gln Glu Leu Ala Lys Arg
545                 550                 555                 560 atc agc acg gtg ccg gaa gca gtt gaa atg cag tct cgc gtt gcc aag      1728
Ile Ser Thr Val Pro Glu Ala Val Glu Met Gln Ser Arg Val Ala Lys
                565                 570                 575 att tat ggc gat cgc cag gcg atg gct gcc ggt gag aaa ctg ttc gac      1776
Ile Tyr Gly Asp Arg Gln Ala Met Ala Ala Gly Glu Lys Leu Phe Asp
            580                 585                 590 tgg ggc ggt gcg gaa aac ctc gct tac gcc acg ctg gtt gat gaa ggc      1824
Trp Gly Gly Ala Glu Asn Leu Ala Tyr Ala Thr Leu Val Asp Glu Gly
        595                 600                 605 att ccg gtt cgc ctg tcg ggt gaa gac tcc ggt cgc ggt acc ttc ttc      1872
Ile Pro Val Arg Leu Ser Gly Glu Asp Ser Gly Arg Gly Thr Phe Phe
    610                 615                 620 cac cgc cac gcg gtg atc cac aac cag tct aac ggt tcc act tac acg      1920
His Arg His Ala Val Ile His Asn Gln Ser Asn Gly Ser Thr Tyr Thr
625                 630                 635                 640 ccg ctg caa cat atc cat aac ggg cag ggc gcg ttc cgt gtc tgg gac      1968
Pro Leu Gln His Ile His Asn Gly Gln Gly Ala Phe Arg Val Trp Asp
                645                 650                 655 tcc gta ctg tct gaa gaa gca gtg ctg gcg ttt gaa tat ggt tat gcc      2016
Ser Val Leu Ser Glu Glu Ala Val Leu Ala Phe Glu Tyr Gly Tyr Ala
            660                 665                 670 acc gca gaa cca cgc act ctg acc atc tgg gaa gcg cag ttc ggt gac      2064
Thr Ala Glu Pro Arg Thr Leu Thr Ile Trp Glu Ala Gln Phe Gly Asp
        675                 680                 685 ttc gcc aac ggt gcg cag gtg gtt atc gac cag ttc atc tcc tct ggc      2112
Phe Ala Asn Gly Ala Gln Val Val Ile Asp Gln Phe Ile Ser Ser Gly
    690                 695                 700 gaa cag aaa tgg ggc cgg atg tgt ggt ctg gtg atg ttg ctg ccg cac      2160
Glu Gln Lys Trp Gly Arg Met Cys Gly Leu Val Met Leu Leu Pro His
705                 710                 715                 720
```

```
ggt tac gaa ggg cag ggg ccg gag cac tcc tcc gcg cgt ctg gaa cgt      2208
Gly Tyr Glu Gly Gln Gly Pro Glu His Ser Ser Ala Arg Leu Glu Arg
                725                 730                 735 tat ctg caa ctt tgt gct gag caa aac atg cag gtt tgc gta ccg tct      2256
Tyr Leu Gln Leu Cys Ala Glu Gln Asn Met Gln Val Cys Val Pro Ser
            740                 745                 750 acc ccg gca cag gtt tac cac atg ctg cgt cgt cag gcg ctg cgc ggg      2304
Thr Pro Ala Gln Val Tyr His Met Leu Arg Arg Gln Ala Leu Arg Gly
        755                 760                 765 atg cgt cgt ccg ctg gtc gtg atg tcg ccg aaa tcc ctg ctg cgt cat      2352
Met Arg Arg Pro Leu Val Val Met Ser Pro Lys Ser Leu Leu Arg His
    770                 775                 780 ccg ctg gcg gtt tcc agc ctc gaa gaa ctg gcg aac ggc acc ttc ctg      2400
Pro Leu Ala Val Ser Ser Leu Glu Glu Leu Ala Asn Gly Thr Phe Leu
785                 790                 795                 800 cca gcc atc ggt gaa atc gac gag ctt gat ccg aag ggc gtg aag cgc      2448
Pro Ala Ile Gly Glu Ile Asp Glu Leu Asp Pro Lys Gly Val Lys Arg
                805                 810                 815 gta gtg atg tgt tct ggt aag gtt tat tac gac ctg ctg gaa cag cgt      2496
Val Val Met Cys Ser Gly Lys Val Tyr Tyr Asp Leu Leu Glu Gln Arg
            820                 825                 830 cgt aag aac aat caa cac gat gtc gcc att gtg cgt atc gag caa ctc      2544
Arg Lys Asn Asn Gln His Asp Val Ala Ile Val Arg Ile Glu Gln Leu
        835                 840                 845 tac ccg ttc ccg cat aaa gcg atg cag gaa gtg ttg cag cag ttt gct      2592
Tyr Pro Phe Pro His Lys Ala Met Gln Glu Val Leu Gln Gln Phe Ala
    850                 855                 860 cac gtc aag gat ttt gtc tgg tgc cag gaa gag ccg ctc aac cag ggc      2640
His Val Lys Asp Phe Val Trp Cys Gln Glu Glu Pro Leu Asn Gln Gly
865                 870                 875                 880 gca tgg tac tgc agc cag cat cat ttc cgt gaa gtg att ccg ttt ggg      2688
Ala Trp Tyr Cys Ser Gln His His Phe Arg Glu Val Ile Pro Phe Gly
                885                 890                 895 gct tct ctg cgt tat gca ggc cgc ccg gcc tcc gcc tct ccg gcg gta      2736
Ala Ser Leu Arg Tyr Ala Gly Arg Pro Ala Ser Ala Ser Pro Ala Val
            900                 905                 910 ggg tat atg tcc gtt cac cag aaa cag caa caa gat ctg gtt aat gac      2784
Gly Tyr Met Ser Val His Gln Lys Gln Gln Gln Asp Leu Val Asn Asp
        915                 920                 925 gcg ctg aac gtc gaa taa                                               2802
Ala Leu Asn Val Glu
    930

<210> SEQ ID NO 56
<211> LENGTH: 933
<212> TYPE: PRT
<213> ORGANISM: Escherichia coli

<400> SEQUENCE: 56

Met Gln Asn Ser Ala Leu Lys Ala Trp Leu Asp Ser Ser Tyr Leu Ser
1               5                   10                  15

Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu
        35                  40                  45

Pro Gly Thr Gly Val Lys Pro Asp Gln Phe His Ser Gln Thr Arg Glu
    50                  55                  60

Tyr Phe Arg Arg Leu Ala Lys Asp Ala Ser Arg Tyr Ser Ser Thr Ile
65                  70                  75                  80
```

```
Ser Asp Pro Asp Thr Asn Val Lys Gln Val Lys Val Leu Gln Leu Ile
             85                  90                  95

Asn Ala Tyr Arg Phe Arg Gly His Gln His Ala Asn Leu Asp Pro Leu
            100                 105                 110

Gly Leu Trp Gln Gln Asp Lys Val Ala Asp Leu Asp Pro Ser Phe His
        115                 120                 125

Asp Leu Thr Glu Ala Asp Phe Gln Glu Thr Phe Asn Val Gly Ser Phe
    130                 135                 140

Ala Ser Gly Lys Glu Thr Met Lys Leu Gly Glu Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
            180                 185                 190

Ala Thr Phe Asn Ser Glu Glu Lys Lys Arg Phe Leu Ser Glu Leu Thr
        195                 200                 205

Ala Ala Glu Gly Leu Glu Arg Tyr Leu Gly Ala Lys Phe Pro Gly Ala
    210                 215                 220

Lys Arg Phe Ser Leu Glu Gly Gly Asp Ala Leu Ile Pro Met Leu Lys
225                 230                 235                 240

Glu Met Ile Arg His Ala Gly Asn Ser Gly Thr Arg Glu Val Val Leu
                245                 250                 255

Gly Met Ala His Arg Gly Arg Leu Asn Val Leu Val Asn Val Leu Gly
            260                 265                 270

Lys Lys Pro Gln Asp Leu Phe Asp Glu Phe Ala Gly Lys His Lys Glu
        275                 280                 285

His Leu Gly Thr Gly Asp Val Lys Tyr His Met Gly Phe Ser Ser Asp
    290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
            340                 345                 350

Thr Ile His Gly Asp Ala Ala Val Thr Gly Gln Gly Val Val Gln Glu
        355                 360                 365

Thr Leu Asn Met Ser Lys Ala Arg Gly Tyr Glu Val Gly Gly Thr Val
    370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
            420                 425                 430

Val Thr Arg Leu Ala Leu Asp Phe Arg Asn Thr Phe Lys Arg Asp Val
        435                 440                 445

Phe Ile Asp Leu Val Cys Tyr Arg Arg His Gly His Asn Glu Ala Asp
    450                 455                 460

Glu Pro Ser Ala Thr Gln Pro Leu Met Tyr Gln Lys Ile Lys Lys His
465                 470                 475                 480

Pro Thr Pro Arg Lys Ile Tyr Ala Asp Lys Leu Glu Gln Glu Lys Val
                485                 490                 495

Ala Thr Leu Glu Asp Ala Thr Glu Met Val Asn Leu Tyr Arg Asp Ala
            500                 505                 510
```

```
Leu Asp Ala Gly Asp Cys Val Val Ala Glu Trp Arg Pro Met Asn Met
        515                 520                 525

His Ser Phe Thr Trp Ser Pro Tyr Leu Asn His Glu Trp Asp Glu Glu
        530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
                580                 585                 590

Trp Gly Gly Ala Glu Asn Leu Ala Tyr Ala Thr Leu Val Asp Glu Gly
        595                 600                 605

Ile Pro Val Arg Leu Ser Gly Glu Asp Ser Gly Arg Gly Thr Phe Phe
        610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
                660                 665                 670

Thr Ala Glu Pro Arg Thr Leu Thr Ile Trp Glu Ala Gln Phe Gly Asp
        675                 680                 685

Phe Ala Asn Gly Ala Gln Val Val Ile Asp Gln Phe Ile Ser Ser Gly
        690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
                740                 745                 750

Thr Pro Ala Gln Val Tyr His Met Leu Arg Arg Gln Ala Leu Arg Gly
        755                 760                 765

Met Arg Arg Pro Leu Val Val Met Ser Pro Lys Ser Leu Leu Arg His
770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
                820                 825                 830

Arg Lys Asn Asn Gln His Asp Val Ala Ile Val Arg Ile Glu Gln Leu
        835                 840                 845

Tyr Pro Phe Pro His Lys Ala Met Gln Glu Val Leu Gln Gln Phe Ala
        850                 855                 860

His Val Lys Asp Phe Val Trp Cys Gln Glu Glu Pro Leu Asn Gln Gly
865                 870                 875                 880

Ala Trp Tyr Cys Ser Gln His Phe Arg Glu Val Ile Pro Phe Gly
                885                 890                 895

Ala Ser Leu Arg Tyr Ala Gly Arg Pro Ala Ser Ala Ser Pro Ala Val
                900                 905                 910

Gly Tyr Met Ser Val His Gln Lys Gln Gln Asp Leu Val Asn Asp
        915                 920                 925

Ala Leu Asn Val Glu
```

-continued

930

<210> SEQ ID NO 57
<211> LENGTH: 1866
<212> TYPE: DNA
<213> ORGANISM: Blastopirellula marina
<220> FEATURE:
<221> NAME/KEY: CDS
<222> LOCATION: (1)..(1866)

<400> SEQUENCE: 57

| atg | tcc | acc | gaa | ttt | gaa | agc | gaa | act | gat | cac | tcc | aaa | gca | gtt | ttg | 48 |
|---|---|---|---|---|---|---|---|---|---|---|---|---|---|---|---|---|
| Met | Ser | Thr | Glu | Phe | Glu | Ser | Glu | Thr | Asp | His | Ser | Lys | Ala | Val | Leu | |
| 1 | | | | 5 | | | | | 10 | | | | | 15 | | |

| aag | att | gaa | gaa | gcg | act | gtc | cgc | ttt | tgc | ggc | gat | tct | ggc | gac | gga | 96 |
|---|---|---|---|---|---|---|---|---|---|---|---|---|---|---|---|---|
| Lys | Ile | Glu | Glu | Ala | Thr | Val | Arg | Phe | Cys | Gly | Asp | Ser | Gly | Asp | Gly | |
| | | 20 | | | | | 25 | | | | | 30 | | | | |

| atg | caa | ctc | gcc | gga | acc | cag | ttg | acc | aac | act | tcg | gcg | ctc | gcc | ggc | 144 |
|---|---|---|---|---|---|---|---|---|---|---|---|---|---|---|---|---|
| Met | Gln | Leu | Ala | Gly | Thr | Gln | Leu | Thr | Asn | Thr | Ser | Ala | Leu | Ala | Gly | |
| | | | 35 | | | | | 40 | | | | | 45 | | | |

| aac | gac | gtc | gcc | acc | ttt | ccc | gac | ttt | ccc | gcc | gag | att | cgc | gct | ccg | 192 |
|---|---|---|---|---|---|---|---|---|---|---|---|---|---|---|---|---|
| Asn | Asp | Val | Ala | Thr | Phe | Pro | Asp | Phe | Pro | Ala | Glu | Ile | Arg | Ala | Pro | |
| | 50 | | | | | 55 | | | | | 60 | | | | | |

| cgc | ggt | acg | ctc | gcc | ggc | gtc | tcc | ggc | ttt | cag | gtc | cat | ttc | tcg | tcg | 240 |
|---|---|---|---|---|---|---|---|---|---|---|---|---|---|---|---|---|
| Arg | Gly | Thr | Leu | Ala | Gly | Val | Ser | Gly | Phe | Gln | Val | His | Phe | Ser | Ser | |
| 65 | | | | | 70 | | | | | 75 | | | | | 80 | |

| acc | gac | att | tac | acg | ccg | ggt | gaa | acg | gtc | gac | gcg | ctg | atc | gcg | atg | 288 |
|---|---|---|---|---|---|---|---|---|---|---|---|---|---|---|---|---|
| Thr | Asp | Ile | Tyr | Thr | Pro | Gly | Glu | Thr | Val | Asp | Ala | Leu | Ile | Ala | Met | |
| | | | | 85 | | | | | 90 | | | | | 95 | | |

| aac | ccg | gcc | gct | ttg | aaa | acg | aac | atc | gcc | gac | ctc | aag | tca | ggc | ggc | 336 |
|---|---|---|---|---|---|---|---|---|---|---|---|---|---|---|---|---|
| Asn | Pro | Ala | Ala | Leu | Lys | Thr | Asn | Ile | Ala | Asp | Leu | Lys | Ser | Gly | Gly | |
| | | | 100 | | | | | 105 | | | | | 110 | | | |

| gtg | ctg | atc | gcc | aac | tcg | gac | gcg | ttt | gat | aaa | aaa | tcg | ctc | gaa | caa | 384 |
|---|---|---|---|---|---|---|---|---|---|---|---|---|---|---|---|---|
| Val | Leu | Ile | Ala | Asn | Ser | Asp | Ala | Phe | Asp | Lys | Lys | Ser | Leu | Glu | Gln | |
| | | 115 | | | | | 120 | | | | | 125 | | | | |

| gct | ggg | tac | gac | gac | aat | ccg | ctc | gat | gac | gag | acg | ctc | gat | tcg | tat | 432 |
|---|---|---|---|---|---|---|---|---|---|---|---|---|---|---|---|---|
| Ala | Gly | Tyr | Asp | Asp | Asn | Pro | Leu | Asp | Asp | Glu | Thr | Leu | Asp | Ser | Tyr | |
| | 130 | | | | | 135 | | | | | 140 | | | | | |

| caa | ctg | ttt | cag | gtt | ccg | atg | acc | gac | atg | acg | cgc | cgc | gcc | gtc | gac | 480 |
|---|---|---|---|---|---|---|---|---|---|---|---|---|---|---|---|---|
| Gln | Leu | Phe | Gln | Val | Pro | Met | Thr | Asp | Met | Thr | Arg | Arg | Ala | Val | Asp | |
| 145 | | | | | 150 | | | | | 155 | | | | | 160 | |

| ggg | ctt | gat | ctg | agt | caa | aaa | gaa | gcg | gac | cgc | tgc | cgc | aac | ttt | ttc | 528 |
|---|---|---|---|---|---|---|---|---|---|---|---|---|---|---|---|---|
| Gly | Leu | Asp | Leu | Ser | Gln | Lys | Glu | Ala | Asp | Arg | Cys | Arg | Asn | Phe | Phe | |
| | | | | 165 | | | | | 170 | | | | | 175 | | |

| gcc | atg | gga | ctg | gcg | ttt | tgg | ctc | tat | gga | cga | tcg | ctg | gaa | ccg | acg | 576 |
|---|---|---|---|---|---|---|---|---|---|---|---|---|---|---|---|---|
| Ala | Met | Gly | Leu | Ala | Phe | Trp | Leu | Tyr | Gly | Arg | Ser | Leu | Glu | Pro | Thr | |
| | | | 180 | | | | | 185 | | | | | 190 | | | |

| cgg | cga | ttt | atc | gat | ttg | aag | ttc | aaa | aag | ctg | ccg | gcc | atc | gcc | gaa | 624 |
|---|---|---|---|---|---|---|---|---|---|---|---|---|---|---|---|---|
| Arg | Arg | Phe | Ile | Asp | Leu | Lys | Phe | Lys | Lys | Leu | Pro | Ala | Ile | Ala | Glu | |
| | | 195 | | | | | 200 | | | | | 205 | | | | |

| gcg | aac | cgt | cgc | gcc | ctc | gcc | gcc | ggt | cgc | aat | tat | ggc | gaa | acg | acc | 672 |
|---|---|---|---|---|---|---|---|---|---|---|---|---|---|---|---|---|
| Ala | Asn | Arg | Arg | Ala | Leu | Ala | Ala | Gly | Arg | Asn | Tyr | Gly | Glu | Thr | Thr | |
| | 210 | | | | | 215 | | | | | 220 | | | | | |

| gat | gct | ttc | gtc | agc | tcg | ttt | tcg | gtc | gat | aaa | gca | aaa | ctg | tct | ccc | 720 |
|---|---|---|---|---|---|---|---|---|---|---|---|---|---|---|---|---|
| Asp | Ala | Phe | Val | Ser | Ser | Phe | Ser | Val | Asp | Lys | Ala | Lys | Leu | Ser | Pro | |
| 225 | | | | | 230 | | | | | 235 | | | | | 240 | |

| ggc | acg | tat | cgc | aat | atg | acc | ggc | aac | cag | gcg | ctg | gct | tgg | ggt | ttg | 768 |
|---|---|---|---|---|---|---|---|---|---|---|---|---|---|---|---|---|
| Gly | Thr | Tyr | Arg | Asn | Met | Thr | Gly | Asn | Gln | Ala | Leu | Ala | Trp | Gly | Leu | |
| | | | | 245 | | | | | 250 | | | | | 255 | | |

| atg | acg | gcg | gcc | aag | ttg | agc | gga | aaa | gag | ttg | ttt | ctc | ggt | tct | tat | 816 |
|---|---|---|---|---|---|---|---|---|---|---|---|---|---|---|---|---|
| Met | Thr | Ala | Ala | Lys | Leu | Ser | Gly | Lys | Glu | Leu | Phe | Leu | Gly | Ser | Tyr | |
| | | | 260 | | | | | 265 | | | | | 270 | | | |

```
ccg atc acg ccg gcc agt gat att ttg cat gaa ctg agc cgc tac aaa      864
Pro Ile Thr Pro Ala Ser Asp Ile Leu His Glu Leu Ser Arg Tyr Lys
        275                 280                 285 aac ttc ggc gtg cgg acg ttt cag gcc gaa gac gaa atc gcg gcg atc      912
Asn Phe Gly Val Arg Thr Phe Gln Ala Glu Asp Glu Ile Ala Ala Ile
    290                 295                 300 tgc tcg gcg atc ggc gcc gct tat tca gga cac atg gcg ctg acc acg      960
Cys Ser Ala Ile Gly Ala Ala Tyr Ser Gly His Met Ala Leu Thr Thr
305                 310                 315                 320 tcg agc gga cca ggg atc gcg ctc aaa gga gaa gcg atg ggc ctg gcg     1008
Ser Ser Gly Pro Gly Ile Ala Leu Lys Gly Glu Ala Met Gly Leu Ala
                325                 330                 335 gtc atg ctg gaa ttg ccg ctg ttg gtc gtg aac gtg cag cgc ggc gga     1056
Val Met Leu Glu Leu Pro Leu Leu Val Val Asn Val Gln Arg Gly Gly
        340                 345                 350 cca agc acc gga ctt cct acc aaa acg gag caa gcg gac ctg tta cag     1104
Pro Ser Thr Gly Leu Pro Thr Lys Thr Glu Gln Ala Asp Leu Leu Gln
    355                 360                 365 gtg atg ttt ggc cgc aac ggc gaa tgc ccg ctg ccg gtg ata tcg gct     1152
Val Met Phe Gly Arg Asn Gly Glu Cys Pro Leu Pro Val Ile Ser Ala
370                 375                 380 cgc agt ccg gcc gat tgt ttt gaa gtt gcg att gaa gca tgg cgc gtc     1200
Arg Ser Pro Ala Asp Cys Phe Glu Val Ala Ile Glu Ala Trp Arg Val
385                 390                 395                 400 gcc gcg cgg ttt atg acg ccg gtc atg atc ctc agc gac ggc tat ttg     1248
Ala Ala Arg Phe Met Thr Pro Val Met Ile Leu Ser Asp Gly Tyr Leu
                405                 410                 415 gcg aat ggg tcc gaa ccg tgg cgc atc gtc aac tat caa gat ctc aag     1296
Ala Asn Gly Ser Glu Pro Trp Arg Ile Val Asn Tyr Gln Asp Leu Lys
        420                 425                 430 ccg att ccg atc acc cat ccc gaa gcg ccg acc aac ggc aaa ccg ttt     1344
Pro Ile Pro Ile Thr His Pro Glu Ala Pro Thr Asn Gly Lys Pro Phe
    435                 440                 445 ttg gcg tac gaa cgt gac gag ctg ctc gct cgg cct tgg gcg atc ccc     1392
Leu Ala Tyr Glu Arg Asp Glu Leu Leu Ala Arg Pro Trp Ala Ile Pro
450                 455                 460 ggc acg cct ggg ttg atg cat cgc gtc ggc ggt tta gaa aaa gcg gat     1440
Gly Thr Pro Gly Leu Met His Arg Val Gly Gly Leu Glu Lys Ala Asp
465                 470                 475                 480 ggg acc ggc aac gtc agc tac gat cca atc aac cat cag cac atg acc     1488
Gly Thr Gly Asn Val Ser Tyr Asp Pro Ile Asn His Gln His Met Thr
                485                 490                 495 gac acc cgg gcg caa aaa gtg gcc aat gtc gcc caa gtg atc ggc gat     1536
Asp Thr Arg Ala Gln Lys Val Ala Asn Val Ala Gln Val Ile Gly Asp
        500                 505                 510 caa gag gtg atg ggg gat ccg gcc ggc gac ttg ttg gtg ctt agc tgg     1584
Gln Glu Val Met Gly Asp Pro Ala Gly Asp Leu Leu Val Leu Ser Trp
    515                 520                 525 ggc gga ccc tac gga tcg tgt cgc acg gcg gta acg cga ctc caa gcc     1632
Gly Gly Pro Tyr Gly Ser Cys Arg Thr Ala Val Thr Arg Leu Gln Ala
530                 535                 540 gaa ggg cac aag gtc agc cat gcg cat ctc cgg tgg ctc aat ccg ttc     1680
Glu Gly His Lys Val Ser His Ala His Leu Arg Trp Leu Asn Pro Phe
545                 550                 555                 560 ccg gcc aat ttg ggc gag atc ctg cgt agc ttt aag aag gtg ctc att     1728
Pro Ala Asn Leu Gly Glu Ile Leu Arg Ser Phe Lys Lys Val Leu Ile
                565                 570                 575 ccc gag ctg aac atg gga caa ctg tcg atg ttg att cgc aac caa ttt     1776
Pro Glu Leu Asn Met Gly Gln Leu Ser Met Leu Ile Arg Asn Gln Phe
        580                 585                 590
```

-continued

```
ttg atc gac acc atc ggc ctg aac aaa gtg caa ggc aaa ccg ttt cag      1824
Leu Ile Asp Thr Ile Gly Leu Asn Lys Val Gln Gly Lys Pro Phe Gln
            595                 600                 605 gtc gcc gag atc atc gac aaa gcg gaa tcg ctg ttg ccg taa              1866
Val Ala Glu Ile Ile Asp Lys Ala Glu Ser Leu Leu Pro
610                 615                 620
```

<210> SEQ ID NO 58
<211> LENGTH: 621
<212> TYPE: PRT
<213> ORGANISM: Blastopirellula marina

<400> SEQUENCE: 58

```
Met Ser Thr Glu Phe Glu Ser Glu Thr Asp His Ser Lys Ala Val Leu
1               5                   10                  15

Lys Ile Glu Glu Ala Thr Val Arg Phe Cys Gly Asp Ser Gly Asp Gly
                20                  25                  30

Met Gln Leu Ala Gly Thr Gln Leu Thr Asn Thr Ser Ala Leu Ala Gly
            35                  40                  45

Asn Asp Val Ala Thr Phe Pro Asp Phe Pro Ala Glu Ile Arg Ala Pro
    50                  55                  60

Arg Gly Thr Leu Ala Gly Val Ser Gly Phe Gln Val His Phe Ser Ser
65                  70                  75                  80

Thr Asp Ile Tyr Thr Pro Gly Glu Thr Val Asp Ala Leu Ile Ala Met
                85                  90                  95

Asn Pro Ala Ala Leu Lys Thr Asn Ile Ala Asp Leu Lys Ser Gly Gly
            100                 105                 110

Val Leu Ile Ala Asn Ser Asp Ala Phe Asp Lys Lys Ser Leu Glu Gln
        115                 120                 125

Ala Gly Tyr Asp Asp Asn Pro Leu Asp Asp Glu Thr Leu Asp Ser Tyr
    130                 135                 140

Gln Leu Phe Gln Val Pro Met Thr Asp Met Thr Arg Arg Ala Val Asp
145                 150                 155                 160

Gly Leu Asp Leu Ser Gln Lys Glu Ala Asp Arg Cys Arg Asn Phe Phe
                165                 170                 175

Ala Met Gly Leu Ala Phe Trp Leu Tyr Gly Arg Ser Leu Glu Pro Thr
            180                 185                 190

Arg Arg Phe Ile Asp Leu Lys Phe Lys Lys Leu Pro Ala Ile Ala Glu
        195                 200                 205

Ala Asn Arg Arg Ala Leu Ala Ala Gly Arg Asn Tyr Gly Glu Thr Thr
    210                 215                 220

Asp Ala Phe Val Ser Ser Phe Ser Val Asp Lys Ala Lys Leu Ser Pro
225                 230                 235                 240

Gly Thr Tyr Arg Asn Met Thr Gly Asn Gln Ala Leu Ala Trp Gly Leu
                245                 250                 255

Met Thr Ala Ala Lys Leu Ser Gly Lys Glu Leu Phe Leu Gly Ser Tyr
            260                 265                 270

Pro Ile Thr Pro Ala Ser Asp Ile Leu His Glu Leu Ser Arg Tyr Lys
        275                 280                 285

Asn Phe Gly Val Arg Thr Phe Gln Ala Glu Asp Glu Ile Ala Ala Ile
    290                 295                 300

Cys Ser Ala Ile Gly Ala Ala Tyr Ser Gly His Met Ala Leu Thr Thr
305                 310                 315                 320

Ser Ser Gly Pro Gly Ile Ala Leu Lys Gly Glu Ala Met Gly Leu Ala
                325                 330                 335
```

```
Val Met Leu Glu Leu Pro Leu Val Val Asn Val Gln Arg Gly Gly
            340                 345                 350

Pro Ser Thr Gly Leu Pro Thr Lys Thr Glu Gln Ala Asp Leu Leu Gln
        355                 360                 365

Val Met Phe Gly Arg Asn Gly Glu Cys Pro Leu Pro Val Ile Ser Ala
    370                 375                 380

Arg Ser Pro Ala Asp Cys Phe Glu Val Ala Ile Glu Ala Trp Arg Val
385                 390                 395                 400

Ala Ala Arg Phe Met Thr Pro Val Met Ile Leu Ser Asp Gly Tyr Leu
                405                 410                 415

Ala Asn Gly Ser Glu Pro Trp Arg Ile Val Asn Tyr Gln Asp Leu Lys
            420                 425                 430

Pro Ile Pro Ile Thr His Pro Glu Ala Pro Thr Asn Gly Lys Pro Phe
        435                 440                 445

Leu Ala Tyr Glu Arg Asp Glu Leu Leu Ala Arg Pro Trp Ala Ile Pro
    450                 455                 460

Gly Thr Pro Gly Leu Met His Arg Val Gly Gly Leu Glu Lys Ala Asp
465                 470                 475                 480

Gly Thr Gly Asn Val Ser Tyr Asp Pro Ile Asn His Gln His Met Thr
                485                 490                 495

Asp Thr Arg Ala Gln Lys Val Ala Asn Val Ala Gln Val Ile Gly Asp
            500                 505                 510

Gln Glu Val Met Gly Asp Pro Ala Gly Asp Leu Leu Val Leu Ser Trp
        515                 520                 525

Gly Gly Pro Tyr Gly Ser Cys Arg Thr Ala Val Thr Arg Leu Gln Ala
    530                 535                 540

Glu Gly His Lys Val Ser His Ala His Leu Arg Trp Leu Asn Pro Phe
545                 550                 555                 560

Pro Ala Asn Leu Gly Glu Ile Leu Arg Ser Phe Lys Lys Val Leu Ile
                565                 570                 575

Pro Glu Leu Asn Met Gly Gln Leu Ser Met Leu Ile Arg Asn Gln Phe
            580                 585                 590

Leu Ile Asp Thr Ile Gly Leu Asn Lys Val Gln Gly Lys Pro Phe Gln
        595                 600                 605

Val Ala Glu Ile Ile Asp Lys Ala Glu Ser Leu Leu Pro
    610                 615                 620

<210> SEQ ID NO 59
<211> LENGTH: 1020
<212> TYPE: DNA
<213> ORGANISM: Blastopirellula marina
<220> FEATURE:
<221> NAME/KEY: CDS
<222> LOCATION: (1)..(1020)

<400> SEQUENCE: 59 atg gct ccc gtc gaa cta ccc gtg ctc aag cct ggc gat ttc ggc agc      48
Met Ala Pro Val Glu Leu Pro Val Leu Lys Pro Gly Asp Phe Gly Ser
1               5                   10                  15 gat cag gat gtt cgc tgg tgc ccc ggt tgc ggc gac tat tcg att ctt      96
Asp Gln Asp Val Arg Trp Cys Pro Gly Cys Gly Asp Tyr Ser Ile Leu
                20                  25                  30 gcg cag atg aaa aaa gtg atg gcc gcc ctg gcg tgg ccg cgt gag aaa     144
Ala Gln Met Lys Lys Val Met Ala Ala Leu Ala Trp Pro Arg Glu Lys
            35                  40                  45 acg gtc ttc gtc tct ggg atc ggc tgc agc agt cgc ttt ccg tac tac     192
Thr Val Phe Val Ser Gly Ile Gly Cys Ser Ser Arg Phe Pro Tyr Tyr
        50                  55                  60
```

```
atg aac acg tac ggc atg cac agc att cat gga cgc gct ccc gct ttc      240
Met Asn Thr Tyr Gly Met His Ser Ile His Gly Arg Ala Pro Ala Phe
65              70                  75                  80 gcc acc ggc atc aag agt tgc cgt cct gat ctg cac gtc ttt gtc atc      288
Ala Thr Gly Ile Lys Ser Cys Arg Pro Asp Leu His Val Phe Val Ile
                85                  90                  95 acc ggc gac ggt gat gcg ctc agc atc ggc ggc aat cat ttt atg cat      336
Thr Gly Asp Gly Asp Ala Leu Ser Ile Gly Gly Asn His Phe Met His
            100                 105                 110 gtc gtt cgc cgt aac gta aac ttg aac att att ttg ttc aat aat cga      384
Val Val Arg Arg Asn Val Asn Leu Asn Ile Ile Leu Phe Asn Asn Arg
        115                 120                 125 ata tac ggg ctc acc aaa ggg caa tat tcg ccg act tcg gaa ttg ggc      432
Ile Tyr Gly Leu Thr Lys Gly Gln Tyr Ser Pro Thr Ser Glu Leu Gly
    130                 135                 140 aag atc acc aaa agt acg ccg atg ggg gcg atc gat aat ccg atg aat      480
Lys Ile Thr Lys Ser Thr Pro Met Gly Ala Ile Asp Asn Pro Met Asn
145                 150                 155                 160 ccc ctg tcg ctg gcg atc ggc tgc gaa gcg acc ttt gtc gcg cgg tcg      528
Pro Leu Ser Leu Ala Ile Gly Cys Glu Ala Thr Phe Val Ala Arg Ser
                165                 170                 175 atc gac gtg cat atc aaa cac ctg gcg gat acg ctg aag cga gcc gcc      576
Ile Asp Val His Ile Lys His Leu Ala Asp Thr Leu Lys Arg Ala Ala
            180                 185                 190 gaa cac cca gga gtc tcg ttt gtc gag gtt tat caa aac tgc aat gtg      624
Glu His Pro Gly Val Ser Phe Val Glu Val Tyr Gln Asn Cys Asn Val
        195                 200                 205 ttc aac gac ggc gcc tac aag tat gcg acc gac aaa tcg gtg aag tcg      672
Phe Asn Asp Gly Ala Tyr Lys Tyr Ala Thr Asp Lys Ser Val Lys Ser
    210                 215                 220 gac aat atc atc gaa atc gag cat ggc aag ccg ctg att ttt ggt aag      720
Asp Asn Ile Ile Glu Ile Glu His Gly Lys Pro Leu Ile Phe Gly Lys
225                 230                 235                 240 aat aga gac aag ggg att cgc tta aac ggc atg cag cca gaa gtg gtc      768
Asn Arg Asp Lys Gly Ile Arg Leu Asn Gly Met Gln Pro Glu Val Val
                245                 250                 255 gaa ctg ggt aaa ggc att acc gaa gac gac ctg ctg ttt cat gac gaa      816
Glu Leu Gly Lys Gly Ile Thr Glu Asp Asp Leu Leu Phe His Asp Glu
            260                 265                 270 cta gcc cca gag ccg acg ctc gcc tac ttg cta agt cgg atg cga tat      864
Leu Ala Pro Glu Pro Thr Leu Ala Tyr Leu Leu Ser Arg Met Arg Tyr
        275                 280                 285 cct gaa ttt ccc gag ccg atc ggc gtg ttg cgt tgc gtc gat gct cct      912
Pro Glu Phe Pro Glu Pro Ile Gly Val Leu Arg Cys Val Asp Ala Pro
    290                 295                 300 cgg tat gac gaa ctt tta aac gaa cag gtc gct caa gcg cga gcc gaa      960
Arg Tyr Asp Glu Leu Leu Asn Glu Gln Val Ala Gln Ala Arg Ala Glu
305                 310                 315                 320 aag gga gaa gga gac ttg gat aag ctc ttt cgc tct ggc gat acc tgg     1008
Lys Gly Glu Gly Asp Leu Asp Lys Leu Phe Arg Ser Gly Asp Thr Trp
                325                 330                 335 acg gta gaa tag                                                     1020
Thr Val Glu
```

<210> SEQ ID NO 60
<211> LENGTH: 339
<212> TYPE: PRT
<213> ORGANISM: Blastopirellula marina

<400> SEQUENCE: 60

```
Met Ala Pro Val Glu Leu Pro Val Leu Lys Pro Gly Asp Phe Gly Ser
1               5                   10                  15

Asp Gln Asp Val Arg Trp Cys Pro Cys Gly Asp Tyr Ser Ile Leu
            20                  25                  30

Ala Gln Met Lys Lys Val Met Ala Ala Leu Ala Trp Pro Arg Glu Lys
        35                  40                  45

Thr Val Phe Val Ser Gly Ile Gly Cys Ser Ser Arg Phe Pro Tyr Tyr
    50                  55                  60

Met Asn Thr Tyr Gly Met His Ser Ile His Gly Arg Ala Pro Ala Phe
65                  70                  75                  80

Ala Thr Gly Ile Lys Ser Cys Arg Pro Asp Leu His Val Phe Val Ile
                85                  90                  95

Thr Gly Asp Gly Asp Ala Leu Ser Ile Gly Gly Asn His Phe Met His
                100                 105                 110

Val Val Arg Arg Asn Val Asn Leu Asn Ile Ile Leu Phe Asn Asn Arg
            115                 120                 125

Ile Tyr Gly Leu Thr Lys Gly Gln Tyr Ser Pro Thr Ser Glu Leu Gly
        130                 135                 140

Lys Ile Thr Lys Ser Thr Pro Met Gly Ala Ile Asp Asn Pro Met Asn
145                 150                 155                 160

Pro Leu Ser Leu Ala Ile Gly Cys Glu Ala Thr Phe Val Ala Arg Ser
                165                 170                 175

Ile Asp Val His Ile Lys His Leu Ala Asp Thr Leu Lys Arg Ala Ala
            180                 185                 190

Glu His Pro Gly Val Ser Phe Val Glu Val Tyr Gln Asn Cys Asn Val
        195                 200                 205

Phe Asn Asp Gly Ala Tyr Lys Tyr Ala Thr Asp Lys Ser Val Lys Ser
210                 215                 220

Asp Asn Ile Ile Glu Ile Glu His Gly Lys Pro Leu Ile Phe Gly Lys
225                 230                 235                 240

Asn Arg Asp Lys Gly Ile Arg Leu Asn Gly Met Gln Pro Glu Val Val
                245                 250                 255

Glu Leu Gly Lys Gly Ile Thr Glu Asp Asp Leu Leu Phe His Asp Glu
            260                 265                 270

Leu Ala Pro Glu Pro Thr Leu Ala Tyr Leu Leu Ser Arg Met Arg Tyr
        275                 280                 285

Pro Glu Phe Pro Glu Pro Ile Gly Val Leu Arg Cys Val Asp Ala Pro
290                 295                 300

Arg Tyr Asp Glu Leu Leu Asn Glu Gln Val Ala Gln Ala Arg Ala Glu
305                 310                 315                 320

Lys Gly Glu Gly Asp Leu Asp Lys Leu Phe Arg Ser Gly Asp Thr Trp
                325                 330                 335

Thr Val Glu

<210> SEQ ID NO 61
<211> LENGTH: 59
<212> TYPE: DNA
<213> ORGANISM: Artificial
<220> FEATURE:
<223> OTHER INFORMATION: primer

<400> SEQUENCE: 61
tctggcggta cctaaggagg aatcacgtga tgtccaccga atttgaaagc gaaactgat         59

<210> SEQ ID NO 62
<211> LENGTH: 46
```

```
<212> TYPE: DNA
<213> ORGANISM: Artificial
<220> FEATURE:
<223> OTHER INFORMATION: primer

<400> SEQUENCE: 62
aaacccgaat tcgtcactat tctaccgtcc aggtatcgcc agagcg          46

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
ccaggcactc gtcctcggtt                                       20

<210> SEQ ID NO 64
<211> LENGTH: 48
<212> TYPE: DNA
<213> ORGANISM: Artificial
<220> FEATURE:
<223> OTHER INFORMATION: primer

<400> SEQUENCE: 64
aggctagtgc aggactataa agaccagttc tcctaaaaat aacgtgtc        48

<210> SEQ ID NO 65
<211> LENGTH: 48
<212> TYPE: DNA
<213> ORGANISM: Artificial
<220> FEATURE:
<223> OTHER INFORMATION: primer

<400> SEQUENCE: 65
gacacgttat ttttaggaga actggtcttt atagtcctgc actagcct        48

<210> SEQ ID NO 66
<211> LENGTH: 21
<212> TYPE: DNA
<213> ORGANISM: Artificial
<220> FEATURE:
<223> OTHER INFORMATION: primer

<400> SEQUENCE: 66
tccatcgtgg gccaccgatc c                                     21

<210> SEQ ID NO 67
<211> LENGTH: 51
<212> TYPE: DNA
<213> ORGANISM: Artificial
<220> FEATURE:
<223> OTHER INFORMATION: primer

<400> SEQUENCE: 67
tttctgcagt aaggaggaat gaccatgagt gacaccgtaa tcttaaacaa c    51

<210> SEQ ID NO 68
<211> LENGTH: 36
<212> TYPE: DNA
<213> ORGANISM: Artificial
<220> FEATURE:
<223> OTHER INFORMATION: primer

<400> SEQUENCE: 68
aaatctagat cgtgatcagt tgatcgtcca ggtgct                     36
```

<210> SEQ ID NO 69
<211> LENGTH: 44
<212> TYPE: DNA
<213> ORGANISM: Artificial
<220> FEATURE:
<223> OTHER INFORMATION: primer

<400> SEQUENCE: 69
gaagtccagg aggacataca atgagtgaca ccgtaatctt aaac         44

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
gagtgcgagg tagccgtcgg                                     20

<210> SEQ ID NO 71
<211> LENGTH: 26
<212> TYPE: DNA
<213> ORGANISM: Artificial
<220> FEATURE:
<223> OTHER INFORMATION: primer

<400> SEQUENCE: 71
agatcgttta gatccgaagg aaaacg                              26

<210> SEQ ID NO 72
<211> LENGTH: 44
<212> TYPE: DNA
<213> ORGANISM: Artificial
<220> FEATURE:
<223> OTHER INFORMATION: primer

<400> SEQUENCE: 72
gtttaagatt acggtgtcac tcattgtatg tcctcctgga cttc         44

<210> SEQ ID NO 73
<211> LENGTH: 28
<212> TYPE: DNA
<213> ORGANISM: Artificial
<220> FEATURE:
<223> OTHER INFORMATION: primer

<400> SEQUENCE: 73
tttctgcagg caatttgctt ttcgacgc                            28

<210> SEQ ID NO 74
<211> LENGTH: 20
<212> TYPE: DNA
<213> ORGANISM: Artificial
<220> FEATURE:
<223> OTHER INFORMATION: primer

<400> SEQUENCE: 74
cggcgatctt cgcggcttcg                                     20

<210> SEQ ID NO 75
<211> LENGTH: 29
<212> TYPE: DNA
<213> ORGANISM: Artificial
<220> FEATURE:
<223> OTHER INFORMATION: primer

```
<400> SEQUENCE: 75
tttctgcaga gatcgtttag atccgaagg                                        29

<210> SEQ ID NO 76
<211> LENGTH: 31
<212> TYPE: DNA
<213> ORGANISM: Artificial
<220> FEATURE:
<223> OTHER INFORMATION: primer

<400> SEQUENCE: 76
tttctgcagt gtatgtcctc ctggacttcg t                                     31

<210> SEQ ID NO 77
<211> LENGTH: 362
<212> TYPE: DNA
<213> ORGANISM: Brevibacterium flavum

<400> SEQUENCE: 77
agatcgttta gatccgaagg aaaacgtcga aaagcaattt gcttttcgac gccccacccc      60
gcgcgtttta gcgtgtcagt aggcgcgtag ggtaagtggg gtagcggctt gttagatatc     120
ttgaaatcgg ctttcaacag cattgatttc gatgtattta gctggccgtt accctgcgaa     180
tgtccacagg gtagctggta gtttgaaaat caacgccgtt gcccttagga ttcagtaact     240
ggcacatttt gtaatgcgct agatctgtgt gctcagtctt ccaggctgct gatcacagtg     300
aaagcaaaac caattcgtgg ctgcgaaagt cgtagccacc acgaagtcca ggaggacata     360
ca                                                                    362
```

MICROORGANISM PRODUCING AN AMINO ACID OF THE L-GLUTAMIC ACID FAMILY AND A METHOD FOR PRODUCING THE AMINO ACID

This application is a continuation under 35 U.S.C. §120 of PCT Patent Application No. PCT/JP2008/054735, filed Mar. 14, 2008, which claims priority under 35 U.S.C. §119 to Japanese Patent Application No. 2007-065367, filed on Mar. 14, 2007, which are incorporated in their entireties by reference. The Sequence Listing in electronic format filed herewith is also hereby incorporated by reference in its entirety (File Name: US-404_Seq_List; File Size: 194 KB; Date Created: Sep. 8, 2009).

BACKGROUND OF THE INVENTION

1. Field of the Invention

The present invention relates to a microorganism which produces an amino acid of the L-glutamic acid family and a method for producing the amino acid. L-Glutamic acid is widely used as a raw material of seasonings and so forth. L-Glutamine, L-proline, L-ornithine, L-citrulline and L-arginine are useful for seasonings, liver function promoting agents, amino acid infusions, general amino acid pharmaceuticals and so forth.

2. Brief Description of the Related Art

L-Glutamic acid is produced mainly by fermentation utilizing L-glutamic acid producing bacteria of the so-called coryneform bacteria belonging to the genus *Brevibacterium*, *Corynebacterium* or *Microbacterium* or mutant strains thereof (see, for example, Akashi K. et al., Amino Acid Fermentation, Japan Scientific Societies Press, pp. 195-215, 1986). As methods for producing L-glutamic acid by fermentation using other bacterial strains, the following methods are known: methods using a microorganism belonging to the genus *Bacillus, Streptomyces, Penicillium* or the like (refer to, for example, U.S. Pat. No. 3,220,929), methods using a microorganism belonging to the genus *Pseudomonas, Arthrobacter, Serratia, Candida* or the like (refer to, for example, U.S. Pat. No. 3,563,857), methods using a microorganism belonging to the genus *Bacillus, Pseudomonas, Serratia* or the like, or *Aerobacter aerogenes* (currently referred to as *Enterobacter aerogenes*) (refer to, for example, Japanese Patent Publication (KOKOKU) No. 32-9393), methods using a mutant strain of *Escherichia coli* (refer to, for example, Japanese Patent Laid-open (KOKAI) No. 5-244970), and so forth. In addition, methods for producing L-glutamic acid using a microorganism belonging to the genus *Klebsiella, Erwinia, Pantoea* or *Enterobacter* are also disclosed (refer to, for example, Japanese Patent Laid-open No. 2000-106869, Japanese Patent Laid-open No. 2000-189169, and Japanese Patent Laid-open No. 2000-189175).

Furthermore, various techniques for increasing L-glutamic acid producing ability by enhancing L-glutamic acid biosynthetic enzymes using recombinant DNA techniques have been disclosed. For example, it has been reported for *Corynebacterium* or *Brevibacterium* bacteria that introduction of a gene encoding citrate synthase of *Escherichia coli* or *Corynebacterium glutamicum* was effective for enhancement of L-glutamic acid producing ability of coryneform bacteria (refer to, for example, Japanese Patent Publication No. 7-121228). Furthermore, it has also been reported that introduction of a citrate synthase gene of a coryneform bacterium into enterobacteria belonging to the genus *Enterobacter, Klebsiella, Serratia, Erwinia* or *Escherichia* was effective for enhancement of L-glutamic acid producing ability thereof (refer to, for example, Japanese Patent Laid-open No. 2000-189175).

Amino acids of the L-glutamic acid family other than L-glutamic acid, for example, ornithine and citrullines (Lee, Y.-J. and Cho, J.-Y. 2006. Biotechnol. Lett. 28:1849-1856, Choi, D. K. et al. 1996. J. Ferment. Bioeng. 81:216-219, and Non-patent document 4: Plachy, J. 1987. Kvasny Prumysl, 33:73-75), L-glutamine (Japanese Patent Laid-open No. 2002-300887), L-proline (European Patent No. 1172433), L-arginine (Japanese Patent Laid-open No. 2000-287693 and Japanese Patent Laid-open No. 2001-046082), and so forth are also produced by the aforementioned fermentation methods using microorganisms as the same as L-glutamic acid.

SUMMARY OF THE INVENTION

An aspect in accordance with the presently disclosed subject matter is to provide a microbial strain that can efficiently produce an amino acid of the L-glutamic acid family and to provide a method for efficiently producing the amino acid using such a strain.

The aforementioned techniques for enhancing the L-glutamic acid producing ability mainly employ enhancing activity of a TCA cycle enzyme. L-glutamic acid fermentation which occurs via the TCA cycle accompanies decarboxylation catalyzed by isocitrate dehydrogenase, and therefore one molecule of $CO_2$ is necessarily released. Therefore, in order to further enhance the productivity, it was necessary to decrease this decarboxylation. It was determined that the productivity of L-glutamic acid could be improved by increasing the enzymatic activity of α-ketoglutarate synthase, which is an enzyme of the reductive TCA cycle, and additionally enhancing the enzymatic activity of ferredoxin $NADP^+$ reductase or pyruvate synthase. These enzymes enable production of reduced ferredoxin and reduced flavodoxin, which are necessary for the enzymatic activity of α-ketoglutarate synthase, from the oxidized forms of ferredoxin and flavodoxin, respectively. It was further determined that the productivity of L-glutamic acid could also be improved by increasing the ability to produce ferredoxin or flavodoxin.

That is, the presently disclosed subject matter can provide the following:

It is an aspect of the present invention to provide a microorganism which is able to produce an L-amino acid selected from the group consisting of L-glutamic acid, L-glutamine, L-proline, L-ornithine, L-citrulline, L-arginine, and combinations thereof, wherein the microorganism has been modified to increase α-ketoglutarate synthase activity.

It is a further aspect of the present invention to provide microorganism as described above, wherein the α-ketoglutarate synthase activity is increased by increasing expression of a gene encoding α-ketoglutarate synthase and/or by increasing translation of the gene.

It is a further aspect of the present invention to provide the microorganism as described above, wherein the expression of the gene encoding α-ketoglutarate synthase is increased by increasing the copy number of the gene or by modifying an expression control sequence of the gene.

It is a further aspect of the present invention to provide the microorganism as described above, wherein said α-ketoglutarate synthase comprises an α subunit and a β subunit, and the α subunit is selected from the group consisting of:

(A) a polypeptide comprising the amino acid sequence of SEQ ID NO: 2, (B) a polypeptide comprising the amino acid sequence of SEQ ID NO: 2, but which includes substitutions, deletions, insertions or additions of one or several amino acids, and said polypeptide has α-ketoglutarate synthase activity when complexed with the β subunit, (C) a polypeptide comprising the amino acid sequence of SEQ ID NO: 58, and (D) a polypeptide comprising the amino acid sequence of SEQ ID NO: 58, but which includes substitutions, deletions, insertions or additions of one or several amino acids, and wherein said polypeptide has α-ketoglutarate synthase activity when complexed with the β subunit, and the β subunit is selected from the group consisting of:

(E) a polypeptide comprising the amino acid sequence of SEQ ID NO: 4, (F) a polypeptide comprising the amino acid sequence of SEQ ID NO: 4, but which includes substitutions, deletions, insertions or additions of one or several amino acids, and wherein said polypeptide has α-ketoglutarate synthase activity when complexed with the α subunit, (G) a polypeptide comprising the amino acid sequence of SEQ ID NO: 60, and (H) a polypeptide comprising the amino acid sequence of SEQ ID NO: 60, but which includes substitutions, deletions, insertions or additions of one or several amino acids, and wherein said polypeptide has α-ketoglutarate synthase activity when complexed with the α subunit.

It is another aspect of the present invention to provide the microorganism as described above, wherein said α-ketoglutarate synthase comprises an α subunit and a β subunit, and the gene encoding the α subunit comprises a DNA selected from the group consisting of:

(a) a DNA comprising the nucleotide sequence of SEQ ID NO: 1, (b) a DNA that is able to hybridize with a sequence complementary to the nucleotide sequence of SEQ ID NO: 1, or a probe that can be prepared from the sequence, under stringent conditions, and encodes a polypeptide that has α-ketoglutarate synthase activity when complexed with the β subunit, (c) a DNA comprising the nucleotide sequence of SEQ ID NO: 57, and (d) a DNA that is able to hybridize with a sequence complementary to the nucleotide sequence of SEQ ID NO: 57, or a probe that can be prepared from the sequence, under stringent conditions, and encodes a polypeptide that has α-ketoglutarate synthase activity when complexed with the α subunit, and the gene encoding the β subunit comprises a DNA selected from the group consisting of:

(e) a DNA comprising the nucleotide sequence of SEQ ID NO: 3, (f) a DNA that is able to hybridize with a sequence complementary to the nucleotide sequence of SEQ ID NO: 3, or a probe that can be prepared from the sequence, under stringent conditions, and encodes a polypeptide that has α-ketoglutarate synthase activity when complexed with the α subunit, (g) a DNA comprising the nucleotide sequence of SEQ ID NO: 59, and (h) a DNA that is able to hybridize with a sequence complementary to the nucleotide sequence of SEQ ID NO: 59, or a probe that can be prepared from the sequence, under stringent conditions, and encodes a polypeptide that has α-ketoglutarate synthase activity when complexed with the α subunit.

It is a further aspect of the present invention to provide the microorganism as described above, which has been modified to increase ferredoxin NADP$^+$ reductase activity.

It is a further aspect of the present invention to provide the microorganism as described above, which has been modified to increase pyruvate synthase activity.

It is a further aspect of the present invention to provide the microorganism as described above, which has been modified to increase production of ferredoxin or flavodoxin.

It is a further aspect of the present invention to provide the microorganism as described above, which has been modified to decrease α-ketoglutarate dehydrogenase activity.

It is a further aspect of the present invention to provide the microorganism as described above, which is a bacterium belonging to a genus selected from the group consisting of *Escherichia*, *Enterobacter*, *Pantoea*, *Klebsiella*, and *Serratia*.

It is a further aspect of the present invention to provide the microorganism as described above, which is a coryneform bacterium.

It is a further aspect of the present invention to provide a method for producing an L-amino acid comprising culturing the microorganism as described above in a medium to produce and accumulate an L-amino acids selected from the group consisting of L-glutamic acid, L-glutamine, L-proline, L-ornithine, L-citrulline, L-arginine and combinations thereof in the medium or the cells of the microorganism, and collecting the L-amino acid from the medium or the cells.

It is a further aspect of the present invention to provide the method as described above, wherein the microorganism is cultured under aerobic conditions.

It is a further aspect of the present invention to provide the method as described above, wherein the medium contains carbonate ions, bicarbonate ions, or carbon dioxide, and the microorganism is cultured under anaerobic or microaerobic conditions.

DETAILED DESCRIPTION OF EXEMPLARY EMBODIMENTS

Hereafter, the presently disclosed subject matter will be explained in detail.

<1> Microorganism in Accordance with the Presently Disclosed Subject Matter

A microorganism in accordance with the presently disclosed subject matter can be a microorganism which is able to produce an L-amino acid such as L-glutamic acid, L-glutamine, L-proline, L-ornithine, L-citrulline, and L-arginine, and can be modified to increase α-ketoglutarate synthase activity.

In accordance with the presently disclosed subject matter, the "L-amino acid" means L-glutamic acid, L-glutamine, L-proline, L-ornithine, L-citrulline, or L-arginine, unless specifically mentioned. These amino acids are also called amino acids of the L-glutamic acid family which can include L-glutamic acid and amino acids which can be biosynthesized from L-glutamic acid as a precursor.

The phrase "ability to produce L-amino acid" refers to the ability to produce L-amino acid and cause accumulation of L-amino acid in the cells of the microorganism in accordance with the presently disclosed subject matter or a medium to such a degree that L-amino acid can be collected from the cells or medium when the bacterium is cultured in the medium. The amino acid produced by the bacterium can be one amino acid or two or more amino acids. The microorganism which is able to produce L-amino acid can be a bacterium which has inherently the ability, or can be a bacterium to which is imparted the ability by modifying the bacterium using mutagenesis or recombinant DNA techniques, or by introducing the gene in accordance with the presently disclosed subject matter to the bacterium.

Furthermore, the phrase "increase the activity of α-ketoglutarate synthase" means both increasing the activity of the enzyme in a microorganism inherently having α-ketoglutarate synthase, and imparting the activity of the enzyme to a microorganism not having the α-ketoglutarate synthase.

<1-1> Impartation of L-Amino Acid Producing Ability

A microorganism in accordance with the presently disclosed subject matter can be obtained from a microorganism which is able to produce L-amino acid as a parent strain by modifying it so that the activity of α-ketoglutarate synthase can be increased. A microorganism in accordance with the presently disclosed subject matter can also be obtained from a microorganism which has been modified so that the activity of α-ketoglutarate synthase can be increased by imparting an L-amino acid producing ability to it or enhancing an L-amino acid producing ability thereof.

Methods for imparting L-amino acid producing ability to a microorganism and microorganisms imparted with an L-amino acid producing ability, which can be used in accordance with the presently disclosed subject matter, will be exemplified below. However, so long as a method that can impart an L-amino acid producing ability or a microorganism having an L-amino acid producing ability is chosen, the methods and microorganisms are not limited to these.

Examples of the microorganism used in accordance with the presently disclosed subject matter can include bacteria, for example, enterobacteria belonging to γ-proteobacteria of the genus *Escherichia, Enterobacter, Pantoea, Klebsiella, Serratia, Erwinia, Salmonella, Morganella*, or the like, so-called coryneform bacteria belonging to the genus *Brevibacterium, Corynebacterium* or *Microbacterium*, microorganisms belonging to the genus *Alicyclobacillus, Bacillus, Saccharomyces*, or the like. For the γ-proteobacteria, those classified according to the classification disclosed in NCBI (National Center for Biotechnology Information) Taxonomy Database (http://www.ncbi.nlm.nih.gov/Taxonomy/Browser/wwwtax.cgi?mode=Undef&id=1236&1v1=3& p=mapview&p=has_linkout&p=blast_url&p=genome_ blast&lin=f&keep=1&srchmode=1&unlock) can be used.

Examples of *Escherichia* bacteria can include *Escherichia coli* and so forth. When *Escherichia coli* strains are bred using a genetic engineering technique, the *E. coli* K12 strain and derivatives thereof, the *Escherichia coli* MG1655 strain (ATCC No. 47076) and W3110 strain (ATCC No. 27325) can be used. The *Escherichia coli* K12 strain was isolated at Stanford University in 1922. This strain is a lysogenic bacterium of λ phage and has the F-factor. This strain is a highly versatile strain from which genetic recombinants can be constructed by conjugation or the like. Furthermore, the genomic sequence of the *Escherichia coli* K12 strain has already been determined, and the gene information thereof can also be used freely. The *Escherichia coli* K12 strain and derivatives thereof are available from American Type Culture Collection (ATCC, Address: P.O. Box 1549, Manassas, Va. 20108, United States of America).

In particular, bacteria belonging to the genera *Pantoea, Erwinia*, and *Enterobacter* are classified as γ-proteobacteria, and they are taxonomically very close to one another (Harada H. and Ishikawa H. 1997. J. Gen. Appl. Microbiol. 43:355-361; Kwon S. W. et al. 1997. Int. J. Syst. Bacteriol. 47:1061-1067). In recent years, some bacteria belonging to the genus *Enterobacter* were reclassified as *Pantoea agglomerans, Pantoea dispersa*, or the like, on the basis of DNA-DNA hybridization analysis etc. (Gavini, F. et al. 1989. Int. J. Syst. Bacteriol. 39:337-345). Furthermore, some bacteria belonging to the genus *Erwinia* were re-classified as *Pantoea ananas* or *Pantoea stewartii* (refer to Mergaert, J. et al. 1993. Int. J. Syst. Bacteriol. 43:162-173).

Examples of the *Enterobacter* bacteria can include, but are not limited to, *Enterobacter agglomerans, Enterobacter aerogenes*, and so forth. Specifically, the strains exemplified in European Patent Publication No. 952221 can be used. Typical strains of *Enterobacter* bacteria can include *Enterobacter aerogenes* ATCC 12287 strain.

Typical strains of the *Pantoea* bacteria can include *Pantoea ananatis, Pantoea stewartii, Pantoea agglomerans*, and *Pantoea citrea*. Specific examples can include the following strains:

*Pantoea ananatis* AJ13355 (FERM BP-6614, European Patent Publication No. 0952221)

*Pantoea ananatis* AJ13356 (FERM BP-6615, European Patent Publication No. 0952221)

Although these strains are described as *Enterobacter agglomerans* in European Patent Publication No. 0952221, they are currently classified as *Pantoea ananatis* on the basis of nucleotide sequence analysis of 16S rRNA etc., as described above.

Examples of the *Erwinia* bacteria can include, but are not limited to, *Erwinia amylovora* and *Erwinia carotovora*, and examples of the *Klebsiella* bacteria can include *Klebsiella planticola*. Specific examples can include the following strains:

*Erwinia amylovora* ATCC 15580;

*Erwinia carotovora* ATCC 15713;

*Klebsiella planticola* AJ13399 (FERM BP-6600, European Patent Publication No. 955368); and

*Klebsiella planticola* AJ13410 (FERM BP-6617, European Patent Publication No. 955368).

The coryneform bacteria can be a group of microorganisms defined in Bergey's Manual of Determinative Bacteriology, 8th Ed., p. 599, 1974, and can include aerobic, Gram-positive, and nonacid-fast bacilli which are not able to sporulate. These bacteria were previously classified into the genus *Brevibacterium* but have now been united into the genus *Corynebacterium* (Liebl, W. et. al. 1991. Int. J. Syst. Bacteriol. 41:255). Coryneform bacteria also can include bacteria belonging to the genus *Brevibacterium* or *Microbacterium*, which are closely relative to the genus *Corynebacterium*.

Examples of coryneform bacteria that can be used for production of an amino acid of the L-glutamic acid family are listed below:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*

*Brevibacterium thiogenitalis*
*Brevibacterium ammoniagenes* (*Corynebacterium ammoniagenes*)
*Brevibacterium album*
*Brevibacterium cerinum*
*Microbacterium ammoniaphilum*

Specifically, the following strains can be encompassed:
*Corynebacterium thermoaminogenes* AJ12340 (FERM BP-1539)
*Corynebacterium glutamicum* ATCC 13032
*Brevibacterium flavum* (*Corynebacterium glutamicum*) ATCC 13826, ATCC 14067
*Brevibacterium lactofermentum* (*Corynebacterium glutamicum*) ATCC 13665, ATCC 13869
*Brevibacterium ammoniagenes* (*Corynebacterium glutamicum*) ATCC 6871

L-Glutamic Acid Producing Strains

Examples of the method for imparting L-glutamic acid producing ability can include, for example, modifying the microorganism so that expression of a gene encoding an enzyme involved in the L-glutamic acid biosynthesis can be enhanced. Examples of such enzymes which are involved in L-glutamic acid production can include, for example, glutamate dehydrogenase (gdh, henceforth this enzyme will be also referred to as "GDH"), glutamine synthetase (glnA), glutamate synthetase (gltAB), phosphoenolpyruvate carboxylase (ppc), pyruvate carboxylase (pyc), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), trio se phosphate isomerase (tpiA), fructose bisphosphate aldolase (fbp), phosphofructokinase (pfkA, pfkB), glucose phosphate isomerase (pgi), 6-phosphogluconate dehydratase (edd), 2-keto-3-deoxy-6-phosphogluconate aldolase (eda), transhydrogenase, and so forth. Shown in the parentheses after the names of the enzymes are the names of the genes. The same shall apply hereafter.

Methods for modifying microorganisms so that expression of a gene encoding an enzyme involved in the L-glutamic acid biosynthesis can be enhanced will be explained below.

The first method can include increasing the copy number of a target gene. For example, the copy number of the target gene can be increased by cloning the gene on an appropriate plasmid and transforming a host microorganism with the obtained plasmid. When the nucleotide sequence of the target gene has already been elucidated for, for example, *Escherichia* bacteria or *Corynebacterium* bacteria, the gene can be obtained by synthesizing primers based on the nucleotide sequence, and performing PCR (polymerase chain reaction, refer to White, T. J. et al. 1989. Trends Genet. 5:185-189) with them using genomic DNA as a template. For glutamate dehydrogenase, the *Escherichia coli* gdhA gene (Vallea F. et al. 1984. Gene 27:193-199) and the *Corynebacterium glutamicum* gdh gene (Bormann, E. R. et al. 1992. Mol. Microbiol. 6:317-326) are known. For phosphoenolpyruvate carboxylase, the *Escherichia coli* ppc gene (Fujita, N. et al. 1984. J. Biochem. (Tokyo) 95:909-916) and the *Corynebacterium glutamicum* ppc gene (Eikmanns, B. J. et al. 1989. Mol. Gen. Genet. 218:330-339) are known.

The vector used for transformation can be a vector autonomously replicable in a cell of the host microorganism. Examples of vectors autonomously replicable in bacteria of the Enterobacteriaceae can include plasmid vectors pUC19, pUC18, pBR322, RSF1010, pHSG299, pHSG298, pHSG399, pHSG398, pSTV28, pSTV29 (pHSG and pSTV vectors are available from Takara Bio Inc.), pMW119, pMW118, pMW219, pMW218 (pMW vectors are available from Nippon Gene Co., Ltd.) and so forth. Furthermore, vectors for coryneform bacteria can include pAM330 (Japanese Patent Laid-open No. 58-67699), pHM1519 (Japanese Patent Laid-open No. 58-77895), pSFK6 (Japanese Patent Laid-open No. 2000-262288), pVK7 (USP2003-0175912A), pAJ655, pAJ611, pAJ1844 (Japanese Patent Laid-open No. 58-192900), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491) and so forth. Moreover, if a DNA fragment having an ability to make a plasmid autonomously replicable in a coryneform bacterium is cut from these vectors and inserted into the aforementioned vectors for *Escherichia coli*, they can be used as a so-called shuttle vector which is autonomously replicable in both of *Escherichia coli* and coryneform bacteria. In addition, a phage DNA can also be used as the vector instead of a plasmid.

Examples of transformation methods can include treating recipient cells with calcium chloride so to increase permeability of the DNA, which has been reported for *Escherichia coli* K-12 (Mandel, M. and Higa, A. 1970. J. Mol. Biol. 53:159-162), and preparing competent cells from cells which are at the growth phase, followed by transformation with DNA, which has been reported for *Bacillus subtilis* (Duncan, C. H. et all 1977. Gene 1:153-167). Alternatively, a method of making DNA-recipient cells into protoplasts or spheroplasts, which can easily take up recombinant DNA, followed by introducing the recombinant DNA into the cells, which is known to be applicable to *Bacillus subtilis*, actinomycetes and yeasts (Chang, S. and Choen, S. N. 1979. Molec. Gen. Genet. 168:111-115; Bibb, M. J. et al. 1978. Nature, 274:398-400; Hinnen, A. et al. 1978. Proc. Natl. Sci., USA, 75:1929-1933), can also be employed. In addition, transformation of microorganisms can also be performed by the electric pulse method (Japanese Patent Laid-open No. 2-207791).

Increasing the copy number of a target gene can also be achieved by introducing multiple copies of the gene into the genomic DNA of the microorganism. Introducing multiple copies of the operon into the genomic DNA of the microorganism can be performed by homologous recombination (Miller I, J. H. Experiments in Molecular Genetics, 1972, Cold Spring Harbor Laboratory) using a sequence whose multiple copies exist as targets in the genomic DNA. Sequences having multiple copies in the genomic DNA can include, but are not limited to, repetitive DNA, or inverted repeats existing at the end of a transposable element. Also, as disclosed in Japanese Patent Laid-open No. 2-109985, it is possible to incorporate the target gene into a transposon, and allow it to be transferred to introduce multiple copies of the gene into the genomic DNA. Introduction of multiple copies of a gene into a bacterial chromosome can be also achieved by the method using Mu phage (Japanese Patent Laid-open No. 2-109985), or the like. Transfer of a target gene to a chromosome can be confirmed by Southern hybridization using a part of the gene as a probe.

The copy number is not particularly limited so long as activity of the target gene product can be enhanced. An exemplary embodiment in accordance with the presently disclosed subject matter can be a copy number of at least two.

A second exemplary method can include enhancing expression of a target gene by replacing an expression regulatory sequence of the target gene such as promoter on the genomic DNA or plasmid with a promoter which has an appropriate strength. For example, the thr promoter, lac promoter, trp promoter, trc promoter, pL promoter, tac promoter, etc., are known as frequently used promoters. Examples of promoters with high expression activity in coryneform bacteria can include promoters of the elongation factor Tu (EF-Tu) gene, tuf (SEQ ID NO: 77), promoters of genes that encode cochaperonin GroES-chaperonin GroEL, thioredoxin reductase, phosphoglycerate mutase, glyceraldehyde-3-phosphate dehydrogenase, and the like (WO2006/028063, EP1697525). Examples of strong promoters and methods for evaluating the strength of promoters are described in an article by Goldstein and Doi (Goldstein, M. A. and Doi R. H. 1995. Biotechnol. Annu. Rev. 1:105-128), etc.

Moreover, it is also possible to substitute several nucleotides in a promoter region of a gene, so that the promoter has an appropriate strength, as disclosed in International Patent Publication WO00/18935. Substitution of the expression regulatory sequence can be performed, for example, in the same manner as in gene substitution using a temperature sensitive plasmid. Examples of vectors having a temperature sensitive replication origin which can be used for *Escherichia coli* or *Pantoea ananatis* can include, for example, plasmid pMAN997 described in International Publication WO99/03988, its derivative, and so forth. Furthermore, substitution of an expression regulatory sequence can also be performed by methods which employ linear DNA, such as a method called "Red-driven integration" using Red recombinase of λ phage (Datsenko, K. A. and Wanner, B. L. 2000. Proc. Natl. Acad. Sci. USA. 97:6640-6645), a method combining the Red-driven integration method and the λ phage excisive system (Cho, E. H. et al. 2002. J. Bacteriol. 184:5200-5203) (WO2005/010175), and so forth. The modification of an expression regulatory sequence can be combined with increasing the gene copy number.

Furthermore, it is known that substitution of several nucleotides in a spacer between the ribosome binding site (RBS) and the start codon, and particularly, the sequences immediately upstream of the start codon profoundly affect the mRNA translatability. Translation can be enhanced by modifying these sequences.

Examples of microorganisms modified so that expression of a gene which participates in L-glutamic acid production is enhanced by the aforementioned methods can include those described in International Patent Publication WO99/07853, European Patent No. 1352966, and so forth.

When a target gene is introduced into the aforementioned plasmid or chromosome, any promoter can be used for expression of the gene so long as a promoter that functions in the microorganism used is chosen. The promoter can be the native promoter of the gene, or a modified promoter. Expression of a gene can also be controlled by suitably choosing a promoter that potently functions in the chosen microorganism, or by approximating −35 and −10 regions of a promoter close to the consensus sequence. Microorganisms modified by the methods described above so that expression of glutamate dehydrogenase gene can be enhanced are described in International Patent Publication WO00/18935, European Patent Publication No. 1010755, and so forth.

The method for enhancing expression of a gene described above can also be applied to the gene encoding α-ketoglutarate synthase described later.

A modification for imparting an ability to produce L-glutamic acid can also be performed by decreasing or eliminating an activity of an enzyme that catalyzes synthesis of a compound other than L-glutamic acid by branching off from the L-glutamic acid biosynthesis pathway. Examples of such enzymes can include α-ketoglutarate dehydrogenase, isocitrate lyase, acetate kinase, acetohydroxy acid synthase, acetolactate synthase, formate acetyltransferase, lactate dehydrogenase, glutamate decarboxylase, 1-pyrroline-5-carboxylate dehydrogenase, and so forth. As an exemplary embodiment, α-ketoglutarate dehydrogenase activity among these enzymes can be reduced or eliminated.

In order to reduce or eliminate the activities of the aforementioned enzymes, mutations for reducing or eliminating intracellular activities of the enzymes can be introduced into genes of the aforementioned enzymes by a conventional mutagenesis or genetic engineering techniques. Examples of the mutagenesis can include, for example, X-ray or ultraviolet ray irradiation, treatment with a mutagen such as N-methyl-N'-nitro-N-nitrosoguanidine, and so forth. The site on the gene where the mutation is introduced can be in the coding region encoding an enzyme protein or an expression control region such as a promoter. Examples of the genetic engineering techniques can include genetic recombination, transduction, cell fusion and so forth.

A decrease or elimination of the intracellular activity of the objective enzyme and the degree of decrease can be confirmed by measuring the enzyme activity in a cell extract or a purified fraction thereof obtained from a candidate strain, and comparing it with that of a wild-type strain. For example, α-ketoglutarate dehydrogenase activity can be measured by the method of Reed and Mukherjee (Reed, L. J. and Mukherjee, B. B. 1969. Methods in Enzymology 13:55-61).

Methods for eliminating or reducing α-ketoglutarate dehydrogenase activity in *Escherichia* bacteria are disclosed in Japanese Patent Laid-open Nos. 5-244970, 7-203980 and so forth. Methods for eliminating or reducing α-ketoglutarate dehydrogenase activity in coryneform bacteria are disclosed in International Patent Publication WO95/34672. Furthermore, such methods for *Enterobacter* bacteria are disclosed in Japanese Patent Laid-open No. 2001-333769.

For example, α-ketoglutarate dehydrogenase activity can be reduced by modifying the sucA (odhA) gene which encodes the E1o subunit of the enzyme. Examples of strains of which α-ketoglutarate dehydrogenase activity is reduced can include the following strains:

*Brevibacterium lactofermentum* ΔS (WO95/34672);
*Brevibacterium lactofermentum* AJ12821 (FERM BP-4172; FR9401748);
*Brevibacterium flavum* AJ12822 (FERM BP-4173; FR9401748);
*Corynebacterium glutamicum* AJ12823 (FERM BP-4174; FR9401748);
*Corynebacterium glutamicum* ATCC 13869, OAGN, OA2-2, OAGN2-2 (WO2006/028298);
*E. coli* AJ12624 (FERM BP-3853);
*E. coli* AJ12628 (FERM BP-3854);
*E. coli* AJ12949 (FERM BP-4881);
*Pantoea ananatis* AJ13601 (FERM BP-7207, EP1078989A);
*Pantoea ananatis* AJ13356 (FERM BP-6615, U.S. Pat. No. 6,331,419);
*Pantoea ananatis* SC17sucA (FERM BP-8646, WO2005/085419); and
*Klebsiella planticola* AJ13410 strain (FERM BP-6617, U.S. Pat. No. 6,197,559).

An example of L-glutamic acid producing strain of *Pantoea* can include *Pantoea ananatis* AJ13355 strain. This strain was isolated from soil in Iwata-shi, Shizuoka, Japan as a strain that can proliferate in a medium containing L-glutamic acid and a carbon source at low pH.

The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and received an accession number of FERM P-16644. It was then converted to an international deposit under the provisions of Budapest Treaty on Jan. 11, 1999 and received an accession number of FERM BP-6614. The above strain was identified as *Enterobacter agglomerans* when it was isolated and deposited as the *Enterobacter agglomerans* AJ13355 strain. However, it was recently re-classified as *Pantoea ananatis* on the basis of nucleotide sequencing of 16S rRNA and so forth.

Furthermore, examples of L-glutamic acid producing *Pantoea ananatis* strains can include bacteria belonging to the genus *Pantoea* in which α-ketoglutarate dehydrogenase (αKGDH) activity is eliminated or reduced. Examples of such strains can include the AJ13356 strain (U.S. Pat. No. 6,331,419) which corresponds to the AJ13355 strain in which the αKGDH-E1 subunit gene (sucA) is deleted, and the SC17sucA strain (U.S. Pat. No. 6,596,517) which is a sucA gene-deficient strain derived from the SC17 strain and selected as a low phlegm producing mutant. The AJ13356 strain was deposited at the National Institute of Bioscience and Human-Technology, Agency of Industrial Science and Technology, Ministry of International Trade and Industry (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, receiving an accession number of FERM P-16645. Then, the deposit was converted into the international deposit under the provisions of the Budapest Treaty on Jan. 11, 1999, receiving an accession number of FERM BP-6616. Although the above described AJ13355 and AJ13356 strains, and the AJ13601 strain described below were deposited at the aforementioned depository as *Enterobacter agglomerans*, they are referred to as *Pantoea ananatis* in this specification. The SC17sucA strain was assigned a private number of AJ417, and deposited at the National Institute of Advanced Industrial Science and Technology, International Patent Organism Depositary on Feb. 26, 2004, receiving an accession number of FERM BP-08646.

Examples of L-glutamic acid producing *Pantoea ananatis* strains further can include the strains SC17sucA/RSFCPG+pSTVCB, AJ13601, NP106, and NA1. The SC17sucA/RSFCPG+pSTVCB strain was obtained by introducing the plasmid RSFCPG containing the citrate synthase gene (gltA), phosphoenolpyruvate carboxylase gene (ppsA) and the glutamate dehydrogenase gene (gdhA) of *Escherichia coli* and the plasmid pSTVCB containing the citrate synthase gene (gltA) of *Brevibacterium lactofermentum* into the SC17sucA strain. The AJ13601 strain was selected from the SC17sucA/RSFCPG+pSTVCB strain as a strain showing resistance to high concentration of L-glutamic acid under a low pH condition. The NP106 strain corresponds to the AJ13601 strain in which plasmid RSFCPG+pSTVCB is eliminated as described in the examples. The AJ13601 strain was deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Aug. 18, 1999, receiving an accession number FERM P-17516. Then, the deposit was converted into an international deposit under the provisions of the Budapest Treaty on Jul. 6, 2000, receiving an accession number FERM BP-7207.

As the method for imparting L-glutamic acid producing ability to coryneform bacteria, a method of amplifying the yggB gene (NCgl 1221; NP_600492 [gi:19552490]), and a method of introducing a variant yggB gene introduced with a mutation in the coding region (WO2006/070944) can also be employed.

The L-glutamic acid producing ability can also be imparted by amplifying the yhfK gene, which is an L-glutamic acid secretion gene (WO2005/085419).

Examples of other methods for imparting or enhancing L-glutamic acid producing ability can include imparting resistance to an organic acid analogue, respiratory inhibitor or the like and imparting sensitivity to a cell wall synthesis inhibitor. These methods can include, for example, imparting monofluoroacetic acid resistance (Japanese Patent Laid-open No. 50-113209), imparting adenine resistance or thymine resistance (Japanese Patent Laid-open No. 57-065198), attenuating urease (Japanese Patent Laid-open No. 52-038088), imparting malonic acid resistance (Japanese Patent Laid-open No. 52-038088), imparting resistance to benzopyrons or naphthoquinones (Japanese Patent Laid-open No. 56-1889), imparting HOQNO resistance (Japanese Patent Laid-open No. 56-140895), imparting α-ketomalonic acid resistance (Japanese Patent Laid-open No. 57-2689), imparting guanidine resistance (Japanese Patent Laid-open No. 56-35981), imparting sensitivity to penicillin (Japanese Patent Laid-open No. 4-88994), and so forth.

Examples of such resistant bacteria can include the following strains:

*Brevibacterium flavum* AJ3949 (FERM BP-2632, refer to Japanese Patent Laid-open No. 50-113209);

*Corynebacterium glutamicum* AJ11628 (FERM P-5736, refer to Japanese Patent Laid-open No. 57-065198);

*Brevibacterium flavum* AJ11355 (FERM P-5007, refer to Japanese Patent Laid-open No. 56-1889);

*Corynebacterium glutamicum* AJ11368 (FERM P-5020, refer to Japanese Patent Laid-open No. 56-1889);

*Brevibacterium flavum* AJ11217 (FERM P-4318, refer to Japanese Patent Laid-open No. 57-2689);

*Corynebacterium glutamicum* AJ11218 (FERM P-4319, refer to Japanese Patent Laid-open No. 57-2689);

*Brevibacterium flavum* AJ11564 (FERM P-5472, refer to Japanese Patent Laid-open No. 56-140895);

*Brevibacterium flavum* AJ11439 (FERM P-5136, refer to Japanese Patent Laid-open No. 56-35981);

*Corynebacterium glutamicum* H7684 (FERM BP-3004, refer to Japanese Patent Laid-open No. 04-88994);

*Brevibacterium lactofermentum* AJ11426 (FERM P-5123, refer to Japanese Patent Laid-open No. 56-048890);

*Corynebacterium glutamicum* AJ11440 (FERM P-5137, refer to Japanese Patent Laid-open No. 56-048890); and

*Brevibacterium lactofermentum* AJ11796 (FERM P-6402, refer to Japanese Patent Laid-open No. 58-158192).

L-Glutamine Producing Bacteria

Examples of microorganisms having L-glutamine producing ability can include bacteria in which glutamate dehydrogenase activity is enhanced, bacteria in which glutamine synthetase (glnA) activity is enhanced, and bacteria in which glutaminase gene is disrupted (European Patent Publication Nos. 1229121 and 1424398). Enhancement of the glutamine synthetase activity also can be attained by disrupting a gene encoding glutamine adenylyltransferase (glnE) or a gene encoding PII control protein (glnB) (EP1229121). Furthermore, a strain belonging to the genus *Escherichia* and having a variant glutamine synthetase in which the tyrosine residue at position 397 is replaced with another amino acid residue also can be exemplified as a L-glutamine producing bacterium (U.S. Patent Application Publication No. 2003/0148474).

The method for imparting or enhancing L-glutamine producing ability can include imparting 6-diazo-5-oxo-norleucine resistance (Japanese Patent Laid-open No. 3-232497), imparting purine analogue resistance and/or methionine sulfoxide resistance (Japanese Patent Laid-open No. 61-202694), imparting α-ketomalonic acid resistance (Japanese Patent Laid-open No. 56-151495), and so forth. Specific examples of coryneform bacteria having L-glutamine-producing ability can include the following strains:

*Brevibacterium flavum* AJ11573 (FERM P-5492, see Japanese Patent Laid-open No. 56-151495);
  *Brevibacterium flavum* AJ12210 (FERM P-8123, see Japanese Patent Laid-open No. 61-202694); and
  *Brevibacterium flavum* AJ12212 (FERM P-8123, see Japanese Patent Laid-open No. 61-202694).

L-Proline Producing Bacteria

Examples of microorganisms having L-proline producing ability can include, for example, bacteria having γ-glutamyl kinase of which feedback inhibition by L-proline is desensitized and bacteria of which the L-proline decomposition system is attenuated. The method to modify bacteria using a DNA encoding γ-glutamyl kinase of which feedback inhibition by L-proline is desensitized is disclosed in Dandekar and Uratsu (J. Bacteriol., 170, 12:5943-5945, 1988). Furthermore, examples of the methods for obtaining a bacterium in which the L-proline decomposition system is attenuated can include introducing a mutation into a proline dehydrogenase gene to reduce the enzymatic activity. Examples of bacteria having L-proline producing ability can include the *Escherichia coli* NRRL B-12403 strain and NRRL B-12404 strain (British Patent No. 2075056), *Escherichia coli* VKPM B-8012 strain (U.S. Patent Application Publication No. 2002/0058315), and strains having the mutant plasmid disclosed in German Patent No. 3127361 or the mutant plasmid disclosed in the reference of Bloom F. R. et al. (The 15th Miami Winter Symposium, 1983, p. 34).

Furthermore, exemplary microorganisms having L-proline producing ability also can include the *Escherichia coli* 702 strain (VKPMB-8011), which is resistant to 3,4-dehydroxyproline and azetidine-2-carboxylate, 702ilvA strain (VKPMB-8012 strain), which is an ilvA-deficient strain of the 702 strain, *E. coli* strains in which the activity of a protein encoded by the b2682, b2683, b1242 or b3434 gene is enhanced (Japanese Patent Laid-open No. 2002-300874), and so forth.

L-Arginine Producing Bacteria

Examples of bacteria which produce L-arginine can include, but are not limited to, *E. coli* mutants having resistance to α-methylmethionine, p-fluorophenylalanine, D-arginine, arginine hydroxamate, S-(2-aminoethyl)-cysteine, α-methylserine, β-2-thienylalanine, or sulfaguanidine (JP 56-106598A). *E. coli* strain 237 (Russian patent application No. 2000117677) harboring mutant N-acetylglutamate synthetase which is desensitized to feedback inhibition by L-arginine and has high enzymatic activity is also an exemplary L-arginine producing strain. The strain 237 was deposited at the VKPM (the Russian National Collection of Industrial Microorganisms, Russia, 117545 Moscow, 1 Dorozhny proezd, 1) on Apr. 10, 2000 under the accession number VKPM B-7925. It was then converted to an international deposit under the provisions of Budapest Treaty on May 18, 2001. The *E. coli* strain 382 (JP2002-017342A) derived from the strain 237, which has increased activity to utilize acetic acid also can be used. *Escherichia coli* strain 382 was deposited at the VKPM (the Russian National Collection of Industrial Microorganisms, Russia, 117545 Moscow, 1 Dorozhny proezd, 1) on Apr. 10, 2000 under the accession number VKPM B-7926.

Examples of bacteria to which L-arginine producing ability can be imparted can include strains in which expression of one or more genes encoding an L-arginine biosynthetic enzyme are enhanced. Examples of the L-arginine biosynthetic enzymes can include N-acetylglutamate synthase (argA), N-acetylglutamyl phosphate reductase (argC), ornithine acetyl transferase (argJ), N-acetylglutamate kinase (argB), acetylornithine transaminase (argD), acetylornitine deacetylase (argE), ornithine carbamoyl transferase (argF), argininosuccinic acid synthetase (argG), argininosuccinic acid lyase (argH), and carbamoyl phosphate synthetase (carAB). As for N-acetylglutamate synthase (argA), as an exemplary embodiment, is it possible to use a mutant gene encoding the enzyme in which the amino acid sequence corresponding to positions 15 to 19 is replaced and feedback inhibition by L-arginine is desensitized (European Patent Publication No. 1170361).

L-Arginine producing coryneform bacteria are not specifically limited so long as the bacterium is able to produce L-arginine. Examples of such coryneform bacteria can include, but are not limited to, wild-type strains of coryneform bacteria; a bacterium which is resistant to a drug such as a sulfa drug, 2-thiazolealanine, α-amino-β-hydroxyvaleric acid or the like; a bacterium which has auxotrophy for L-histidine, L-proline, L-threonine, L-isoleucine, L-methionine or L-tryptophan in addition to resistance to 2-thiazolealanine (Japanese Patent Laid-open No. 54-44096); a bacterium which is resistant to ketomalonic acid, fluoromalonic acid or monofluoroacetic acid (Japanese Patent Laid-open No. 57-18989); a bacterium which is resistant to argininol (Japanese Patent Laid-open No. 62-24075); a bacterium which is resistant to X-guanidine (X represents a derivative of fatty acid or aliphatic chain, Japanese Patent Laid-open No. 2-186995), and the like.

Additionally, L-arginine producing coryneform bacteria can be bred to be resistant to 5-azauracil, 6-azauracil, 2-thiouracil, 5-fluorouracil, 5-bromouracil, 5-azacytosine, 6-azacytosine and so forth; to be resistant to arginine hydroxamate and 2-thiouracil; to be resistant to arginine hydroxamate and 6-azauracil (Japanese Patent Laid-open No. 49-126819); to be resistant to a histidine analogue or tryptophan analogue (Japanese Patent Laid-open No. 52-114092); to be auxotrophic for at least one of methionine, histidine, threonine, proline, isoleucine, lysine, adenine, guanine or uracil (or uracil precursor) (Japanese Patent Laid-open No. 52-99289); to be resistant to arginine hydroxamate (Japanese Patent Publication No. 51-6754); to be auxotrophic for succinic acid or resistant to a nucleic acid base analogue (Japanese Patent Laid-open No. 58-9692); to be unable to metabolize arginine and to be resistant to an arginine antagonist and canavanine and to be auxotorophic for lysine (Japanese Patent Laid-open No. 52-8729); to be resistant to arginine, arginine hydroxamate, homoarginine, D-arginine and canavanine, or resistant to arginine hydroxamate and 6-azauracil (Japanese Patent Laid-open No. 53-143288); to be resistant to canavanine (Japanese Patent Laid-open No. 53-3586) and so forth.

Examples of L-arginine producing coryneform bacteria can include the following strains:
  *Brevibacterium flavum* AJ11169 (FERM BP-6892);
  *Brevibacterium lactofermentum* AJ12092 (FERM BP-6906);
  *Brevibacterium flavum* AJ11336 (FERM BP-6893);
  *Brevibacterium flavum* AJ11345 (FERM BP-6894), and
  *Brevibacterium lactofermentum* AJ12430 (FERM BP-2228).

Furthermore, the strain deficient in the arginine repressor, ArgR (U.S. Patent Application Publication No. 2002/

0045223) or the strain in which intracellular glutamine synthetase activity is increased (U.S. Patent Application No. 2005/0014236) can be used.

The biosynthetic pathways of L-citrulline and L-ornithine are common to that of L-arginine, and abilities to produce them can be imparted by increasing enzymatic activities of N-acetylglutamate synthase (argA), N-acetylglutamyl phosphate reductase (argC), ornithine acetyltransferase (argJ), N-acetylglutamate kinase (argB), acetylornithine transaminase (argD) or acetylornithine deacetylase (argE) (International Patent Publication No. 2006-35831).

Aside from a gene which encodes an inherent biosynthesis enzyme, a gene which is involved in sugar uptake, sugar metabolism (glycolytic system), and energy metabolism can be enhanced in the L-amino acid producing bacteria in accordance with the presently disclosed subject matter.

Examples of the genes involved in sugar metabolism can include genes which encode glycolytic enzymes or proteins which uptake sugar, such as genes encoding glucose-6-phosphate isomerase (pgi; WO01/02542), phosphoenolpyruvate synthase (pps; EP877090), phosphoglucomutase (pgm; WO03/04598), fructose-bisphosphate aldolase (fba; WO03/04664), pyruvate kinase (pykF; WO03/008609), transaldolase (talB; WO03/008611), fumarase (fum; WO01/02545), phosphoenolpyruvate synthase (pps; EP877090), the non-PTS sucrose uptake systems (csc; EP149911), and sucrose-assimilating genes (scrAB operon; WO90/04636).

Examples of the genes involved in energy metabolism can include the transhydrogenase gene (pntAB; U.S. Pat. No. 5,830,716) and the cytochromoe bo type oxidase gene (cyoABCD; EP1070376).

Furthermore, when glycerol is used as a carbon source, in order to enhance the assimilability of glycerol, expression of the glpR gene can be attenuated (EP1715056), or expression of the glycerol metabolism genes such as glpA, glpB, glpC, glpD, glpE, glpF, glpG, glpK, glpQ, glpT, glpX, tpiA, gldA, dhaK, dhaL, dhaM, dhaR, fsa and talC genes may be enhanced (EP1715055A).

<1-2> Enhancement of α-Ketoglutarate Synthase Activity

A microorganism in accordance with the presently disclosed subject matter can be a microorganism which has L-glutamic acid producing ability and which has been modified to increase the activity of α-ketoglutarate synthase. The phrase "modified to increase the activity of α-ketoglutarate synthase" means that the bacterium has been modified in such a way that the activity of α-ketoglutarate synthase is increased as compared to a parent strain, for example, a wild type strain or an unmodified strain. As described above, when a microorganism does not inherently have α-ketoglutarate synthase activity, a microorganism can be modified so that it has increased α-ketoglutarate synthase activity as compared to an unmodified strain or parent strain.

The "α-ketoglutarate synthase" referred to in presently disclosed subject matter means an enzyme catalyzing a reaction generating α-ketoglutaric acid from succinyl-CoA and $CO_2$ in the presence of an electron donor, for example, ferredoxin (EC 1.2.7.3) as described above. α-ketoglutarate synthase also can be referred to as α-ketoglutarate oxidoreductase, α-ketoglutarate ferredoxin oxidoreductase, 2-oxoglutarate synthase, 2-oxoglutarate oxidoreductase or 2-oxoglutarate ferredoxin oxidoreductase. As the electron donor, ferredoxin or flavodoxin can be used.

Parent strains which can be modified so that α-ketoglutarate synthase activity is increased can be strains which inherently have an endogenous gene encoding α-ketoglutarate synthase. Alternatively, the parent strains can be strains which do not inherently have a gene encoding α-ketoglutarate synthase, but which can be imparted with the activity of the enzyme by introduction of an α-ketoglutarate synthase gene and which shows improved L-glutamic acid producing ability.

The parent strain can be first modified so that the enzymatic activity of α-ketoglutarate synthase is increased, and then imparted with L-glutamic acid producing ability. Alternatively, the parent strain can be first imparted with L-glutamic acid producing ability, and then modified so that the enzymatic activity of α-ketoglutarate synthase is increased. The enhancement of the activity of α-ketoglutarate synthase can be attained by enhancing expression of the gene described above. That is, the enhancement can be based on enhancement of expression of an endogenous α-ketoglutarate synthase gene by modification of an expression control region such as modification of a promoter or the like, or enhancement of expression of an exogenous α-ketoglutarate synthase gene by introduction of a plasmid containing an α-ketoglutarate synthase gene or the like.

Enhancement of α-ketoglutarate synthase activity can be confirmed by preparing crude enzyme solutions from the microorganism before the modification and the microorganism after the modification, and comparing α-ketoglutarate synthase activity of them. The activity of α-ketoglutarate synthase can be measured by, for example, the method of Yun et al. (Yun, N. R. et al. 2001. Biochem. Biophy. Res. Commum. 282:589-594). For example, the activity can be measured using the oxidized methylviologen as an electron acceptor, CoA and a crude enzyme solution and spectroscopically measuring the amount of the reduced methylviologen which is increased by the decarboxylation reaction of α-ketoglutaric acid upon addition of α-ketoglutaric acid. One unit (U) of the enzymatic activity is defined as an activity of reducing 1 μmol of methylviologen per 1 minute. The degree of the enhancement of α-ketoglutarate synthase activity is not particularly limited so long as it increases as compared to that of a wild-type strain. In an exemplary embodiment in accordance with the presently disclosed subject matter where the parent strain has α-ketoglutarate synthase activity, the activity can increase 1.5 times or more as compared to that of the parent strain. In other exemplary embodiments the increase can be 2 times or more, or 3 times or more, as compared to that of the parent strain. When the parent strain does not have α-ketoglutarate synthase activity, although it is sufficient that α-ketoglutarate synthase is produced by the introduction of the α-ketoglutarate synthase gene, the modification can be performed to such an extent that the enzymatic activity can be measured, and the activity can be 0.001 U or more in one exemplary embodiment, 0.005 U or more in another exemplary embodiment, or 0.01 U or more in yet another exemplary embodiment, per mg of the cellular protein.

As the gene encoding α-ketoglutarate synthase, α-ketoglutarate synthase genes of *Chlorobium, Desulfobacter, Aquifex, Hydrogenobacter, Thermoproteus* or *Pyrobaculum* bacteria, which are bacteria having the reductive TCA cycle or homologues thereof can be used. Specific examples can include α-ketoglutarate synthase genes of *Chlorobium tepidum, Hydrogenobacter thermophilus*, and so forth. A gene which is thought to be a α-ketoglutarate synthase gene is present in *Blastopirellula marina* belonging to the Order Planctomycetes, which is a marine bacterium (Schlesner, H. et al. 2004. Int. J. Syst. Evol. Microbiol. 54: 1567-1580). Moreover, the genomes of *Sulfurimonas denitrifican* belonging to ε-proteobacteria, which are sulphur-oxidizing bacteria (Brinkhoff, T. et al. 1999. Int. J. Syst. Bacteriol. 49:875-879), methane producing bacteria such as *Methanococcus maripaludis* belonging to archaebacteria (Jones, W. J. et al. Arch.

Microbiol. 1983. 135: 91-97), and the like were determined to include genes with high homologies to the α-ketoglutarate synthase gene. It is possible to select the α-ketoglutarate synthase gene from these exemplary bacteria.

α-Ketoglutarate synthase is known to function as a complex of two or more peptides. The genomic sequence of *Chlorobium tepidum* has already been determined (Genbank Accession No. NC_002932, Eisen, J. A. et al., 2002. Proc. Natl. Acad. Sci. USA 99:9509-9514), and examples of the α-ketoglutarate synthase gene can include the nucleotide sequences of SEQ ID NOS: 1 and 3. SEQ ID NO: 1 is the nucleotide sequence of the α-subunit gene of α-ketoglutarate synthase, which is located at the nucleotide numbers 170164 to 172047 (complementary strand) of the genomic sequence of *Chlorobium tepidum*, and SEQ ID NO: 3 is the nucleotide sequence of β-subunit gene, which is located at the nucleotide numbers 169132 to 170160 (complementary strand) of the genomic sequence of *Chlorobium tepidum*. SEQ ID NO: 2 is the amino acid sequence of α-subunit of α-ketoglutarate synthase (Genbank Accession No. NP_661069), and SEQ ID NO: 4 is the amino acid sequence of the β-subunit of the same (Genbank Accession No. NP_661068). The genomic sequence of *Blastopirellula marina* (Genbank Accession No. AANZ00000000) has been determined (Fuchsman, C. A., and Rocap, G. Appl. Environ. Microbiol. 2006. 72: 6841-6844). Examples of the α-ketoglutarate synthase gene can include the nucleotide sequences shown in SEQ ID NOS: 57 and 59. SEQ ID NO: 57 shows a nucleotide sequence of an α-subunit gene of α-ketoglutarate synthase located at the nucleotide numbers 3180 to 5045 (complementary strand) of the genomic sequence of *Blastopirellula marina*, and SEQ ID NO: 59 shows a nucleotide sequence of a β-subunit gene located at the nucleotide numbers 2089 to 3108 (complementary strand) of the genomic sequence of *Blastopirellula marina*. SEQ ID NO: 58 is the amino acid sequence of the α-subunit of α-ketoglutarate synthase, and SEQ ID NO: 60 is the amino acid sequence of the β-subunit of α-ketoglutarate synthase.

The α-ketoglutarate synthase gene of *Hydrogenobacter thermophilus* (GenBank Accession No. AB046568) has already been cloned (Yun, N. R. et al. 2001. Biochem. Biophy. Res. Commum. 282:589-594), and the α-subunit (Genbank Accession No. BAB21494) and the β-subunit (Genbank Accession No. BAB21495) have been identified. Examples of the gene further can include the α-ketoglutarate synthase gene which can include four genes, HP0588, HP0589, HP0590 and HP0591, located at the nucleotide numbers of 620219 to 623070 of the genomic sequence of *Helicobacter pylori* (GenBank Accession No. NC_00091), and the α-ketoglutarate synthase gene which can include two genes, SSO2815 and SSO2816, located at the nucleotide numbers of 2575303 to 2578105 of the genomic sequence of *Sulfolobus solfataricus* (GenBank Accession No. NC_002754). Furthermore, the α-ketoglutarate synthase gene can be cloned from *Chlorobium, Desulfobacter, Aquifex, Hydrogenobacter, Thermoproteus, Pyrobaculum, Sulfurimonas, Methanococcus* bacteria or the like on the basis of homology to the genes exemplified above.

In an exemplary embodiment in accordance with the presently disclosed subject matter, the genes of α-subunit and β-subunit of the α-ketoglutarate synthase can be those derived from the same organism. However, each of the genes can be derived from different organisms so long as the encoded protein maintains the α-ketoglutarate synthase activity. Exemplary combinations can include an α-subunit including the amino acid sequence of SEQ ID NO: 2 or its conservative variant and a β-subunit including the amino acid sequence of SEQ ID NO: 4 or its conservative variant, and an α-subunit including the amino acid sequence of SEQ ID NO: 58 or its conservative variant and a β-subunit including the amino acid sequence of SEQ ID NO: 60 or its conservative variant. However, the combinations are not limited to these examples. The phrase "conservative variant" will be explained below.

A microorganism in accordance with the presently disclosed subject matter can be a microorganism which has been modified to increase activity for recycling electron donation required for the activity of α-ketoglutarate synthase from the oxidized type into the reduced type as compared to the parent strain (for example, a wild type strain or an unmodified strain), thereby the activity of α-ketoglutarate synthase can be increased. Examples of the activity to recycle the oxidized type of the electron donation into the reduced type can include the activities of ferredoxin $NADP^+$ reductase and pyruvate synthase. Furthermore, a microorganism in accordance with the presently disclosed subject matter can be a microorganism which has been modified so that expression of the α-ketoglutarate synthase gene is increased, in addition to enhancement of the electron donation recycling activity. The aforementioned parent strain can be a strain which inherently has an endogenous gene encoding the electron donation recycling activity. Alternatively, the parent strain can be a strain which does not inherently have a gene encoding the electron donation recycling activity, but which can be imparted with the activity by introduction of a gene encoding the activity, and which shows improved L-glutamic acid producing ability.

The "ferredoxin $NADP^+$ reductase" means an enzyme that reversibly catalyzes the following reaction (EC 1.18.1.2):

Reduced ferredoxin+$NADP^+$→Oxidized ferredoxin+NADP+$H^+$

This reaction is a reversible reaction, and can generate the reduced ferredoxin in the presence NADPH and the oxidized ferredoxin. Ferredoxin is replaceable with flavodoxin, and the enzyme has a function equivalent to that of the enzyme designated flavodoxin $NADP^+$ reductase. Existence of ferredoxin $NADP^+$ reductase is confirmed in a wide variety of organisms ranging from microorganisms to higher organisms (refer to Carrillo, N. and Ceccarelli, E. A. 2004. Eur. J. Biochem. 270:1900-1915; Ceccarelli, E. A. et al. 2004. Biochim. Biophys. Acta. 1698:155-165), and some of the enzymes are also named ferredoxin $NADP^+$ oxidoreductase or NADPH-ferredoxin oxidoreductase.

Enhancement of the ferredoxin $NADP^+$ reductase activity can be confirmed by preparing crude enzyme solutions from the microorganism before and after the modification, and comparing their ferredoxin $NADP^+$ reductase activity. The activity of ferredoxin $NADP^+$ reductase can be measured by, for example, the method of Blaschkowski et al. (Blaschkowski, H. P. et al. 1989. Eur. J. Biochem., 123:563-569). For example, the activity can be measured using ferredoxin as a substrate to spectroscopically measure the decrease of the amount of NADPH. One unit (U) of the enzymatic activity is defined as activity for oxidizing 1 μmol of NADPH per 1 minute. When the parent strain has the ferredoxin $NADP^+$ reductase activity, and the activity of the parent strain is sufficiently high, it is not necessary to enhance the activity. However, in an exemplary embodiment, the enzymatic activity can be increased to a value of 1.5 times or more compared with that of the parent strain. In other exemplary embodiments this enzymatic activity can be increased to a value of 2 times or more, or 3 times or more, compared with that of the parent strain.

Genes encoding the ferredoxin NADP+ reductase are found in many biological species, and any of them showing the activity in the objective L-amino acid producing strain can be used. As for *Escherichia coli*, the fpr gene has been identified as a gene for flavodoxin NADP+ reductase (Bianchi, V. et al. 1993. 175:1590-1595). Moreover, it is known that, in *Pseudomonas putida*, an NADPH-putidaredoxin reductase gene and a putidaredoxin gene are present as an operon (Koga, H. et al. 1989. J. Biochem. (Tokyo), 106:831-836).

Examples of the flavodoxin NADP+ reductase gene of *Escherichia coli* can include the fpr gene which is located at the nucleotide numbers 4111749 to 4112495 (complementary strand) of the genomic sequence of the *Escherichia coli* K-12 strain (Genbank Accession No. U00096) and which has the nucleotide sequence shown in SEQ ID NO: 5. The amino acid sequence of Fpr is shown in SEQ ID NO: 6 (Genbank Accession No. AAC76906). Moreover, a ferredoxin NADP+ reductase gene (Genbank Accession No. BA00036) is also found at the nucleotide numbers 2526234 to 2527211 of the genomic sequence of *Corynebacterium glutamicum* (Genbank Accession No. BAB99777).

The "pyruvate synthase" means an enzyme that reversibly catalyses the following reaction which generates pyruvic acid from acetyl-CoA and $CO_2$ (EC 1.2.7.1):

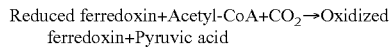

Reduced ferredoxin+Acetyl-CoA+$CO_2$→Oxidized ferredoxin+Pyruvic acid

This reaction is a reversible reaction, and can generate reduced ferredoxin in the presence of pyruvic acid and oxidized ferredoxin. This enzyme also can be designated pyruvate oxidoreductase, pyruvate ferredoxin (flavodoxin) reductase or pyruvate ferredoxin oxidoreductase. By combining this enzymatic activity with α-ketoglutarate synthase activity, it becomes possible to regenerate the reduced ferredoxin consumed by α-ketoglutarate synthase activity by the activity of the reverse reaction of pyruvate synthase.

Enhancement of the pyruvate synthase activity can be confirmed by preparing crude enzyme solutions from the microorganism before and after the enhancement, and comparing their pyruvate synthase activity. The activity of pyruvate synthase can be measured by, for example, the method of Yoon et al. (Yoon, K. S. et al. 1997. Arch. Microbiol. 167:275-279, 1997). The measurement principle is the same as that of the measurement of α-ketoglutarate synthase activity mentioned above, and the activity can be measured by, for example, using pyruvic acid as a substrate and spectroscopically measuring the amount of the methylviologen which is reduced during the decarboxylation reaction of pyruvic acid. One unit (U) of the enzymatic activity is defined as an activity of reducing 1 μmol of methylviologen per 1 minute. In an exemplary embodiment where the parent strain has the pyruvate synthase activity, the activity can increase 1.5 times or more compared with that of the parent strain. In other exemplary embodiments, this increase can be 2 times or more, or 3 times or more, compared with that of the parent strain. When the parent strain does not have the pyruvate synthase activity, although it is sufficient that pyruvate synthase is produced by the introduction of the pyruvate synthase gene, the activity is can be enhanced to such an extent that the enzymatic activity can be measured. In exemplary embodiments, the activity can be 0.001 U/mg or higher, 0.005 U/mg or higher, or 0.01 U/mg or higher.

As the gene encoding the pyruvate synthase, it is possible to use those genes of bacteria having the reductive TCA cycle such as the pyruvate synthase genes of *Chlorobium tepidum* and *Hydrogenobacter thermophilus*.

Specific examples can include a gene having the nucleotide sequence located at the nucleotide numbers 1534432 to 1537989 of the genomic sequence of *Chlorobium tepidum* (Genbank Accession No. NC_002932) and shown in SEQ ID NO: 7, as the pyruvate synthase gene of *Chlorobium tepidum*. The amino acid sequence encoded by this gene is shown in SEQ ID NO: 8 (Genbank Accession No. AAC76906). Furthermore, it is known that the pyruvate synthase of *Hydrogenobacter thermophilus* forms a complex of four subunits, δ-subunit (Genbank Accession No. BAA95604), α-subunit (Genbank Accession No. BAA95605), β-subunit (Genbank Accession No. BAA95606) and γ-subunit (Genbank Accession No. BAA95607) (Ikeda, T. et al. 2006. Biochem. Biophys. Res. Commun. 340:76-82). Examples of the gene further can include the pyruvate synthase gene including four genes, HP1108, HP1109, HP1110 and HP1111, located at the nucleotide numbers of 1170138 to 1173296 of the genomic sequence of *Helicobacter pylori* (GenBank Accession No. NC 000915), and the pyruvate synthase gene including four genes, SSO1208, SSO7412, SSO1207 and SSO1206, identified by the nucleotide numbers of 1047593 to 1044711 in the genomic sequence of *Sulfolobus solfataricus* (GenBank Accession No. NC 002754). Furthermore, the pyruvate synthase gene can be cloned from *Chlorobium, Desulfobacter, Aquifex, Hydrogenobacter, Thermoproteus, Pyrobaculum* bacteria or the like on the basis of homology to the genes exemplified above.

For the activity of α-ketoglutarate synthase, presence of ferredoxin or flavodoxin as an electron donor may be required. Therefore, a microorganism of in accordance with the presently disclosed subject matter can be a microorganism which has been modified so that the activity of α-ketoglutarate synthase is increased by modifying so that the ferredoxin or flavodoxin producing ability can be improved. Furthermore, in addition to modifying so that the activity of α-ketoglutarate synthase, the flavodoxin NADP+ reductase, or pyruvate synthase can be enhanced, it also can be modified so that the ferredoxin or flavodoxin producing ability is increased.

In accordance with the presently disclosed subject matter, the "ferredoxin" refers to a protein containing nonheme iron atoms (Fe) and sulfur atoms, bound with an iron-sulfur cluster called 4Fe-4S, 3Fe-4S or 2Fe-2S cluster, and functioning as a one-electron carrier. The "flavodoxin" refers to a protein containing FMN (flavin-mononucleotide) as a prosthetic group and functioning as a one- or two-electron carrier. Ferredoxin and flavodoxin are described in the reference of McLean et al. (McLean K. J. et al., Biochem. Soc. Trans. 33:796-801, 2005).

The parent strains to be subjected to the modification can be strains which inherently have an endogenous gene encoding ferredoxin or flavodoxin. Alternatively, the parent strains can be strains which do not inherently have a gene encoding ferredoxin or flavodoxin, but which can be imparted with the activity by introduction of a ferredoxin or flavodoxin gene, and which show improved L-glutamic acid producing ability.

Improvement of ferredoxin or flavodoxin producing ability compared with the parent strain such as a wild-type or unmodified strain can be confirmed by, for example, comparing the amount of mRNA for ferredoxin or flavodoxin with that of a wild strain or unmodified strain. Examples of the method for confirming the expression amount include Northern hybridization and RT-PCR (Sambrook, J. et al. 1989. Molecular Cloning A Laboratory Manual/Second Edition, Cold Spring Harbor Laboratory Press, New York). The degree of the increase of the expression is not particularly limited so long as it increases as compared to that of a wild strain or unmodified strain. Exemplary ranges for this increase can include 1.5 times or more, 2 times or more, and 3 times or more, as compared to that of a wild-type strain or unmodified strain.

Improvement of the ferredoxin or flavodoxin producing ability compared with a parent strain, for example, a wild-type strain or an unmodified strain, can be detected by SDS-PAGE, two-dimensional electrophoresis, or Western blotting using antibodies (Sambrook J. et al. 1989. Molecular Cloning A Laboratory Manual/Second Edition, Cold Spring Harbor Laboratory Press, New York). The degree of the improvement of the production is not particularly limited so long as it increases as compared to that of a wild-type strain or unmodified strain. Exemplary ranges for this increase can include 1.5 times or more, 2 times or more, and 3 times or more, as compared to that of a wild strain or unmodified strain.

The activities of ferredoxin and flavodoxin can be measured by adding them to a suitable oxidation-reduction reaction system. For example, a method of reducing produced ferredoxin with ferredoxin $NADP^+$ reductase and quantifying reduction of cytochrome C by the produced reduced ferredoxin is disclosed by Boyer et al. (Boyer, M. E. et al. 2006. Biotechnol. Bioeng. 94:128-138). Furthermore, the activity of flavodoxin can be measured by the same method using flavodoxin $NADP^+$ reductase.

Genes encoding ferredoxin or flavodoxin are widely distributed, and any of those can be used so long as ferredoxin or flavodoxin encoded by the genes can be utilized by α-ketoglutarate synthase and an electron donor recycling system. For example, in *Escherichia coli*, the fdx gene encodes ferredoxin which has a 2Fe-2S cluster (Ta, D. T. and Vickery, L. E. 1992. J. Biol. Chem. 267:11120-11125), and the yfhL gene encodes ferredoxin which has a 4Fe-4S cluster. Furthermore, as the flavodoxin gene, the fldA gene (Osborne C. et al. 1991. J. Bacteriol. 173:1729-1737) and the fldB gene (Gaudu, P. and Weiss, B. 2000. J. Bacteriol. 182:1788-1793) are known. In the genomic sequence of *Corynebacterium glutamicum* (Genbank Accession No. BA00036), the fdx gene (Genbank Accession No. BAB97942) was determined to be at the nucleotide numbers of 562643 to 562963, and the fer gene was determined to be at the nucleotide numbers of 1148953 to 1149270 (Genbank Accession No. BAB98495). Furthermore, in the *Chlorobium tepidum*, many ferredoxin genes exist, and ferredoxin I and ferredoxin II have been identified as ferredoxin genes for the 4Fe-4S type which serves as the electron acceptor of pyruvate synthase (Yoon, K. S. et al. 2001. J. Biol. Chem. 276:44027-44036). Ferredoxin or flavodoxin gene of bacteria having the reductive TCA cycle such as the ferredoxin gene of *Hydrogenobacter thermophilus* can also be used.

Specific examples of the ferredoxin gene of *Escherichia coli* can include the fdx gene located at the nucleotide numbers of 2654770 to 2655105 (complementary strand) of the genomic sequence of the *Escherichia coli* K-12 strain (Genbank Accession No. U00096) and shown in SEQ ID NO: 9, and the yfhL gene located at the nucleotide numbers of 2697685 to 2697945 of the same and shown in SEQ ID NO: 11. The amino acid sequences of Fdx and YfhL are shown in SEQ ID NOS: 10 and 12 (Genbank Accession Nos. AAC75578 and AAC75615, respectively). Examples of the flavodoxin gene of *Escherichia coli* can include the fldA gene located at the nucleotide numbers of 710688 to 710158 (complementary strand) of the genomic sequence of the *Escherichia coli* K-12 strain (Genbank Accession No. U00096) and shown in SEQ ID NO: 13, and the fldB gene located at the nucleotide numbers 3037877 to 3038398 of the same and shown in SEQ ID NO: 15. The amino acid sequences encoded by the fldA gene and the fldB gene are shown in SEQ ID NOS: 14 and 16 (Genbank Accession Nos. AAC73778 and AAC75933, respectively).

Examples of the ferredoxin gene of *Chlorobium tepidum* can include the ferredoxin I gene located at the nucleotide numbers of 1184078 to 1184266 in the genomic sequence of *Chlorobium tepidum* (Genbank Accession No. NC_002932) and shown in SEQ ID NO: 17, and the ferredoxin II gene located at the nucleotide numbers of 1184476 to 1184664 of the same and shown in SEQ ID NO: 19. The amino acid sequences of Ferredoxin I and Ferredoxin II are shown in SEQ ID NOS: 18 and 20 (Genbank Accession Nos. AAM72491 and AAM72490, respectively). Examples further can include the ferredoxin gene of *Hydrogenobacter thermophilus* (Genbank Accession No. BAE02673) and the ferredoxin gene of *Sulfolobus solfataricus* indicated with the nucleotide numbers of 2345414 to 2345728 in the genomic sequence of *Sulfolobus solfataricus*. Furthermore, the gene can be cloned from *Chlorobium*, *Desulfobacter*, *Aquifex*, *Hydrogenobacter*, *Thermoproteus*, *Pyrobaculum* bacteria, or the like, on the basis of homology to the genes exemplified above, or cloned from γ-proteobacteria, such as the genus *Enterobacter*, *Klebsiella*, *Serratia*, *Erwinia* and *Yersinia*, coryneform bacteria such as *Corynebacterium glutamicum* and *Brevibacterium lactofermentum*, *Pseudomonas* bacteria such as *Pseudomonas aeruginosa*, *Mycobacterium* bacteria such as *Mycobacterium tuberculosis*, and so forth.

These genes encoding α-ketoglutarate synthase, ferredoxin NADP+ reductase, pyruvate synthase, ferredoxin, and flavodoxin (henceforth generically called a gene of the presently disclosed subject matter) can be those encoding a conservative variant of the proteins having amino acid sequences including substitutions, deletions, insertions or additions of one or several amino acid residues at one or several positions, so long as the activities of the encoded proteins, i.e., the functions thereof, are not degraded. The number of the "one or several" amino acid residues referred to herein can differ depending on positions in the three-dimensional structure or types of amino acid residues of the proteins. Exemplary ranges can include 1 to 20, 1 to 10, and 1 to 5.

These changes in the variants are conservative mutations that preserve the function of the protein. A conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group.

Specific examples of conservative mutations can include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition or inversion can be a result of a naturally-occurring mutation (mutant or variant) due to an individual difference, or a difference of species of a bacterium harboring the gene of the presently disclosed subject matter.

Furthermore, a gene with substitutions of codons that can be easily used in a host into which a gene of the presently disclosed subject matter is introduced can be used. Similarly, so long as a gene of the presently disclosed subject matter maintains its function, the gene can be extended or shortened at either the N-terminus and/or C-terminus. Exemplary lengths of the extension or shortening can include 50 or less, 20 or less, 10 or less, and 5 or less, in terms of the number of amino acid residues.

A gene encoding such a conservative variant can be obtained by, for example, modifying the nucleotide sequence by site-specific mutagenesis so that amino acid residues of specific sites of the encoded protein includes substitutions, deletions, insertions or additions of amino acid residues. Furthermore, it can also be obtained by conventionally known mutagenesis. Examples of the mutagenesis can include treating a gene of the presently disclosed subject matter with hydroxylamine or the like in vitro, and irradiating ultraviolet to a microorganism such as an *Escherichia* bacterium containing the gene, or treating the microorganism with a mutagen used for usual mutagenesis such as N-methyl-N'-nitro-N-nitrosoguanidine (NTG) or ethyl methanesulfonate (EMS). Moreover, such substitutions, deletions, insertions, additions and inversions of amino acid residues as described above can include those caused by a naturally occurring mutation or variation based on difference of individuals or species of the microorganism containing a gene of the presently disclosed subject matter. Whether these genes encode functional α-ketoglutarate synthase, ferredoxin NADP$^+$ reductase, pyruvate synthase, ferredoxin, or flavodoxin can be confirmed by, for example, introducing each gene into a microorganism, and measuring the activity of each gene product.

A gene in accordance with the presently disclosed subject matter can be a DNA which is able to hybridize with a DNA having any one of the aforementioned nucleotide sequences or a probe prepared from a DNA which has any one of these nucleotide sequences under stringent conditions and which encodes α-ketoglutarate synthase, ferredoxin NADP$^+$ reductase, pyruvate synthase, ferredoxin, or flavodoxin.

The term "stringent conditions" refers to conditions where a so-called specific hybrid is formed and a non-specific hybrid is not formed. It is difficult to clearly define the conditions by numerical value, but examples thereof can include conditions where DNAs having high homology, hybridize with each other and DNAs having homology less than the value do not hybridize with each other; and specifically include conditions corresponding to salt concentration and temperature of washing conditions of typical of Southern hybridization. Exemplary high homology values can include at least 70%, 80%, 90%, and 95% homology. Exemplary conditions of washing temperatures and salt concentrations can include 60° C., 1×SSC, 0.1% SDS; 60° C., 0.1×SSC, 0.1% SDS; and 68° C., 0.1×SSC, 0.1% SDS, where the washing can be performed once, twice or three times. In the specification, the term "homology" can sometimes means "identity".

As a probe, a partial sequence of a gene of the presently disclosed subject matter can also be used. Such a probe can be prepared by PCR using oligonucleotides prepared based on the nucleotide sequence of each gene as primers according to a method well known to a person skilled in the art, and a DNA fragment containing each gene as a template. When a DNA fragment of a length of about 300 bp is used as the probe, the conditions of washing after hybridization can be, for example, 50° C., 2×SSC, and 0.1% SDS.

The aforementioned descriptions concerning the conservative variant also can be applied to the enzymes and genes described above for impartation of L-amino acid producing ability.

The modification for enhancing expression of a gene of the presently disclosed subject matter can be performed in the same manner as that of the method for enhancing expression of a target gene described for the impartation of the L-amino acid producing ability. A gene of the presently disclosed subject matter can be obtained by PCR using a genomic DNA of a microorganism having it as a template.

For example, the α-ketoglutarate synthase gene of *Chlorobium tepidum* can be obtained by PCR using primers prepared on the basis of the nucleotide sequences of SEQ ID NOS: 1 and 3, for example, the primers shown in SEQ ID NOS: 21 and 22, and the genomic DNA of *Chlorobium tepidum* as a template.

The flavodoxin NADP$^+$ reductase gene of *Escherichia coli* can be obtained by PCR using primers prepared on the basis of the nucleotide sequence of SEQ ID NO: 5, for example, the primers shown in SEQ ID NOS: 32 and 33, and the genomic DNA of *Escherichia coli* as a template.

The pyruvate synthase gene of *Chlorobium tepidum* can be obtained by PCR using primers prepared on the basis of the nucleotide sequence of SEQ ID NO: 7, for example, the primers shown in SEQ ID NOS: 23 and 24, and the genomic DNA of *Chlorobium tepidum* as a template.

The ferredoxin gene fdx of *Escherichia coli* can be obtained by PCR using primers prepared on the basis of the nucleotide sequence of SEQ ID NO: 9, for example, the primers shown in SEQ ID NOS: 38 and 39, and the genomic DNA of *Escherichia coli* as a template, and the ferredoxin gene yfhL of the same can be obtained by PCR using primers prepared on the basis of the nucleotide sequence of SEQ ID NO: 11, for example, the primers shown in SEQ ID NOS: 40 and 41, and the genomic DNA of the same as a template.

The flavodoxin gene fldA of *Escherichia coli* can be obtained by PCR using primers prepared on the basis of the nucleotide sequence of SEQ ID NO: 13, for example, the primers shown in SEQ ID NOS: 34 and 35, and the genomic DNA of *Escherichia coli* as a template, and the flavodoxin gene fldB of the same can be obtained by PCR using primers prepared on the basis of the nucleotide sequence of SEQ ID NO: 15, for example, the primers shown in SEQ ID NOS: 36 and 37, and the genomic DNA of *Escherichia coli* as a template.

Furthermore, the ferredoxin I gene of *Chlorobium tepidum* can be obtained by PCR using primers prepared on the basis of the nucleotide sequence of SEQ ID NO: 17, for example, the primers shown in SEQ ID NOS: 25 and 26, and the genomic DNA of *Chlorobium tepidum* as a template.

A gene in accordance with the presently disclosed subject matter from other microorganisms also can be obtained by PCR from the genomic DNA or a genomic DNA library of the chosen microorganism using, as primers, oligonucleotides prepared based on the known sequences of the genes as described above, or of the genes of the chosen microorganism; or hybridization using an oligonucleotide prepared based on the sequence as a probe. A genomic DNA can be prepared from a microorganism that serves as a DNA donor by the method of Saito and Miura (Saito H. and Miura K. 1963. Biochem. Biophys. Acta 72:619-629), Experiment Manual for Biotechnology, edited by The Society for Biotechnology, Japan, p 97-98, Baifukan Co., Ltd., 1992) or the like.

Enhancement of expression of a gene of the presently disclosed subject matter can be attained by increasing the copy number of the gene by performing transformation or homologous recombination or modifying an expression control sequence of the gene in any such manner as described above. Furthermore, enhancement of expression of a gene of the presently disclosed subject matter can also be attained by amplifying an activator which increases expression of the gene, and/or a eliminating or attenuating a regulator which reduce expression of the gene.

When the copy number of the gene is increased, the increased copy number is not particularly limited so long as activity of the product of the target gene can be enhanced. However, when the microorganism inherently has the target gene, the copy number can be 2 or more. Furthermore, when the microorganism does not originally have a gene of the presently disclosed subject matter, the copy number of the gene introduced can be 1, or 2, or more.

When the target substance consists of multiple subunits like α-ketoglutarate synthase, expressions of genes encoding the subunits can be individually enhanced, or can be simultaneously enhanced as a polycistron. Furthermore, when the genes are introduced into a microorganism using a vector, the genes encoding the subunits may be simultaneously carried by a single vector molecule, or can be separately carried by different vector molecules. Also when the genes encoding the subunits are inserted into a chromosome, the genes can be simultaneously inserted into the same site on the chromosome, or can be separately inserted on different sites.

Furthermore, in a microorganism of the presently disclosed subject matter, the α-ketoglutarate dehydrogenase activity can be reduced. Additionally, α-ketoglutarate synthase activity can be enhanced. Such a microorganism can be obtained by transforming a microorganism in which the gene encoding α-ketoglutarate dehydrogenase is disrupted with a recombinant vector containing a gene of the presently disclosed subject matter by, for example, any of the methods described above.

In accordance with the presently disclosed subject matter, the activity of α-ketoglutarate dehydrogenase (henceforth also referred to as "α-KGDH") means an activity of catalyzing the reaction oxidatively decarboxylating α-ketoglutaric acid (2-oxoglutaric acid) to generate succinyl-CoA. The aforementioned reaction can be catalyzed by three kinds of enzymes, α-KGDH (E1o, α-ketoglutarate dehydrogenase, EC:1.2.4.2), dihydrolipoamide S-succinyltransferase (E2o, EC: 2.3.1.61), and dihydrolipoamide dehydrogenase (E3, EC:1.8.1.4). That is, these three kinds of subunits can catalyze the reactions described below, respectively, and the activity for catalyzing a reaction consisting of a combination of these three kinds of reactions is called α-KGDH activity. The activity of α-KGDH can be confirmed by measurement according to the method of Shiio and Ujigawa-Takeda (Shiio I. and Ujigawa-Takeda, K. 1980. Agric. Biol. Chem., 44:1897-1904).

> E1o: 2-oxoglutarate+[dihydrolipoyllysine-residue succinyltransferase]lipoyllysine→[dihydrolipoyllysine-residue succinyltransferase]S-succinyldihydrolipoyllysine+$CO_2$ > E2o: CoA+enzyme N6-(S-succinyldihydrolipoyl)lysine→succinyl-CoA+enzyme N6-(dihydrolipoyl)lysine > E3: protein N6-(dihydrolipoyl)lysine+$NAD^+$→protein N6-(lipoyl)lysine+$NADH+H^+$ α-KGDH is also called oxoglutarate dehydrogenase or 2-oxoglutarate dehydrogenase.

In bacteria belonging to the family Enterobacteriaceae such as *Pantoea ananatis*, the protein subunits having these three kinds of enzymatic activities, respectively, form a complex. The subunits are encoded by sucA, sucB and lpd, respectively, and the sucA and sucB genes locate downstream from the succinate dehydrogenase iron-sulfur protein gene (sdhB) (U.S. Pat. No. 6,331,419). Although these genes are described as genes of *Enterobacter agglomerans* AJ13355 in the aforementioned patent, this strain was later reclassified into *Pantoea ananatis*.

As genes encoding α-KGDH of enterobacteria, the nucleotide sequence of a fragment of *Pantoea ananatis* containing the genes sucA and sucB, a part of the sdhB gene located upstream from these genes, and the sucC gene located downstream of these genes is shown in SEQ ID NO: 46. The amino acid sequences encoded by the part of the sdhB gene, and the sucA, sucB, and sucC genes are shown in SEQ ID NOS: 47 to 50, respectively. Furthermore, sucA and sucB encoding α-KGDH of *Escherichia coli* have been disclosed as Genbank NP_415254 and NP_415255, respectively.

In coryneform bacteria, the E1o subunit is encoded by the odhA gene (registered as NCg11084 of GenBank Accession No. NC_003450, which is also called sucA gene), and the E3 subunit is encoded by the lpd gene (GenBank Accession No. Y16642). On the other hand, it is estimated that the E2o subunit is encoded by the odhA gene together with the E1o subunit as a bifunctional protein (Usuda Y. et al. 1996. Microbiology 142:3347-3354), or encoded by the gene registered as NCg12126 of GenBank Accession No. NC_003450, which is different from the odhA gene. Therefore, in accordance with the presently disclosed subject matter, although the odhA gene is a gene encoding the E1o subunit, it can additionally encode E2o.

The nucleotide sequence of the odhA gene of *Brevibacterium lactofermentum* and the amino acid sequence of the E1o subunit encoded thereby (NCg11084 of GenBank Accession No. NC_003450, WO2006/028298) are shown in SEQ ID NOS: 51 and 52. Furthermore, the nucleotide sequence of the aforementioned NCg12126 of GenBank Accession No. NC_003450 and the amino acid sequence of the E2o subunit encoded thereby are shown in SEQ ID NOS: 53 and 54.

When a microorganism of the presently disclosed subject matter is cultured under anaerobic or microaerobic conditions, it can be a microorganism which has been modified so that it does not produce any organic acid or ethanol under the anaerobic or microaerobic conditions. Additionally, α-ketoglutarate synthase activity can be enhanced. Examples of the organic acid referred to here can include lactic acid, formic acid and acetic acid. Examples of the method for modifying so that any organic acid or ethanol is not produced can include a method of disrupting the gene encoding lactate dehydrogenase (Verumi, G. N. et al. 2002. J. Industrial Microbiol. Biotechnol. 28:325-332; Japanese Patent Laid-open No. 2005-95169).

<2> Method for Producing L-Glutamic Acid of the Present Invention

A method in accordance with the presently disclosed subject matter can be a method for producing an L-amino acid by culturing a microorganism which is able to produce one or two or more kinds of L-amino acids such as L-glutamic acid, L-glutamine, L-proline, L-ornithine, L-citrulline and L-arginine and which has been modified to increase the activity of α-ketoglutarate synthase in a medium to produce and accumulate the L-amino acid in the medium or the cells of the microorganism, and collecting the L-amino acid from the medium or the cells. In a method of the presently disclosed subject matter, the culture can be performed under aerobic conditions, or can be performed under anaerobic or microaerobic conditions. Aerobic conditions usually can be obtained by bubbling the medium with a gas containing oxygen or stirring the medium. If aeration or stirring is not performed, or the aeration or stirring rate is lowered, anaerobic or microaerobic conditions usually can be obtained.

With respect to culturing the microorganism in a medium, it is known by one skilled in the art that a microorganism cultured on a solid medium such as agar medium as slant culture can be directly inoculated into a liquid medium. In accordance with the presently disclosed subject matter, the microorganism cultured in a liquid medium can be inoculated beforehand (seed culture) into a medium for main culture (fermentation medium).

A medium usually used for culturing microorganisms and including a carbon source, a nitrogen source and inorganic salts as well as organic micronutrients such as amino acids and vitamins, if needed, can be used as the medium used for the culture. For example, a usual medium having a composition including mineral salts such as ammonium sulfate, potassium phosphate and magnesium sulfate, added with natural nutrients such as meat extract, yeast extract and peptone can be used.

Any carbon source that can be utilized by the microorganism and allows production of L-glutamic acid, L-glutamine, L-proline, L-ornithine, L-citrulline or L-arginine can be used without any particular limitation. Usually, carbohydrates such as galactose, lactose, glucose, fructose, sucrose, saccharose, starch, cellulose, and aliphatic acids can be used. Additionally, alcoholic sugars such as glycerol, mannitol, xylitol, ribitol and ethanol also can be used. Exemplary embodiment can utilize glucose, fructose, sucrose, glycerol and ethanol. Other exemplary embodiments can utilize glucose and glycerol. Crude glycerol produced in biodiesel fuel production can be utilized. The carbon source can include a single type of carbon source or a plurality of different carbon sources.

Furthermore, saccharified starch solution, molasses, crude glycerol and so forth containing the aforementioned saccharides also can be used. Although concentration of the aforementioned carbon source is not particularly limited, it can be advantageous to make it as high as possible in such a range that the production of L-amino acid is not inhibited. In exemplary embodiments, the fermentation usually can be performed at a concentration of the carbon sources in the range of 5 to 30% (W/V), or in the range of 10 to 20% (W/V). Furthermore, supplemental carbon sources can be added in accordance with decreasing the initial carbon sources consumed during the culture.

Any nitrogen source that can be utilized by the microorganism and allows production of L-amino acid can be used without any particular limitation. Specific examples can include various kinds of organic and inorganic nitrogen compounds such as ammonium salts, nitrates, urea, soybean hydrolysate, casein decomposition product, peptone, yeast extract, meat extract and corn steep liquor. The inorganic salts can include various phosphates, sulfates, and salts of metals such as magnesium, potassium, manganese, iron and zinc. Furthermore, growth promoting factors, for example, vitamins such as biotin, pantothenic acid, inositol and nicotinic acid, nucleotides, amino acids and so forth can be added, as needed. Furthermore, in order to suppress foaming at the time of culture, an appropriate amount of commercially available antifoams can be added to the medium.

pH of the culture medium can be adjusted by adding ammonia gas, aqueous ammonia, sodium carbonate, sodium bicarbonate, potassium carbonate, potassium bicarbonate, magnesium carbonate, sodium hydroxide, calcium hydroxide, magnesium hydroxide, or the like. The pH in the main culture can be within a range of 5 to 10, or a range of 6 to 9.5. The pH of the culture medium can be adjusted by utilizing an alkaline substance, carbonate, urea or the like, as required, in order to maintain the pH during the culture within the aforementioned range.

In accordance with the presently disclosed subject matter, the medium can include the aforementioned carbon source, and carbonate ions, bicarbonate ions or carbon dioxide, and can allow culture under anaerobic, microaerobic or anaerobic conditions. Although carbonate ions or bicarbonate ions are supplied from carbonate salts or bicarbonate salts such as magnesium carbonate, sodium carbonate, sodium bicarbonate, potassium carbonate or potassium bicarbonate, which also can be used as a neutralizer, they also can be supplied from carbon dioxide, as needed. Carbonate ions and bicarbonate ions can be added at a concentration of 0.001 to 5 M, at a concentration of 0.1 to 3 M, or at a concentration of 1 to 2 M. When carbon dioxide is contained, it can be contained in an amount of 50 mg to 25 g, in an amount of 100 mg to 15 g, or in an amount of 150 mg to 10 g, per 1 L of the solution.

At the time of culture of a microorganism, the culture can be performed under aerobic conditions by supplying oxygen by aeration or stirring. However, in a method of the presently disclosed subject matter, the culture can be performed under anaerobic or microaerobic conditions without performing aeration and supplying oxygen. Various conditions of dissolved oxygen concentration can be attained by, for example, lowering aeration or stirring rate, performing the reaction without aeration in a sealed container, bubbling an inert gas containing carbon dioxide, or the like.

The culture temperature can be within a range of 25 to 40° C., or within a range of 30 to 37° C. The culture period can be within a range of 1 to 168 hours, or within a range of 3 to 72 hours.

The culture period can be divided into a period for proliferation of the microorganism and a period for production of L-amino acid, and the culture can be performed for the periods in different media or under different conditions. For example, the microorganism can be proliferated with aeration or stirring, and then the microorganism can be allowed to produce an L-amino acid under anaerobic or microaerobic conditions.

Furthermore, the culture can also be performed with precipitating L-glutamic acid in the medium using a liquid medium adjusted to be under such conditions that L-glutamic acid is precipitated in the medium. Examples of the conditions under which L-glutamic acid precipitates can include pH range of 5.0 to 4.0, a pH range of 4.5 to 4.0, a pH range of 4.3 to 4.0, and a pH of 4.0.

Collection of L-amino acid from the medium after the culture can be performed by a known collection method. For example, the collection can be attained by removing cells from the medium, and then causing crystallization by concentration, ion exchange chromatography, or the like. When the culture is performed with precipitating L-glutamic acid, L-glutamic acid precipitated in the medium can be collected by centrifugation or filtration. In this case, L-glutamic acid dissolving in the medium can be precipitated and then separated together.

EXAMPLES

Hereafter, the presently disclosed subject matter will be specifically explained with reference to examples. However, the presently disclosed subject matter is not limited to the following examples.

Example 1

Construction of a Plasmid for Expressing Genes Encoding α-Ketoglutarate Synthase, Pyruvate Synthase and Ferredoxin of Chlorobium tepidum Chlorobium tepidum is a meso-thermophilic autotrophic bacterium with an optimum growth temperature of 48° C., and the genomic sequence of the TLS strain has been elucidated by Eisen et al. (Eisen, J. A. et al. 2002. Proc. Natl. Acad. Sci. USA 99:9509-9514). The α-ketoglutarate synthase gene, the pyruvate synthase gene and the ferredoxin gene were isolated from this strain, and a plasmid for simultaneously expressing these three genes was constructed.

<1-1> Construction of a Plasmid for Expressing α-Ketoglutarate Synthase Gene of C. tepidum PCR was performed using the genomic DNA of the C. tepidum TLS strain (ATCC 49652) as a template and the oligonucleotides of SEQ ID NOS: 21 and 22 to amplify a gene fragment containing genes for the α-subunit and β-subunit of α-ketoglutarate synthase. The obtained gene fragment was digested with BamHI and inserted into BamHI site of pSTV28 (Takara Bio) to construct a plasmid for expressing α-ketoglutarate synthase gene, which was designated pSTV-KGS. The α-ketoglutarate synthase gene is located downstream from the lac promoter derived from pSV28 in the resulting plasmid, and can be expressed from the promoter.

<1-2> Construction of a Plasmid for Expressing α-Ketoglutarate Synthase Gene and Pyruvate Synthase Gene of C. tepidum PCR was performed using the genomic DNA of the C. tepidum TLS strain (ATCC 49652) as a template and the oligonucleotides of SEQ ID NOS: 23 and 24 to amplify the pyruvate synthase gene fragment. The obtained gene fragment was digested with XbaI and ligated to pSTV-KGS digested with XbaI to construct a plasmid for expressing the α-ketoglutarate synthase gene and the pyruvate synthase gene, which was designated pSTV-KGS-PS.

<1-3> Construction of a Plasmid for Expressing α-Ketoglutarate Synthase Gene, Pyruvate Synthase Gene and Ferredoxin Gene of C. tepidum PCR was performed using the genomic DNA of the C. tepidum TLS strain (ATCC 49652) as a template and the oligonucleotides of SEQ ID NOS: 25 and 26 to amplify the ferredoxin I gene fragment. The gene fragment was digested with SmaI and inserted into pSTV-KGS-PS digested with SmaI to construct a plasmid for expressing the α-ketoglutarate synthase gene, the pyruvate synthase gene and the ferredoxin I gene, which was designated pSTV-FdI-KGS-PS. The α-ketoglutarate synthase gene, the pyruvate synthase gene and the ferredoxin I gene are located downstream from the lac promoter of pSV28 in the resulting plasmid, and can be expressed from the promoter.

Example 2

Construction of α-Ketoglutarate Dehydrogenase Deficient Strain of Escherichia coli <2-1> Construction of a Plasmid for Disrupting sucA Gene of Escherichia coli From the E. coli MG1655 strain, a strain of which sucA gene encoding the E1 subunit of α-ketoglutarate dehydrogenase was disrupted was constructed. Primers were synthesized on the basis of the nucleotide sequence of the sucA gene locating at the nucleotide numbers 757929 to 760730 of the genomic sequence (Genbank Accession No. U00096) and used for PCR using the genomic DNA of the E. coli MG1655 strain as a template to amplify N- and C-terminal fragments of the sucA gene. The nucleotide sequence of the sucA gene of Escherichia coli is shown in SEQ ID NO: 55 and the amino acid sequence of E1 subunit encoded by the gene is shown in SEQ ID NO: 56. As the PCR primers for amplification of the N-terminal fragment, the oligonucleotides of SEQ ID NOS: 42 and 43 were used, and as the PCR primers for amplification of the C-terminal fragment, the oligonucleotides of SEQ ID NOS: 44 and 45 were used. HindIII site and XbaI site were designed in the oligonucleotide of SEQ ID NO: 42 and the oligonucleotide of SEQ ID NO: 45, respectively.

Each of the amplified DNA fragments obtained after PCR was purified using QIAquick PCR Purification Kit (Qiagen), and the purified N-terminal DNA fragment and C-terminal DNA fragment, and the primers of SEQ ID NOS: 42 and 45 were used in crossover PCR (Link, A. J. et al. 1997. J. Bacteriol. 179:6228-6237) to obtain a deficient-type sucA fragment. The DNA fragment was purified, then digested with HindIII and XbaI (Takara Bio), and cloned in the temperature sensitive plasmid pMAN997 (Matsui, H. et al. 2001. Biosci. Biotechnol. Biochem. 65:570-578; WO99/03988) similarly digested with HindIII and XbaI to construct a plasmid for sucA disruption, which was designated pMANΔsucA.

<2-2> Construction of α-Ketoglutarate Dehydrogenase Deficient Strain Derived from E. coli MG1655 Strain The E. coli MG1655 strain was transformed with the plasmid pMANΔsucA, and colonies were selected at 30° C. on an LB+ampicillin plate (LB agar plate containing 25 μg/mL of ampicillin). The selected clones were cultured overnight at 30° C. in a liquid medium, then the medium was diluted 1000 times and inoculated on an LB+ampicillin plate, and colonies were selected at 42° C. The selected clones were spread on an LB+ampicillin plate and cultured at 30° C., and then the cells corresponding to ⅛ of the plate were suspended in 2 mL of LB medium, and cultured at 42° C. for 4 to 5 hours with shaking. The cell culture medium diluted 10000 times was inoculated on an LB plate, several hundreds of colonies among the obtained colonies were inoculated on an LB plate and LB+ampicillin plate, and ampicillin sensitive strains were selected by confirming growth. Colony PCR was performed for several strains among the ampicillin sensitive strains to confirm deficiency of the sucA gene. In this way, a sucA deficient strain derived from E. coli MG1655 strain, MG1655ΔsucA strain, was obtained.

Example 3

Construction of Lactate Dehydrogenase Deficient Strain of E. coli

Lactate dehydrogenase is an enzyme which catalyzes a reaction which generates lactic acid from pyruvic acid using NADH as a coenzyme. In order to suppress generation of lactic acid in culture of E. coli under limited oxygen, a strain deficient in the ldhA gene encoding lactate dehydrogenase was constructed. This gene was deleted using the method developed by Datsenko and Wanner called "Red-driven integration" (Datsenko, K. A. and Wanner, B. L. 2000. Proc. Natl. Acad. Sci. USA 97:6640-6645) and an excision system of λ-phage (Cho, E. H. et al. 2002. J. Bacteriol. 184:5200-5203). Using this method, a gene-disrupted strain can be constructed in one step using a PCR product obtained using synthetic oligonucleotides as primers in which a part of a target gene is designed in the 5' end side of the synthetic oligonucleotide, and a part of an antibiotic resistance gene is designed in the 3' end side of the same. By further combining the excision system derived from λ-phage, the antibiotic resistance gene incorporated into the gene-disrupted strain can be eliminated.

<3-1> Construction of Strain Deficient in ldhA Gene Encoding Lactate Dehydrogenase According to the description of WO2005/010175, synthetic oligonucleotides were used as primers, in which each of the oligonucleotides had a sequence corresponding to a part of the ldhA gene at the 5' end, and a sequence corresponding to each of the ends of attL and attR of λ-phage at the 3' end, respectively, and the plasmid pMW118-attL-Cm-attR as a template to perform PCR. The sequences of the synthetic oligonucleotides used for the primers are shown in SEQ ID NOS: 27 and 28. The amplified PCR product was purified with agarose gel, and introduced into the E. coli MG1655ΔsucA strain harboring the plasmid pKD46 having temperature sensitive replication ability by electroporation. Then, an ampicillin sensitive strain in which plasmid pKD46 was eliminated was obtained, and the deletion of the ldhA gene was confirmed by PCR. Furthermore, in order to remove the att-cat gene introduced into the ldhA gene, the strain was transformed with the helper plasmid pMW-intxis-ts, and an ampicillin resistant strain was selected. The pMW-intxis-ts is a plasmid having the integrase (Int) gene and the excisionase (Xis) gene of λ phage, of which replication is temperature sensitive.

Then, ldhA-disrupted strains in which att-cat and pMW-intxis-ts were eliminated were obtained on the basis of sensitivities to ampicillin and chloramphenicol. From each of the obtained candidate ldhA-deficient strains, a genomic DNA was prepared and used with the oligonucleotides of SEQ ID NOS: 29 and 30 to perform PCR, followed by electrophoresis analysis. A ldhA-deficient strain which showed a band smaller by about 1.0 kbs compared with the band obtained in PCR performed using the genomic DNA prepared from the MG1655ΔsucA strain as a template was designated MG1655ΔsucAΔldhA strain.

Example 4

Measurement of α-Ketoglutarate Synthase Activity of a Strain Expressing α-Ketoglutarate Synthase Gene of C. tepidum In order to confirm that the α-ketoglutarate synthase gene of C. tepidum expresses the activity in E. coli, a vector for expressing α-ketoglutarate synthase gene of C. tepidum was constructed and introduced into MG1655ΔsucA, and the activity was measured.

<4-1> Construction of a Plasmid for Expressing α-Ketoglutarate Synthase Gene of C. tepidum PCR was performed using the genomic DNA of the C. tepidum TLS strain (ATCC 49652) as a template and the oligonucleotides shown in SEQ ID NOS: 21 and 22 to amplify the α-ketoglutarate synthase gene fragment. The obtained gene fragment was digested with BamHI, and inserted into the BamHI site of pUC18 (Takara Bio) to construct a plasmid for expressing the α-ketoglutarate synthase gene, which was designated pUC-KGS. The α-ketoglutarate synthase gene locates downstream from the lac promoter of pUC18 in the resulting plasmid, and it can be expressed from the promoter. Furthermore, since the copy number of pUC18 is higher than that of pSTV28, detection of the enzymatic activity is easy.

<4-2> Preparation of Crude Enzyme Solution of a Strain Expressing α-Ketoglutarate Synthase Gene of C. tepidum pUC-KGS and the vector pUC18 as control for comparison were each introduced into MG1655ΔsucA by electroporation, and transformants were obtained on the basis of ampicillin resistance. After confirming introduction of the plasmids, the strain expressing α-ketoglutarate synthase gene of C. tepidum and the control strain were designated MG1655ΔsucA/pUC-KGS and MG1655ΔsucA/pUC18, respectively.

Each of the above strains was inoculated into LB medium containing 1 mM IPTG, and cultured overnight at 37° C. as preculture. Cells were collected from 10 ml of the medium by centrifugation, and suspended in 300 μl of 50 mM HEPES buffer (pH 8.0). The suspension was subjected to ultrasonic disruption and centrifuged at 15000 rpm for 15 minutes, and the obtained supernatant was used as a crude enzyme solution.

<4-3> Measurement of α-Ketoglutarate Synthase Activity of Crude Enzyme Solution Obtained from a Strain Expressing α-Ketoglutarate Synthase Gene of C. tepidum A reaction was performed by adding 50 μl of the crude enzyme solution to 1 ml of the reaction solution shown below. First, the reaction solution containing all the components except for α-ketoglutarinc acid serving as a substrate was added to a cell for spectrometry, and the cell was sealed with a rubber stopper and an aluminum cap. Argon gas was blown into the cell for 5 minutes using a syringe to lower the oxygen concentration in the cell. The cell was set on a spectrophotometer (U-3210 Spectrophotometer, Hitachi, Ltd.), and an α-ketoglutaric acid solution was added using a syringe to start the reaction. The reaction was allowed at 37° C. for 30 minutes, and absorbance was periodically measured at 578 nm to monitor change of amount of reduced methylviologen.

Reaction Mixture:

| | |
|---|---|
| $MgCl_2$ | 1 mM |
| Dithiothreitol | 1 mM |
| Methylviologen | 5 mM |
| CoA | 0.25 mM |
| α-Ketoglutaric acid | 10 mM | added immediately before the start of the measurement:

| | |
|---|---|
| HEPES (pH 8.0) | 50 mM |

The results are shown in Table 1. In the table, KGS indicates α-ketoglutarate synthase. In the aforementioned reaction system, reduced methylviologen increases due to the decarboxylation of α-ketoglutaric acid by α-ketoglutarate synthase. The extinction coefficient of reduced methylviologen at 578 nm, $\epsilon 578$, is 9.8/mM/cm, and 1 U of the enzymatic activity was defined as an activity for reducing 1 μmol of methylviologen per 1 minute. Whereas α-ketoglutarate synthase activity was not observed for the control strain MG1655ΔsucA/pUC18, 0.1 U/mg of the activity was confirmed for the MG1655ΔsucA/pUC18-KGS strain expressing the α-ketoglutarate synthase gene of C. tepidum.

TABLE 1

| Strain | KGS activity (U/mg) |
|---|---|
| MG1655ΔsucA/pUC18 | 0.00 |
| MG1655ΔsucA/pUC-KGS | 0.10 |

Example 5

Effect on L-Glutamic Acid Producing Ability in a Strain Expressing α-Ketoglutarate Synthase Gene, Pyruvate Synthase Gene and Ferredoxin Gene of *C. tepidum* Under Limited Oxygen Concentration with Glucose as a Carbon Source In order to examine influence of expression of α-ketoglutarate synthase activity on the L-glutamic acid production under limited oxygen concentration, the aforementioned plasmid pSTV-KGS-PS-FdI for expressing α-ketoglutarate synthase gene, pyruvate synthase gene and ferredoxin gene of *C. tepidum* was introduced into MG1655ΔsucAΔldhA, and culture was performed.

Each of pSTV-FdI-KGS-PS and the vector pSTV28 as a control for comparison was introduced into MG1655ΔsucAΔldhA by electroporation, and transformants were obtained on the basis of chloramphenicol resistance. After confirming introduction of the plasmids, the strain expressing the α-ketoglutarate synthase gene, the pyruvate synthase gene and the ferredoxin gene of *C. tepidum* was designated MG1655ΔsucAΔldhA/pSTV-FdI-KGS-PS, and the control strain was designated MG1655ΔsucAΔldhA/pSTV28. The strains prepared above were cultured to examine L-glutamic acid producing ability thereof.

MG1655ΔsucAΔldhA/pSTV-FdI-KGS-PS and the control strain MG1655ΔsucAΔldhA/pSTV28 were each inoculated on the LB medium, and cultured overnight at 37° C. as preculture. Cells corresponding to ⅙ of the plate were inoculated to 50 ml of a glucose medium having the following composition in a 500-ml volume conical flask, and cultured at 37° C. for 31 hours. In order to limit oxygen, the culture was performed at a stirring rate of 100 rpm. After the culture, L-glutamic acid which had accumulated in the medium was measured using a Biotech Analyzer (Asahi Chemical Industry).

Composition of Glucose Medium:

| Glucose | 40 g/L |
|---|---|
| MgSO$_4$•7H$_2$O | 1.0 g/L |
| (NH$_4$)$_2$SO$_4$ | 20 g/L |
| KH$_2$PO$_4$ | 1.0 g/L |
| Yeast extract | 2.0 g/L |
| FeSO$_4$•7H$_2$O | 0.01 g/L |
| MnSO$_4$•5H$_2$O | 0.01 g/L |
| Thiamine HCl | 0.01 g/L |
| Chloramphenicol | 25 mg/L |
| Calcium carbonate | 50 g/L | pH 7.0 (adjusted with KOH)
Sterilization condition: 120° C., 20 minutes

The results are shown in Table 2. L-Glutamic acid yield with respect to consumed glucose was improved by 0.6% in MG1655ΔsucAΔldhA/pSTV-FdI-KGS-PS introduced with the vector for expressing the α-ketoglutarate synthase gene, the pyruvate synthase gene and the ferredoxin gene of *C. tepidum* compared with the control, MG1655ΔsucAΔldhA/pSTV28.

TABLE 2

| Strain | OD620 | Residual glucose (g/L) | L-Glutamic acid yield (%) |
|---|---|---|---|
| MG1655ΔsucAΔldhA/pSTV28 | 14.0 | 2.1 | 1.05 |
| MG1655ΔsucAΔldhA/pSTV-FdI-KGS-PS | 13.3 | 3.6 | 1.65 |

Example 6

Effect on L-Glutamic Acid Producing Ability in a Strain Expressing α-Ketoglutarate Synthase Gene, Pyruvate Synthase Gene and Ferredoxin Gene of *C. tepidum* with Glycerol as a Carbon Source The MG1655ΔsucAΔldhA/pSTV-FdI-KGS-PS strain expressing the α-ketoglutarate synthase gene, the pyruvate synthase gene and the ferredoxin gene of *C. tepidum* and the control strain MG1655ΔsucAΔldhA/pSTV28 were used to examine L-glutamic acid producing ability thereof observed with glycerol as a carbon source.

Each of MG1655ΔsucAΔldhA/pSTV-FdI-KGS-PS and the control strain MG1655ΔsucAΔldhA/pSTV28 was inoculated to the LB medium, and cultured overnight at 37° C. as preculture. Cells corresponding to ½ of the plate were inoculated to 20 ml of a glycerol medium having the following composition in a 500-ml volume Sakaguchi flask, and cultured at 37° C. for 29 hours under an aerobic condition at a stirring rate of 120 rpm. After completion of the culture, L-glutamic acid which had accumulated in the medium was measured using a Biotech Analyzer (Asahi Chemical Industry).

Composition of Glycerol Medium:

| Glycerol | 50 g/L |
|---|---|
| MgSO$_4$•7H$_2$O | 1.0 g/L |
| (NH$_4$)$_2$SO$_4$ | 20 g/L |
| KH$_2$PO$_4$ | 1.0 g/L |
| Yeast extract | 2.0 g/L |
| FeSO$_4$•7H$_2$O | 0.01 g/L |
| MnSO$_4$•5H$_2$O | 0.01 g/L |
| Thiamine HCl | 0.01 g/L |
| Chloramphenicol | 25 mg/L |
| Calcium carbonate | 30 g/L | pH 7.0 (adjusted with KOH)
Sterilization condition: 120° C., 20 minutes

The results are shown in Table 3. L-Glutamic acid yield with respect to consumed glycerol was improved by 6% in MG1655ΔsucAΔldhA/pSTV-FdI-KGS-PS introduced with the vector for expressing the α-ketoglutarate synthase gene, the pyruvate synthase gene and the ferredoxin gene of *C. tepidum* compared with the control, MG1655ΔsucAΔldhA/pSTV28.

TABLE 3

| Strain | OD620 | Residual glycerol (g/L) | L-Glutamic acid yield (%) |
|---|---|---|---|
| MG1655ΔsucAΔldhA/pSTV28 | 29.4 | 0.0 | 31.3 |
| MG1655ΔsucAΔldhA/pSTV-FdI-KGS-PS | 23.6 | 0.0 | 37.2 |

Example 7

Construction of a Plasmid for Expressing
α-Ketoglutarate Synthase Gene of *C. tepidum*,
Flavodoxin NADP$^+$ Reductase Gene of *E. coli* and
Ferredoxin or Flavodoxin Gene of *E. coli*

As a regeneration system for a coenzyme required for α-ketoglutarate synthase activity, the flavodoxin NADP$^+$ reductase gene of *E. coli* and the ferredoxin or flavodoxin gene of *E. coli* were used to construct a plasmid simultaneously expressing the three genes. As the ferredoxin NADP$^+$ reductase gene of *E. coli*, the fpr gene was used, as the flavodoxin gene of *E. coli*, the fldA gene and the fldB gene were used, and as the ferredoxin gene, the fdx gene and the yfhL gene were used.

<7-1> Construction of a Plasmid for Expressing α-Ketoglutarate Synthase Gene of *C. tepidum* pSTV-KGS constructed in Example 1 was digested with BamHI, and the obtained α-ketoglutarate synthase gene fragment was inserted into the BamHI site of pMWPthr to construct the vector pMWPthr-KGS for expressing the α-ketoglutarate synthase gene. pMWPthr corresponds to the vector pMW118 (Nippon Gene) having the promoter region (Pthr) of the threonine operon (thrABC) locating at the nucleotide numbers of 183 to 330 of the genomic sequence of the *E. coli* K-12 strain (Genbank Accession No. U00096) shown in SEQ ID NO: 31 between the HindIII and XbaI sites. This plasmid can express a gene when the gene is cloned downstream from that promoter.

<7-2> Construction of a Vector for Amplifying Flavodoxin NADP$^+$ Reductase Gene of *E. coli*

PCR was performed using the genomic DNA of the *E. coli* MG1655 strain as a template and the oligonucleotides shown in SEQ ID NOS: 32 and 33 to amplify the flavodoxin NADP$^+$ reductase gene fragment. The obtained gene fragment was digested with SmaI, and inserted into the SmaI site of pMWPthr to construct a plasmid for amplifying the flavodoxin NADP$^+$ reductase gene, which was designated pMWPthr-fpr.

<7-3> Construction of a Vector for Amplifying Flavodoxin (fldA) Gene of *E. coli*

PCR was performed using the genomic DNA of the *E. coli* MG1655 strain as a template and the oligonucleotides shown in SEQ ID NOS: 34 and 35 to amplify the flavodoxin (fldA) gene fragment. The gene fragment was digested with EcoRI, and inserted into the EcoRI site of pMWPthr to construct a plasmid for amplifying the flavodoxin (fldA) gene, pMWPthr-fldA.

<7-4> Construction of a Plasmid for Amplifying Flavodoxin Gene (fldB) of *E. coli*

PCR was performed using the genomic DNA of the *E. coli* MG1655 strain as a template and the oligonucleotides shown in SEQ ID NOS: 36 and 37 to amplify the flavodoxin (fldB) gene fragment. The gene fragment was digested with EcoRI, and inserted into the EcoRI site of pMWPthr to construct a plasmid for amplifying the flavodoxin (fldB) gene, pMWPthr-fldB.

<7-5> Construction of a Plasmid for Amplifying Ferredoxin (fdx) Gene of *E. coli*

PCR was performed using the genomic DNA of the *E. coli* MG1655 strain as a template and the oligonucleotides shown in SEQ ID NOS: 38 and 39 to amplify the ferredoxin (fdx) gene fragment. The gene fragment was digested with EcoRI, and inserted into the EcoRI site of pMWPthr to construct a plasmid for amplifying the ferredoxin (fdx) gene, pMWPthr-fdx.

<7-6> Construction of a Plasmid for Amplifying Ferredoxin (yfhL) Gene of *E. coli*

PCR was performed using the genomic DNA of the *E. coli* MG1655 strain as a template and the oligonucleotides shown in SEQ ID NOS: 40 and 41 to amplify the ferredoxin (yfhL) gene fragment. The gene fragment was digested with EcoRI, and inserted into the EcoRI site of pMWPthr to construct a plasmid for amplifying the ferredoxin (yfhL) gene, pMWPthr-yfhL.

<7-7> Construction of a Plasmid for Expressing α-Ketoglutarate Synthase Gene of *C. tepidum* and Amplifying Ferredoxin NADP$^+$ Reductase Gene and Flavodoxin (fldA) Gene of *E. coli* pMWPthr-fldA was digested with EcoRI, and the obtained fldA gene fragment was ligated with pMWPthr-KGS treated with EcoRI to obtain pMWPthr-KGS-fldA. Then, pMWPthr-fpr was digested with SmaI, and the obtained fpr gene fragment was ligated with pMWPthr-KGS-fldA treated with SmaI to construct a plasmid for expressing the α-ketoglutarate synthase gene and enhancing expression of the flavodoxin NADP$^+$ reductase gene and the flavodoxin (fldA) gene of *E. coli*, pMWPthr-KGS-fpr-fldA.

<7-8> Construction of a Plasmid for Expressing α-Ketoglutarate Synthase Gene of *C. tepidum* and Amplifying the Flavodoxin NADP$^+$ Reductase Gene and Flavodoxin (fldB) Gene of *E. coli*

The fldB gene fragment obtained by digesting pMWPthr-fldB with EcoRI was ligated with pMWPthr-KGS treated with EcoRI to obtain pMWPthr-KGS-fldB. Then, pMWPthr-fpr was digested with SmaI, and the obtained fpr gene fragment was ligated with pMWPthr-KGS-fldB treated with SmaI to construct a plasmid for enhancing expression of the α-ketoglutarate synthase gene, the flavodoxin NADP$^+$ reductase gene and the flavodoxin (fldB) gene, pMWPthr-KGS-fpr-fldB.

<7-9> Construction of a Plasmid for Expressing α-Ketoglutarate Synthase Gene of *C. tepidum* and Amplifying Flavodoxin NADP$^+$ Reductase Gene and Ferredoxin (fdx) Gene of *E. coli*

The fdx gene fragment obtained by digesting pMWPthr-fdx with EcoRI was ligated with pMWPthr-KGS treated with EcoRI to obtain pMWPthr-KGS-fdx. Then, pMWPthr-fpr was digested with SmaI, and the obtained fpr gene fragment was ligated with pMWPthr-KGS-fdx treated with SmaI to obtain a vector for enhancing expression of the α-ketoglutarate synthase gene, the flavodoxin NADP$^+$ reductase gene and the ferredoxin (fdx) gene, pMWPthr-KGS-fpr-fdx.

<7-10> Construction of a Plasmid for Expressing the α-Ketoglutarate Synthase Gene of *C. tepidum* and Amplifying the Flavodoxin NADP$^+$ Reductase Gene and Ferredoxin (yfhL) Gene of *E. coli*

The yfhL gene fragment obtained by digesting pMWPthr-yfhL with EcoRI was ligated with pMWPthr-KGS treated with EcoRI to obtain pMWPthr-KGS-yfhL. Then, pMWPthr-fpr was digested with SmaI, and the obtained fpr gene fragment was ligated with pMWPthr-KGS-yfhL treated with SmaI to construct a plasmid for enhancing expression of the α-ketoglutarate synthase gene, the flavodoxin NADP$^+$ reductase gene and the ferredoxin (yfhL) gene, pMWPthr-KGS-fpr-yfhL.

In the aforementioned plasmids, the α-ketoglutarate synthase gene of *C. tepidum* is transcribed from Pthr, and the other genes are also transcribed by read through from Pthr.

Example 8

Effect on L-Glutamic Acid Producing Ability in a Strain in which Expression of α-Ketoglutarate Synthase Gene of *C. tepidum*, Flavodoxin NADP$^+$ Reductase Gene of *E. coli* and Flavodoxin or Ferredoxin Gene of *E. coli* are Enhanced with Glycerol as a Carbon Source In order to examine the influence of the enhancement of α-ketoglutarate synthase activity derived from *C. tepidum* obtained by amplification of the flavodoxin NADP$^+$ reductase gene of *E. coli* and the flavodoxin or ferredoxin gene of *E. coli* on the L-glutamic acid production under limited oxygen concentration, the aforementioned plasmids for enhancing expression of the α-ketoglutarate synthase gene of *C. tepidum*, the flavodoxin NADP$^+$ reductase gene of *E. coli* and the flavodoxin or ferredoxin gene of *E. coli* were each introduced into MG1655ΔsucAΔldhA, and culture was performed.

<8-1> Introduction of Plasmids for Amplifying α-Ketoglutarate Synthase Gene of *C. tepidum*, Flavodoxin NADP$^+$ Reductase Gene of *E. coli* and Flavodoxin or Ferredoxin Gene of *E. coli* into MG1655ΔsucAΔldhA Strain The vector for expressing the α-ketoglutarate synthase gene of *C. tepidum*, pMWPthr-KGS, and the plasmids for enhancing expressions of the α-ketoglutarate synthase gene, the flavodoxin NADP$^+$ reductase gene of *E. coli* and the flavodoxin or ferredoxin gene of *E. coli*, pMWPthr-KGS-fpr-fldA, pMWPthr-KGS-fpr-fldB, pMWPthr-KGS-fpr-fdx, pMWPthr-KGS-fpr-yfhL, the plasmid pMWPthr as a control for comparison, and the plasmid for amplifying the flavodoxin NADP$^+$ reductase gene of *E. coli*, pMWPthr-fpr, were each introduced into MG1655ΔsucAΔldhA by electroporation, and transformants were obtained on the basis of kanamycin resistance. After confirming introduction of the plasmids, the plasmid-introduced strains were designated MG1655ΔsucAΔldhA/pMWPthr-KGS, MG1655ΔsucAΔldhA/pMWPthr-KGS-fpr-fldA, MG1655ΔsucAΔldhA/pMWPthr-KGS-fpr-fldB, MG1655ΔsucAΔldhA/pMWPthr-KGS-fpr-fdx, MG1655ΔsucAΔldhA/pMWPthr-KGS-fpr-yfhL, MG1655ΔsucAΔldhA/pMWPthr and MG1655ΔsucAΔldhA/pMWPthr-fpr, respectively.

<8-2> Effect on L-Glutamic Acid Producing Ability in Strains in which Expression of α-Ketoglutarate Synthase Gene of *C. tepidum*, Flavodoxin NADP$^+$ Reductase Gene of *E. coli* and Flavodoxin or Ferredoxin Gene of *E. coli* are Enhanced with Glycerol as a Carbon Source The strains prepared in <8-1>, the strain in which the α-ketoglutarate synthase gene of *C. tepidum* was expressed, MG1655ΔsucAΔldhA/pMWPthr-KGS, the strains in which expressions of the α-ketoglutarate synthase gene of *C. tepidum*, the flavodoxin NADP$^+$ reductase gene of *E. coli* and the flavodoxin or ferredoxin gene of *E. coli* were enhanced, MG1655ΔsucAΔldhA/pMWPthr-KGS-fpr-fldA, MG1655ΔsucAΔldhA/pMWPthr-KGS-fpr-fldB, MG1655ΔsucAΔldhA/pMWPthr-KGS-fpr-fdx, MG1655ΔsucAΔldhA/pMWPthr-KGS-fpr-yfhL, the control strains MG1655ΔsucAΔldhA/pMWPthr, and the strain in which the flavodoxin NADP$^+$ reductase gene of *E. coli* was amplified, MG1655ΔsucAΔldhA/pMWPthr-fpr, were used to examine L-glutamic acid producing ability thereof observed with glycerol as a carbon source under aerobic conditions.

Cells of each strain cultured overnight at 37° C. on the LB medium were inoculated in an amount corresponding to ½ of the plate to 20 mL of a medium (the glycerol medium described in Example 6 containing 40 mg/L of kanamycin instead of chloramphenicol) in a 500-mL volume Sakaguchi flask, and cultured at 37° C. for 29 hours at a stirring rate of 120 rpm. After completion of the culture, L-glutamic acid which had accumulated in the medium was measured using a Biotech Analyzer (Asahi Chemical Industry).

The results are shown in Table 4. Compared with the control strains, MG1655ΔsucAΔldhA/pMWPthr, and MG1655ΔsucAΔldhA/pMWPthr-fpr in which flavodoxin NADP$^+$ reductase gene of *E. coli* was amplified, the L-glutamic acid yield was improved by 3% with respect to the consumed glycerol in the strain expressing the α-ketoglutarate synthase gene of *C. tepidum*, MG1655ΔsucAΔldhA/pMWPthr-KGS, and improvements of the same by 8 to 9% were observed in all the strains in which expressions of the α-ketoglutarate synthase gene of *C. tepidum*, the flavodoxin NADP$^+$ reductase gene of *E. coli* and the flavodoxin or ferredoxin gene of *E. coli* were enhanced, MG1655ΔsucAΔldhA/pMWPthr-KGS-fpr-fldA, MG1655ΔsucAΔldhA/pMWPthr-KGS-fpr-fldB, MG1655ΔsucAΔldhA/pMWPthr-KGS-fpr-fdx and MG1655ΔsucAΔldhA/pMWPthr-KGS-fpr-yfhL.

TABLE 4

| Strain | OD620 | Residual glycerol (g/L) | L-Glutamic acid yield (%) |
|---|---|---|---|
| MG1655ΔsucAΔldhA/pMWPthr | 31.8 | 0.0 | 37.9 |
| MG1655ΔsucAΔldhA/pMWPthr-fpr | 33.9 | 0.0 | 37.2 |
| MG1655ΔsucAΔldhA/pMWPthr-KGS | 27.6 | 0.0 | 40.2 |
| MG1655ΔsucAΔldhA/pMWPthr-KGS-fpr-fldA | 20.1 | 3.8 | 46.5 |
| MG1655ΔsucAΔldhA/pMWPthr-KGS-fpr-fldB | 20.1 | 2.3 | 46.7 |
| MG1655ΔsucAΔldhA/pMWPthr-KGS-fpr-fdx | 22.8 | 0.0 | 46.5 |
| MG1655ΔsucAΔldhA/pMWPthr-KGS-fpr-yfhL | 19.7 | 2.5 | 46.8 |

Example 9

Effect on L-Glutamic Acid Producing Ability in a Strain in which α-Ketoglutarate Synthase Gene of *C. tepidum*, Flavodoxin NADP$^+$ Reductase Gene of *E. coli* and Flavodoxin or Ferredoxin Gene of *E. coli* are Enhanced with Glucose as a Carbon Source Under Limited Oxygen The strains constructed in Example 8, the control, MG1655ΔsucAΔldhA/pMWPthr, and the strains in which expressions of the α-ketoglutarate synthase gene of *C. tepidum*, the flavodoxin NADP$^+$ reductase gene of *E. coli* and the flavodoxin or ferredoxin gene of *E. coli* were enhanced, MG1655ΔsucAΔldhA/pMWPthr-KGS-fpr-fldA, MG1655ΔsucAΔldhA/pMWPthr-KGS-fpr-fldB, MG1655ΔsucAΔldhA/pMWPthr-KGS-fpr-fdx and MG1655ΔsucAΔldhA/pMWPthr-KGS-fpr-yfhL were each cultured overnight at 37° C. on the LB medium as preculture. Cells of each strain corresponding to ⅙ of the plate were inoculated into 50 mL of a medium (the glucose medium described in Example 5 containing 40 mg/L of kanamycin instead of chloramphenicol) in a 500-mL volume conical flask, and cultured at 37° C. for 38 hours. In order to restrict oxygen, the culture was performed at a stirring rate of 100 rpm. After completion of the culture, L-glutamic acid which had accumulated in the medium was measured using a Biotech Analyzer (Asahi Chemical Industry).

The results are shown in Table 5. Compared with the control, MG1655ΔsucAΔldhA/pMWPthr, the yield of L-glutamic acid was improved in all the strains in which expressions of the α-ketoglutarate synthase gene of *C. tepidum*, the flavodoxin NADP$^+$ reductase gene of *E. coli* and the flavodoxin or ferredoxin gene of *E. coli* were enhanced, MG1655ΔsucAΔldhA/pMWPthr-KGS-fpr-fldA, MG1655ΔsucAΔldhA/pMWPthr-KGS-fpr-fldB, MG1655ΔsucAΔldhA/pMWPthr-KGS-fpr-fdx and MG1655ΔsucAΔldhA/pMWPthr-KGS-fpr-yfhL.

TABLE 5

| Strain | OD620 | Residual glucose (g/L) | L-Glutamic acid yield (%) |
| --- | --- | --- | --- |
| MG1655ΔsucAΔldhA/pMWPthr | 13.8 | 0.0 | 0.91 |
| MG1655ΔsucAΔldhA/pMWPthr-KGS-fpr-fldA | 13.8 | 0.0 | 1.34 |
| MG1655ΔsucAΔldhA/pMWPthr-KGS-fpr-fldB | 12.8 | 0.0 | 1.38 |
| MG1655ΔsucAΔldhA/pMWPthr-KGS-fpr-fdx | 13.8 | 0.0 | 1.48 |
| MG1655ΔsucAΔldhA/pMWPthr-KGS-fpr-yfhL | 13.0 | 0.0 | 1.43 |

Example 10

Effect on L-Glutamic Acid Producing Ability in Strain in which Expressions of α-Ketoglutarate Synthase Gene of *C. tepidum*, Flavodoxin NADP$^+$ Reductase Gene of *E. coli* and Flavodoxin Gene of *E. coli* are Enhanced with Glycerol as a Carbon Source The strain prepared in Example 8, the strain in which expressions of the α-ketoglutarate synthase gene of *C. tepidum*, the flavodoxin NADP$^+$ reductase gene of *E. coli* and the flavodoxin gene of *E. coli* were enhanced, MG1655ΔsucAΔldhA/pMWPthr-KGS-fpr-fldA, and the control strain, MG1655ΔsucAΔldhA/pMWPthr were used to examine L-glutamic acid producing ability thereof under an aerobic condition with glucose as a carbon source.

Cells of each strain cultured overnight at 37° C. on the LB medium were inoculated in an amount corresponding to ¼ of the plate to 20 mL of a glucose+methionine medium (the glucose medium described in Example 5 containing 40 mg/L of kanamycin instead of chloramphenicol and further added with 0.2 g/L of DL-methionine) in a 500-mL volume Sakaguchi flask, and cultured at 37° C. for 25 hours at a stirring rate of 120 rpm. After completion of the culture, L-glutamic acid accumulated in the medium was measured using a Biotech Analyzer (Asahi Chemical Industry).

The results are shown in Table 6. Compared with the control, MG1655ΔsucAΔldhA/pMWPthr, improvement of the yield by about 6% was observed for the strain in which expressions of the α-ketoglutarate synthase gene of *C. tepidum*, the flavodoxin NADP$^+$ reductase gene of *E. coli* and the flavodoxin gene of *E. coli* strain were enhanced, MG1655ΔsucAΔldhA/pMWPthr-KGS-fpr-fldA.

TABLE 6

| Strain | OD620 | Residual glucose (g/L) | L-Glutamic acid yield (%) |
| --- | --- | --- | --- |
| MG1655ΔsucAΔldhA/pMWPthr | 24.6 | 0.0 | 40.6 |
| MG1655ΔsucAΔldhA/pMWPthr-KGS-fpr-fldA | 24.1 | 0.0 | 46.8 |

Example 11

Effect on L-Glutamic Acid Producing Ability in *Pantoea ananatis* in which Expressions of α-Ketoglutarate Synthase Gene of *C. tepidum*, Flavodoxin NADP$^+$ Reductase Gene of *E. coli* and Flavodoxin Gene of *E. coli* are Enhanced with Glycerol as a Carbon Source In order to examine the effect of enhancement of α-ketoglutarate synthase activity on L-glutamic acid production in *P. ananatis*, the plasmid for expressing the α-ketoglutarate synthase gene of *C. tepidum*, the flavodoxin NADP$^+$ reductase gene of *E. coli* and the flavodoxin gene of *E. coli* prepared in Example 7, pMWPthr-KGS-fpr-fldA, and the control plasmid, pMWPthr, were each introduced into an L-glutamic acid producing *P. ananatis* strain, and culture was performed.

<11-1> Construction of *P. ananatis* L-Glutamic Acid Producing Strain

The plasmid RSFCPG carrying the citrate synthase gene (gltA), the phosphoenolpyruvate carboxylase gene (ppc) and the glutamate dehydrogenase gene (gdhA) of *E. coli* (refer to European Patent Publication No. 1233068) was blunt-ended by digestion with BglII and KpnI and then ligated to eliminate the gltA gene. The *E. coli* JM109 strain was transformed with the obtained plasmid. A plasmid was extracted from a resulting transformant, and designated pRSF-ppc-gdhA. This plasmid pRSF-ppc-gdhA was introduced into the *P. ananatis* NP106 strain, which is an L-glutamic acid producing strain, to construct the strain, NP106/pRSF-ppc-gdhA.

The NP106 strain was obtained as follows. The *P. ananatis* AJ13601 strain described above was cultured overnight at 34° C. in the LBGM9 liquid medium with shaking, and then the medium was diluted so that 100 to 200 colonies appeared per one plate and applied to an LBGM9 plate containing 12.5 mg/L of tetracycline. The colonies which appeared were replicated to an LBGM9 plate containing 12.5 mg/L of tetracycline and 25 mg/L of chloramphenicol, and a strain which became chloramphenicol sensitive was selected to obtain a strain of which pSTVCB was eliminated, which was designated G106S. The G106S strain was further cultured overnight at 34° C. in the LBGM9 liquid medium with shaking, and the medium was diluted so that 100 to 200 colonies appeared per one plate, and applied to an LBGM9 plate containing no drug. The colonies which appeared were replicated to an LBGM9 plate containing 12.5 mg/L of tetracycline and an LBGM9 plate containing no drug, and a strain which became tetracycline sensitive was selected to obtain a strain in which RSFCPG was eliminated, which was designated NP106. The NP106 obtained as described above does not contain both of the plasmids RSFCPG and pSTVCB, which are harbored by the AJ13601 strain.

<11-2> Introduction of a Plasmid for Expressing α-Ketoglutarate Synthase Gene of *C. tepidum*, Flavodoxin NADP$^+$ Reductase Gene and Flavodoxin fldA Gene of *E. coli* into NP106/pRSF-ppc-gdhA Strain Into NP106/pRSF-ppc-gdhA, each of the plasmid for enhancing expressions of the α-ketoglutarate synthase gene, the flavodoxin NADP+ reductase gene of *E. coli* and the flavodoxin or ferredoxin gene of *E. coli*, pMWPthr-KGS-fpr-fldA, and the control plasmid for comparison, pMWPthr, was introduced by electroporation, and transformants were obtained on the basis of kanamycin and tetramycin resistance. After confirming introduction of the plasmids, the plasmid introduced strains were designated NP106/pRSF-ppc-gdhA/pMWPthr-KGS-fpr-fldA and NP106/pRSF-ppc-gdhA/pMWPthr, respectively.

<11-3> Culture of a Strain Introduced with Plasmid for Amplifying α-Ketoglutarate Synthase Gene of *C. tepidum*, Flavodoxin NADP+ Reductase Gene and Flavodoxin fldA Gene of *E. coli* with Glycerol as a Carbon Source Under Aerobic Condition Two of the strains constructed in <11-1> were each cultured overnight at 37° C. in the LBMG medium (LB medium added with 0.5 g/L of glucose, 2 mM $MgSO_4$, 3 g/L of $KH_2PO_4$, 0.5 g/L of NaCl, 1 g/L of $NH_4Cl$ and 6 g/L of $Na_2HPO_4$). Cells corresponding to ¼ of the plate were inoculated to 20 ml of a glycerol medium for *Pantoea* having the following composition in a 500-ml volume Sakaguchi flask, and cultured at 34° C. for 48 hours at 120 rpm. After completion of the culture, L-glutamic acid accumulated in the medium was measured using a Biotech Analyzer (Asahi Chemical Industry).

Composition of Glycerol Medium for *Pantoea*:

| | |
|---|---|
| Glycerol | 40 g/L |
| $MgSO_4 \cdot 7H_2O$ | 1.0 g/L |
| $(NH_4)_2SO_4$ | 20 g/L |
| $KH_2PO_4$ | 2.0 g/L |
| Yeast extract | 2.0 g/L |
| $FeSO_4 \cdot 7H_2O$ | 0.02 g/L |
| $MnSO_4 \cdot 5H_2O$ | 0.02 g/L |
| Thiamine HCl | 0.01 g/L |
| L-lysine | 0.2 g/L |
| DL-diaminopimeric acid | 0.2 g/L |
| L-methionine | 0.2 g/L |
| Kanamycin | 40 mg/L |
| Tetracycline | 2.5 mg/L |
| Calcium carbonate | 20 g/L | pH 7.0 (adjusted with KOH)
Sterilization condition: 120° C., 20 minutes

The results are shown in Table 7. Compared with the control, NP106/pRSF-ppc-gdhA/pMWPthr, improvement of the L-glutamic acid yield by about 3% was observed in the strain in which expressions of the α-ketoglutarate synthase gene of *C. tepidum*, the flavodoxin NADP+ reductase gene of *E. coli* and the flavodoxin gene of *E. coli* were enhanced, NP106/pRSF-ppc-gdhA/pMWPthr-KGS-fpr-fldA.

TABLE 7

| Strain | OD620 | Residual glucose (g/L) | L-Glutamic acid yield (%) |
|---|---|---|---|
| NP106/pRSF-ppc-gdhA/pMWPthr | 8.7 | 0.0 | 40.8 |
| NP106/pRSF-ppc-gdhA/pMWPthr-KGS-fpr-fldA | 10.5 | 0.0 | 44.1 |

Example 12

Effect on L-Glutamic Acid Producing Ability in a Strain in which Expression of α-Ketoglutarate Synthase Gene of *Chlorobium tepidum* is Enhanced with Glucose as a Carbon Source Under Aerobic Conditions The strains prepared in Example 8, the strain in which expression of only the α-ketoglutarate synthase gene of *Chlorobium tepidum* was enhanced, MG1655ΔsucAΔldhA/pMWPthr-KGS, and the control strain MG1655ΔsucAΔldhA/pMWPthr, were used to examine L-glutamic acid producing ability thereof observed with glucose as a carbon source under aerobic conditions.

Cells of each strain precultured overnight at 37° C. on the LB medium were inoculated in an amount corresponding to ¼ of the plate to 20 mL of a glucose+methionine medium (the glucose medium described in Example 5, with a glucose content adjusted to 35.0 g/L, added with 40 mg/L of kanamycin instead of chloramphenicol, and further supplemented with 0.2 g/L DL-methionine) in a 500-mL volume Sakaguchi flask, and cultured at 37° C. for 23 hours at a stirring rate of 120 rpm. After completion of the culture, L-glutamic acid which had accumulated in the medium was measured using a Biotech Analyzer (manufactured by Asahi Kasei Corporation).

The results are shown in Table 8. As compared to the control, MG1655ΔsucAΔldhA/pMWPthr, the yield was improved by about 6% in MG1655ΔsucAΔldhA/pMWPthr-KGS, the strain in which expression of only the α-ketoglutarate synthase gene of *Chlorobium tepidum* was enhanced.

TABLE 8

| Strain | OD620 | Residual glucose (g/L) | L-glutamic acid yield (%) |
|---|---|---|---|
| MG1655ΔsucAΔldh/pMWPthr | 27.3 | 0.0 | 35.5 |
| MG1655ΔsucAΔldh/pMWPthr-KGS | 26.5 | 0.0 | 42.1 |

Example 13

Effect on L-Glutamic Acid Producing Ability in *Pantoea ananatis* in which α-Ketoglutarate Synthase Gene of *Chlorobium tepidum* is Enhanced with Glycerol as Carbon Source Under Aerobic Conditions In order to examine the effect of enhancement of only α-ketoglutarate synthase activity on L-glutamic acid production in *Pantoea ananatis*, the plasmids prepared in Example 7, the plasmid for expressing the α-ketoglutarate synthase gene of *Chlorobium tepidum*, pMWPthr-KGS, and the control plasmid, pMWPthr, were each introduced into an L-glutamic acid producing *Pantoea ananatis* strain, and culture was performed.

Into NP106/pRSF-ppc-gdhA prepared in Example 11, each of the plasmid for expressing the α-ketoglutarate synthase gene prepared in Example 7, pMWPthr-KGS, and the control plasmid, pMWPthr, were introduced by electroporation, and transformants were obtained on the basis of kanamycin and tetramycin resistance. After confirming introduction of the plasmids, the plasmid introduced strains of pMWPthr-KGS and pMWPthr were designated NP106/pRSF-ppc-gdhA/pMWPthr-KGS and NP106/pRSF-ppc-gdhA/pMWPthr, respectively.

The NP106/pRSF-ppc-gdhA/pMWPthr-KGS and NP106/pRSF-ppc-gdhA/pMWPthr were each precultured overnight at 37° C. in the LBMG medium. Cells corresponding to ¼ of the plate were inoculated to 20 ml of a glycerol medium for *Pantoea* having the following composition in a 500-ml volume Sakaguchi flask, and cultured at 34° C. for 66 hours at 100 rpm. After completion of the culture, L-glutamic acid which had accumulated in the medium was measured using a Biotech Analyzer (Asahi Kasei Corporation).

Glycerol culture medium composition for *Pantoea*:

| | |
|---|---|
| Glycerol | 30 g/L |
| MgSO$_4$•7H$_2$O | 0.5 g/L |
| (NH$_4$)$_2$SO$_4$ | 20 g/L |
| KH$_2$PO$_4$ | 2.0 g/L |
| Yeast extract | 2.0 g/L |
| FeSO$_4$•7H$_2$O | 0.02 g/L |
| MnSO$_4$•5H$_2$O | 0.02 g/L |
| Pantothenic acid Ca | 18 mg/L |
| Thiamine HCl | 0.01 g/L |
| L-lysine | 0.2 g/L |
| DL-diamino pimelic acid | 0.2 g/L |
| L-methionine | 0.2 g/L |
| Kanamycin | 40 mg/L |
| Tetracycline | 12.5 mg/L |
| Calcium carbonate | 20 g/L | pH 7.0 (adjusted with KOH)
sterilizing condition: 115° C., 10 minutes

The results are shown in Table 9. As compared to the control, NP106/pRSF-ppc-gdhA/pMWPthr, the yield was improved by about 8% in NP106/pRSF-ppc-gdhA/pMWPthr-KGS, the strain in which expression of the α-ketoglutarate synthase gene of *Chlorobium tepidum* was enhanced.

TABLE 9

| Strain | OD620 | Residual glycerol (g/L) | L-glutamic acid yield (%) |
|---|---|---|---|
| NP106/pRSF-ppc-gdhA/pMWPthr | 8.4 | 0.0 | 47.9 |
| NP106/pRSF-ppc-gdhA/pMWPthr-KGS | 6.9 | 0.0 | 56.2 |

Example 14

Effect on L-Glutamic Acid Producing Ability in *Pantoea ananatis* in which α-Ketoglutarate Synthase Gene of *Chlorobium tepidum* is Enhanced Under Limited Oxygen Concentration with Glycerol as a Carbon Source In order to examine the effect of enhancement of only α-ketoglutarate synthase activity on L-glutamic acid production in *Pantoea ananatis* under microaerobic conditions, NP106/pRSF-ppc-gdhA/pMWPthr-KGS and NP106/pRSF-ppc-gdhA/pMWPthr prepared in Example 13 were cultured with glycerol as a carbon source under microaerobic conditions.

The NP106/pRSF-ppc-gdhA/pMWPthr-KGS and NP106/pRSF-ppc-gdhA/pMWPthr were each precultured overnight at 37° C. in the LBMG medium. Cells corresponding to ¼ of the plate were inoculated to 20 ml of a glycerol medium for *Pantoea* having the following composition in a 500-ml volume Sakaguchi flask, and cultured at 34° C. for 90 hours at 100 rpm. After completion of the culture, L-glutamic acid which had accumulated in the medium was measured using a Biotech Analyzer (Asahi Kasei Corporation).

Glycerol Culture Medium Composition for *Pantoea*:

| | |
|---|---|
| Glycerol | 30 g/L |
| MgSO$_4$•7H$_2$O | 0.5 g/L |
| (NH$_4$)$_2$SO$_4$ | 20 g/L |
| KH$_2$PO$_4$ | 2.0 g/L |
| Yeast extract | 2.0 g/L |
| FeSO$_4$•7H$_2$O | 0.02 g/L |
| MnSO$_4$•5H$_2$O | 0.02 g/L |
| Thiamine HCl | 0.01 g/L |
| Kanamycin | 40 mg/L |
| Tetracycline | 12.5 mg/L |
| Calcium carbonate | 20 g/L | pH 7.0 (adjusted with KOH)
sterilizing condition: 115° C., 10 minutes

The results are shown in Table 10. Compared with the control, NP106/pRSF-ppc-gdhA/pMWPthr, the L-glutamic acid yield was improved by about 30% in NP106/pRSF-ppc-gdhA/pMWPthr-KGS, the strain in which expression of the α-ketoglutarate synthase gene of *Chlorobium tepidum* was enhanced.

TABLE 10

| Strain | OD620 | Residual glycerol (g/L) | L-glutamic acid yield (%) |
|---|---|---|---|
| NP106/pRSF-ppc-gdhA/pMWPthr | 3.5 | 0.0 | 1.1 |
| NP106/pRSF-ppc-gdhA/pMWPthr-KGS | 6.1 | 0.0 | 31.1 |

Example 15

Effect on L-Glutamic Acid Producing Ability in *E. coli* Expressing α-Ketoglutarate Synthase Gene of *Blastopirellula marina* with Glycerol as a Carbon Source In order to examine effect of expression of α-ketoglutarate synthase activity of *B. marina* on L-glutamic acid production with glycerol as a carbon source, a plasmid for expressing the α-ketoglutarate synthase gene of *B. marina* was constructed and introduced into *E. coli* MG1655ΔsucAΔldhA, and culture was performed.

<15-1> Construction of a Plasmid for Expressing α-Ketoglutarate Synthase Gene of *B. marina*

PCR was performed using the genomic DNA of the *B. marina* DSM3645 strain (ATCC 49069) as a template and the oligonucleotides shown in SEQ ID NOS: 61 and 62 to amplify a gene fragment containing the α-subunit and β-subunit of α-ketoglutarate synthase. The obtained gene fragment was digested with KpnI and EcoRI and inserted into pMWPthr digested with KpnI and EcoRI to construct a plasmid for expressing the α-ketoglutarate synthase gene of *B. marina*, which was designated pMWPthr-BlaKGS.

<15-2> Culture of a Strain Expressing α-Ketoglutarate Synthase Gene of *B. marina* with Glycerol as a Carbon Source Under Aerobic Conditions Into MG1655ΔsucAΔldhA, each of pMWPthr-BlaKGS and the control vector pMWPthr was introduced by electroporation, and transformants were obtained on the basis of kanamycin resistance. After confirming introduction of the plasmids, the strain expressing the α-ketoglutarate synthase gene of B. marina and the control strain were designated MG1655ΔsucAΔldhA/pMWPthr-BlaKGS and MG1655ΔsucAΔldhA/pMWPthr, respectively.

MG1655ΔsucAΔldhA/pMWPthr-BlaKGS and the control strain MG1655ΔsucAΔldhA/pMWPthr were inoculated to the LB medium and precultured overnight at 37° C. Cells corresponding to ½ of the plate were inoculated to 20 mL of a glycerol medium having the following composition in a 500-mL volume Sakaguchi flask, and cultured at aerobically 37° C. for 22 hours at a stirring rate of 120 rpm. After completion of the culture, L-glutamic acid which had accumulated in the medium was measured using a Biotech Analyzer (Asahi Kasei Corporation).

Glycerol Culture Medium Composition:

| | |
|---|---|
| Glycerol | 30 g/L |
| MgSO$_4$•7H$_2$O | 1.0 g/L |
| (NH$_4$)$_2$SO$_4$ | 20 g/L |
| KH$_2$PO$_4$ | 1.0 g/L |
| Yeast extract | 2.0 g/L |
| FeSO$_4$•7H$_2$O | 0.01 g/L |
| MnSO$_4$•5H$_2$O | 0.01 g/L |
| Thiamine HCl | 0.01 g/L |
| Kanamycin | 40 mg/L |
| Calcium carbonate | 30 g/L | pH 7.0 (adjusted with KOH)
sterilizing condition: 120° C., 20 minutes

The results are shown in Table 11. As compared to the control MG1655ΔsucAΔldhA/pMWPthr, L-glutamic acid yield with respect to consumed glycerol was improved by about 8% in MG1655ΔsucAΔldhA/pMWPthr-BlaKGS introduced with the expression vector including only the α-ketoglutarate synthase gene of B. marina.

TABLE 11

| Strain | OD620 | Residual glycerol (g/L) | L-glutamic acid yield (%) |
|---|---|---|---|
| MG1655ΔsucAΔldh/pMWPthr | 20.4 | 0.0 | 40.6 |
| MG1655ΔsucAΔldh/ pMWPthr-BlaKGS | 24.0 | 0.0 | 48.7 |

Example 16

Effect on L-Glutamic Acid Producing Ability in a Strain in which Expression of α-Ketoglutarate Synthase Gene of B. marina is Enhanced with Glucose as a Carbon Source Under Aerobic Conditions The strain in which expression of the α-ketoglutarate synthase gene of B. marina was enhanced and prepared in Example 15, MG1655ΔsucAΔldhA/pMWPthr-BlaKGS, and the control strain MG1655ΔsucAΔldhA/pMWPthr, were used to examine L-glutamic acid producing ability thereof observed with glucose as a carbon source.

Cells of each strain precultured overnight at 37° C. on the LB medium were inoculated in an amount corresponding to ½ of the plate to 20 mL of a glucose+methionine medium (the glucose medium described in Example 5, with a glucose content adjusted to 30.0 g/L, supplemented with 40 mg/L of kanamycin instead of chloramphenicol, and further supplemented with 0.2 g/L DL-methionine) in a 500-mL volume Sakaguchi flask, and cultured at 37° C. for 24 hours at a stirring rate of 120 rpm. After completion of the culture, L-glutamic acid which had accumulated in the medium was measured using a Biotech Analyzer (manufactured by Asahi Kasei Corporation).

The results are shown in Table 12. Compared with the control, MG1655ΔsucAΔldhA/pMWPthr, the yield was improved by about 6% in MG1655ΔsucAΔldhA/pMWPthr-KGS, the strain in which expression of only the α-ketoglutarate synthase gene of B. marina was enhanced.

TABLE 12

| Strain | OD620 | Residual glucose (g/L) | L-glutamic acid yield (%) |
|---|---|---|---|
| MG1655ΔsucAΔldh/pMWPthr | 18.9 | 0.0 | 34.3 |
| MG1655ΔsucAΔldh/ pMWPthr-BlaKGS | 14.5 | 0.0 | 40.4 |

Example 17

Construction of 2256ΔldhΔsucA Strain from Wild-Type Strain of B. lactofermentum

A strain which is deficient in a sucA (odhA) gene encoding the E1o subunit of α-ketoglutarate dehydrogenase was constructed from 2256Δldh strain (see WO2005/113744) which had been obtained from Brevibacterium lactofermentum (Corynebacterium glutamicum) ldhA deficient strain, the 2256 strain (ATCC13869).

A gene fragment with a deletion in ORF of E1o subunit gene of α-ketoglutarate dehydrogenase derived from B. lactofermentum 2256 strain (hereinafter, abbreviated as sucA gene) was obtained by crossover PCR using synthetic DNAs designed based on the disclosed nucleotide sequence of the gene of C. glutamicum ATCC13032 (GenBank Database Accession No. NC_003450) (SEQ ID NO: 51) as primers. Specifically, PCR was performed in accordance with a conventional method using the genomic DNA of B. lactofermentum 2256 strain as a template and the synthetic DNAs of SEQ ID NOS: 63 and 64 as primers to obtain an amplified product of the N-terminus of the sucA gene. On the other hand, in order to obtain an amplified product of the C-terminus of the sucA gene, PCR was performed in accordance with a conventional method using the genomic DNA of B. lactofermentum 2256 strain as a template and the synthetic DNAs of SEQ ID NOS: 65 and 66 as primers. SEQ ID NOS: 64 and 65 are complementary to each other.

Subsequently, the gene products of the N-terminus and C-terminus of sucA were mixed in an about equimolar amount and used as a template in PCR in accordance with a conventional method using the synthetic DNAs of SEQ ID NOS: 63 and 66 as primers to obtain a sucA gene-amplified product where a mutation was introduced. Thus, a sucA gene-amplified fragment with most of its internal sequence deleted was obtained. The resultant PCR product was purified in accordance with a conventional method and digested with BamHI, followed by insertion into the SalI site of pBS3 described in WO2005/113744. The DNA was transformed into competent cells of E. coli JM109 (TAKARA BIO INC.), and the cells were applied to LB medium containing 100 μM of IPTG, 40 μg/mL of X-Gal, and 25 μg/mL of Km and cultured overnight. Thereafter, white colonies being generated were separated, and a single colony was then isolated, thereby obtaining a transformant. Plasmids were extracted from the obtained transformant, and a plasmid where a PCR product of interest had been inserted was designated pΔsucA56-1.

The pΔsucA56-1 does not include a region that allows coryneform bacteria to autonomously replicate in cells, and in the case where a coryneform bacterium is transformed with the plasmid, a strain having the genomic DNA integrated with the plasmid by homologous recombination appears as a transformant, although at an extremely low frequency. B. lactofermentum 2256 strain was transformed with a high level of the plasmid pΔldh56-1 by the electric pulse method and applied to the CM-Dex medium containing 25 µg/ml kanamycin, and culture was performed at 31.5° C. for about 30 hours. The strain which grows on the medium is a strain having the genome where a kanamycin-resistant gene and sacB gene derived from the plasmid was inserted by homologous recombination between an ldh gene fragment of the plasmid and the gene on the genome of B. lactofermentum 2256 strain.

CM-Dex Culture Medium:

| Glucose | 5 g/L |
| Polypeptone | 10 g/L |
| Yeast extract | 10 g/L |
| KH$_2$PO$_4$ | 1 g/L |
| MgSO$_4$•7H$_2$O | 0.4 g/L |
| FeSO$_4$•7H$_2$O | 0.01 g/L |
| MnSO$_4$•7H$_2$O | 0.01 g/L |
| Urea | 3 g/L |
| Soybean hydrolysate | 1.2 g/L |
| Biotin | 10 µg/L | pH 7.5 (adjusted with NaOH)
sterilizing condition: 120° C., 20 minutes

Then, the first recombinant was cultured in the CM-Dex liquid medium containing no kanamycin at 31.5° C. overnight and appropriately diluted, and the resultant was applied to the 10% sucrose containing Dex-S10 medium not containing kanamycin (CM-Dex medium containing 10 g/L sucrose instead of glucose) and cultured at 31.5° C. for about 30 hours. As a result, about 60 strains, which were thought to be sucrose-insensitive due to elimination of the sacB gene by a second homologous recombination, were obtained.

The strains thus obtained include a strain in which the sucA gene was replaced by the deficient-type derived from pΔsucA56-1 and a strain in which the sucA gene reverted to the wild type. Whether the sucA gene is the mutant type or the wild type can be confirmed easily by directly subjecting the cells obtained by culturing on Dex-S10 agar medium to PCR and detecting their sucA gene. In PCR analysis using the primers (SEQ ID NOS: 63 and 66) for amplifying sucA gene, a strain which yielded a PCR product having a smaller size than the size of a product obtained by PCR using a genomic DNA of the 2256 strain as a template was defined as a sucA-deficient strain and used in the following experiments. As a result of the analysis of the sucrose-insensitive strains by the above-mentioned method, a strain containing only the sucA gene was selected and designated 2256ΔldhΔsucA strain.

Example 18

Effect on L-Glutamic Acid Producing Ability in B. lactofermentum Expressing α-Ketoglutarate Synthase Gene of Chlorobium tepidum Under Limited Oxygen Concentration with Glycerol as a Carbon Source In order to examine the effect of the expression of α-ketoglutarate synthase activity of Chlorobium tepidum on L-glutamic acid production in B. lactofermentum with glucose as a carbon source, a plasmid for expressing the α-ketoglutarate synthase gene of Chlorobium tepidum was constructed and introduced into B. lactofermentum 2256ΔldhΔsucA strain, and culture was performed.

<18-1> Construction of Plasmid for Expressing α-Ketoglutarate Synthase Gene of Chlorobium tepidum A KGS gene fragment with substitution of a tuf promoter for the upstream of the gene was obtained by crossover PCR using, as primers, synthetic DNAs designed based on the disclosed nucleotide sequences around the tuf gene and KGS gene of C. glutamicum ATCC13032 (GenBank Database Accession No. NC_003450).

Specifically, a KGS fragment was amplified by PCR using pMWPthr-KGS-fpr-fldA, the plasmid for expressing the α-ketoglutarate synthase gene of Chlorobium tepidum and for enhancing expression of the ferredoxin-NADP$^+$ reductase gene and flavodoxin (fldA) gene of E. coli constructed in Example 7, as a template, and using the primers shown in SEQ ID NOS: 67 and 68. The resulting amplified fragment was treated with PstI and XbaI, followed by insertion into the PstI and XbaI sites of pVK9 to construct a plasmid pVKKGS carrying KGS. If the plasmid is treated with PstI and AatII, it is possible to excise a part of the ORF of KGS.

A fragment (A) including the N-terminal sequence of KGS is amplified by PCR using the plasmid pMWPthr-KGS-fpr-fldA constructed in Example 7 as a template and using the primers shown in SEQ ID NOS: 69 and 70. On the other hand, a tuf promoter fragment (B) was amplified by PCR using the DNA of the plasmid pVKPtuf as a template and using the primers shown in SEQ ID NOS: 71 and 72. SEQ ID NOS 69 and 72 are complementary to each other.

Subsequently, crossover PCR was performed using the fragments (A) and (B) as templates and using the primers shown in SEQ ID NOS: 73 and 74 to construct a fragment containing the N-terminal sequence of KGS in which the inherent promoter is replaced with the tuf promoter. The resultant PCR products were purified in accordance with a conventional method and treated with PstI and AatII, followed by insertion into the PstI and AatII sites of pVKKGS to construct a plasmid pVKPtuf-KGS for amplifying KGS with substitution of a tuf gene promoter for the inherent promoter.

The pVK9 is a shuttle vector inserted with fragments obtained by: blunt-ending the AvaII site of pHSG299 (TAKARA BIO INC.); and excising a region that is in pHK4 (JP 05-007491 A) and is autonomously replicable in coryneform bacteria with BamHI and KpnI and blunt-ending the sites. Meanwhile, pVKPtuf for comparison is a plasmid constructed by inserting a tuf promoter fragment amplified by PCR using the genome of B. flavum MJ-233 strain (FERM BP-1497) as a template and the primers shown in SEQ ID NOS: 75 and 76 into the PstI site of pVK. The tuf promoter sequence of B. flavum MJ-233 strain is shown in SEQ ID NO: 77. Similarly, the tuf promoter fragment can also be obtained using genomic DNA of Corynebacterium glutamicum ATCC13032 strain as a template.

<18-2> Introduction of α-Ketoglutarate Synthase Gene of Chlorobium tepidum into 2256ΔldhAΔsucA strain Into 2256ΔldhAΔsucA, each of pVKPtuf-KGS and the control vector pVKPtuf was introduced by electroporation, and transformants were obtained on the basis of kanamycin resistance. After confirming introduction of the plasmids, the strain expressing the α-ketoglutarate synthase gene of Chlorobium tepidum and the control strain were designated 2256ΔldhAΔsucA/pVKPtuf-KGS and 2256ΔldhAΔsucA/pVKPtuf, respectively.

<18-3> Culture of a Strain Expressing α-Ketoglutarate Synthase Gene of *Chlorobium tepidum* with Glycerol as a Carbon Source Under Anaerobic Condition The strains constructed in <18-2>, the strain expressing the α-ketoglutarate synthase gene of *Chlorobium tepidum*, 2256ΔldhAΔsucA/pVKPtuf-KGS, and the control strain 2256ΔldhAΔsucA/pVKPtuf, were used to examine L-glutamic acid producing ability thereof observed with glucose as a carbon source under anaerobic culture conditions. Cells precultured on the CM-Dex agar medium at 31.5° C. overnight were inoculated to 3 ml of a seed medium and cultured with shaking in a test tube at 31.5° C. for about 16 hours under aerobic conditions.

Seed Culture Medium:

| | |
|---|---|
| Glucose | 10 g/L |
| $(NH_4)_2SO_4$ | 2.5 g/l |
| $KH_2PO_4$ | 0.5 g/L |
| $MgSO_4 \cdot 7H_2O$ | 0.25 g/L |
| Urea | 2 g/L |
| $FeSO_4 \cdot 7H_2O$ | 0.01 g/L |
| $MnSO_4 \cdot 7H_2O$ | 0.01 g/L |
| Biotin | 50 μg/L |
| VB1•HCl | 100 μg/L |
| Protocatechuic acid | 15 mg/L |
| $CuSO_4$ | 0.02 mg/L |
| $CaCl_2$ | 10 mg/L | pH 7.0 (adjusted with KOH)
sterilizing condition: 115° C., 10 minutes]

To 3 mL of a seed culture broth was added with 3 mL of a main medium. A test tube was plugged with a silicone stopper to inhibit ventilation, followed by shaking culture at 31.5° C. 66 hours later. Culture was stopped, and L-glutamic acid which had accumulated in the medium was measured using a Biotech Analyzer (manufactured by Asahi Kasei Corporation).

Main Culture Medium:

| | |
|---|---|
| Glucose | 60 g/L |
| $(NH_4)_2SO_4$ | 30 g/l |
| $KH_2PO_4$ | 4 g/L |
| Urea | 6 g/L |
| $FeSO_4 \cdot 7H_2O$ | 0.02 g/L |
| $MnSO_4 \cdot 7H_2O$ | 0.02 g/L |
| Biotin | 400 μg/L |
| VB1•HCl | 400 μg/L |
| $MgCO_4$ | 50 g/L | pH 6.8 (adjusted with NaOH)
sterilizing condition: 115° C., 10 minutes

The results are shown in Table 13. Compared with the control 2256ΔIdhΔsucA/pVKPtuf, L-glutamic acid yield with respect to consumed glucose was improved by about 0.6% in 2256ΔIdhΔsucA/pVKPtuf-KGS introduced with the expression vector including only the α-ketoglutarate synthase gene of *Chlorobium tepidum*.

TABLE 13

| Strain | OD620 | Residual glucose (g/L) | L-glutamic acid yield (%) |
|---|---|---|---|
| 2256ΔIdhΔsucA/pVKPtuf | 7.6 | 0.48 | 3.1 |
| 2256ΔIdhΔsucA/pVKPtuf-KGS | 6.6 | 6.02 | 3.7 |

Explanation of Sequence Listing:
SEQ ID NO: 1: nucleotide sequence of *Chlorobium tepidum* α-ketoglutarate synthase α-subunit gene
SEQ ID NO: 2: amino acid sequence of *Chlorobium tepidum* α-ketoglutarate synthase α-subunit
SEQ ID NO: 3: nucleotide sequence of *Chlorobium tepidum* α-ketoglutarate synthase β-subunit gene
SEQ ID NO: 4: amino acid sequence of *Chlorobium tepidum* α-ketoglutarate synthase β-subunit
SEQ ID NO: 5: nucleotide sequence of *Escherichia coli* fpr gene
SEQ ID NO: 6: amino acid sequence encoded by *Escherichia coli* fpr gene
SEQ ID NO: 7: nucleotide sequence of *Chlorobium tepidum* pyruvate synthase gene
SEQ ID NO: 8: amino acid sequence of *Chlorobium tepidum* pyruvate synthase
SEQ ID NO: 9: nucleotide sequence of *Escherichia coli* fdx gene
SEQ ID NO: 10: amino acid sequence encoded by *Escherichia coli* fdx gene
SEQ ID NO: 11: nucleotide sequence of *Escherichia coli* yfhL gene
SEQ ID NO: 12: amino acid sequence encoded by *Escherichia coli* yfhL gene
SEQ ID NO: 13: nucleotide sequence of *Escherichia coli* fldA gene
SEQ ID NO: 14: amino acid sequence encoded by *Escherichia coli* fldA gene
SEQ ID NO: 15: nucleotide sequence of *Escherichia coli* fldB gene
SEQ ID NO: 16: amino acid sequence encoded by *Escherichia coli* fldB gene
SEQ ID NO: 17: nucleotide sequence of *Chlorobium tepidum* ferredoxin I gene
SEQ ID NO: 18: amino acid sequence encoded by *Chlorobium tepidum* ferredoxin I gene
SEQ ID NO: 19: nucleotide sequence of *Chlorobium tepidum* ferredoxin II gene
SEQ ID NO: 20: amino acid sequence encoded by *Chlorobium tepidum* ferredoxin II gene
SEQ ID NO: 21: primer 1 for amplification of *Chlorobium tepidum* α-ketoglutarate synthase gene
SEQ ID NO: 22: primer 2 for amplification of *Chlorobium tepidum* α-ketoglutarate synthase gene
SEQ ID NO: 23: primer 1 for amplification of *Chlorobium tepidum* pyruvate synthase gene
SEQ ID NO: 24: primer 2 for amplification of *Chlorobium tepidum* pyruvate synthase gene
SEQ ID NO: 25: primer 1 for amplification of *Chlorobium tepidum* ferredoxin I gene
SEQ ID NO: 26: primer 2 for amplification of *Chlorobium tepidum* ferredoxin I gene
SEQ ID NO: 27: primer 1 for deletion of ldhA
SEQ ID NO: 28: primer 2 for deletion of ldhA
SEQ ID NO: 29: primer 1 for confirmation of ldhA deficiency
SEQ ID NO: 30: primer 2 for confirmation of ldhA deficiency
SEQ ID NO: 31: threonine operon promoter sequence
SEQ ID NO: 32: primer 1 for amplification of *Escherichia coli* flavodoxin $NADP^+$ reductase gene
SEQ ID NO: 33: primer 2 for amplification of *Escherichia coli* flavodoxin $NADP^+$ reductase gene
SEQ ID NO: 34: primer 1 for amplification of *Escherichia coli* fldA gene
SEQ ID NO: 35: primer 2 for amplification of *Escherichia coli* fldA gene SEQ ID NO: 36: primer 1 for amplification of *Escherichia coli* fldB gene
SEQ ID NO: 37: primer 2 for amplification of *Escherichia coli* fldB gene
SEQ ID NO: 38: primer 1 for amplification of *Escherichia coli* fdx gene
SEQ ID NO: 39: primer 2 for amplification of *Escherichia coli* fdx gene
SEQ ID NO: 40: primer 1 for amplification of *Escherichia coli* yhfL gene
SEQ ID NO: 41: primer 2 for amplification of *Escherichia coli* yfhL gene
SEQ ID NO: 42: PCR primer for amplification of sucA gene N-terminus fragment
SEQ ID NO: 43: PCR primer for amplification of sucA gene N-terminus fragment
SEQ ID NO: 44: PCR primer for amplification of sucA gene C-terminus fragment
SEQ ID NO: 45: PCR primer for amplification of sucA gene C-terminus fragment
SEQ ID NO: 46: nucleotide sequences of *Pantoea ananatis* α-KGDH subunit gene and neighboring genes
  sdhB: 2 to 121
  sucA: 322 to 3129
  sucB: 3145 to 4368
  sucC: 4437 to 4556
SEQ ID NO: 47: amino acid sequence of succinate dehydrogenase iron-sulfur protein (partial sequence)
SEQ ID NO: 48: amino acid sequence of *Pantoea ananatis* α-KGDH E1o-subunit
SEQ ID NO: 49: amino acid sequence of *Pantoea ananatis* α-KGDH E2o-subunit
SEQ ID NO: 50: part of succinyl-CoA synthetase β-subunit of *Pantoea ananatis*
SEQ ID NO: 51: nucleotide sequence of *Brevibacterium lactofermentum* odhA gene
SEQ ID NO: 52: amino acid sequence of E1o-subunit encoded by *Brevibacterium lactofermentum* odhA
SEQ ID NO: 53: nucleotide sequence of gene encoding *Brevibacterium lactofermentum* E2o-subunit (NCgl2126 of GenBank Accession No. NC_003450)
SEQ ID NO: 54: amino acid sequence of *Brevibacterium lactofermentum* E2o-subunit encoded by NCgl2126
SEQ ID NO: 55: nucleotide sequence of *Escherichia coli* sucA gene
SEQ ID NO: 56: amino acid sequence of α-KGDH E1 subunit encoded by *Escherichia coli* sucA gene
SEQ ID NO: 57: nucleotide sequence of *Blastopirellula marina* α-ketoglutarate synthase α-subunit gene
SEQ ID NO: 58: amino acid sequence of *Blastopirellula marina* α-ketoglutarate synthase α-subunit
SEQ ID NO: 59: nucleotide sequence of *Blastopirellula marina* α-ketoglutarate synthase β-subunit gene
SEQ ID NO: 60: amino acid sequence of *Blastopirellula marina* α-ketoglutarate synthase β-subunit
SEQ ID NO: 61: primer 1 for amplification of *Blastopirellula marina* α-ketoglutarate synthase gene
SEQ ID NO: 62: primer 2 for amplification of *Blastopirellula marina* α-ketoglutarate synthase gene
SEQ ID NO: 63: PCR primer 1 for amplification of sucA gene N-terminus fragment of *Brevibacterium lactofermentum*
SEQ ID NO: 64: PCR primer 2 for amplification of sucA gene N-terminus fragment of *Brevibacterium lactofermentum*
SEQ ID NO: 65: PCR primer 1 for amplification of sucA gene C-terminus fragment of *Brevibacterium lactofermentum*
SEQ ID NO: 66: PCR primer 2 for amplification of sucA gene C-terminus fragment of *Brevibacterium lactofermentum*
SEQ ID NO: 67: primer 1 for amplification of entire α-ketoglutarate synthase gene of *Chlorobium tepidum*
SEQ ID NO: 68: primer 2 for amplification of entire α-ketoglutarate synthase gene of *Chlorobium tepidum*
SEQ ID NO: 69: primer 1 for amplification of α-ketoglutarate synthase gene N-terminus fragment of *Chlorobium tepidum*
SEQ ID NO: 70: primer 2 for amplification of α-ketoglutarate synthase gene N-terminus fragment of *Chlorobium tepidum*
SEQ ID NO: 71: primer 1 for amplification of tuf promoter of *Brevibacterium flavum*
SEQ ID NO: 72: primer 2 for amplification of tuf promoter of *Brevibacterium flavum*
SEQ ID NO: 73: primer 1 for amplification of Ptuf-KGS fragment
SEQ ID NO: 74: primer 2 for amplification of Ptuf-KGS fragment
SEQ ID NO: 75: primer 3 for amplification of tuf promoter of *Brevibacterium flavum*
SEQ ID NO: 76: primer 4 for amplification of tuf promoter of *Brevibacterium flavum*
SEQ ID NO: 77: nucleotide sequence of tuf promoter of *Brevibacterium flavum*

INDUSTRIAL APPLICABILITY

Amino acids of the L-glutamic acid family can be efficiently produced by fermentation using a microorganism in accordance with the presently disclosed subject matter. Furthermore, a method in accordance with the presently disclosed subject matter can be an environment friendly method, which can decrease carbon dioxide emission by suppressing decarboxylation and using a carbon dioxide fixation reaction.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid comprising culturing a microorganism which is able to produce an L-amino acid in a medium to produce and accumulate the L-amino acid in the medium or the cells of the microorganism, and collecting the L-amino acid from the medium or the cells,
   wherein the L-amino acid is selected from the group consisting of L-glutamic acid, L-glutamine, L-proline, L-ornithine, L-citrulline, L-arginine, and combinations thereof, and
   wherein the microorganism has been modified to increase α-ketoglutarate synthase activity.

2. The method according to claim 1, wherein the microorganism is cultured under aerobic conditions.

3. The method according to claim 1, wherein the medium contains carbonate ions, bicarbonate ions, or carbon dioxide, and the microorganism is cultured under anaerobic or micro aerobic conditions.

4. The method according to claim 1, wherein the α-ketoglutarate synthase activity is increased by increasing expression of a gene encoding α-ketoglutarate synthase and/or by increasing translation of the gene.

5. The method according to claim 4, wherein the expression of the gene encoding α-ketoglutarate synthase is increased by increasing the copy number of the gene or by modifying an expression control sequence of the gene.

6. The method according to claim 1, wherein said α-ketoglutarate synthase comprises an α subunit and a β subunit, and the α subunit is selected from the group consisting of:
   (A) a polypeptide comprising the amino acid sequence of SEQ ID NO: 2,
   (B) a polypeptide comprising the amino acid sequence of SEQ ID NO: 2, but which includes substitutions, deletions, insertions or additions of one to 5 amino acids, and wherein said polypeptide has α-ketoglutarate synthase activity when complexed with the β subunit,
   (C) a polypeptide comprising the amino acid sequence of SEQ ID NO: 58, and
   (D) a polypeptide comprising the amino acid sequence of SEQ ID NO: 58, but which includes substitutions, deletions, insertions or additions of one to 5 amino acids, and wherein said polypeptide has α-ketoglutarate synthase activity when complexed with the β subunit;
   and the β subunit is selected from the group consisting of:
   (a) a polypeptide comprising the amino acid sequence of SEQ ID NO: 4,
   (b) a polypeptide comprising the amino acid sequence of SEQ ID NO: 4, but which includes substitutions, deletions, insertions or additions of one to 5 amino acids, and wherein said polypeptide has α-ketoglutarate synthase activity when complexed with the α subunit,
   (c) a polypeptide comprising the amino acid sequence of SEQ ID NO: 60, and
   (d) a polypeptide comprising the amino acid sequence of SEQ ID NO: 60, but which includes substitutions, deletions, insertions or additions of one to 5 amino acids, and wherein said polypeptide has α-ketoglutarate synthase activity when complexed with the α subunit.

7. The method according to claim 1, wherein said α-ketoglutarate synthase comprises an α subunit and a β subunit, and the gene encoding the α-subunit comprises a DNA selected from the group consisting of:

(a) a DNA comprising the nucleotide sequence of SEQ ID NO: 1,
(b) a DNA that is able to hybridize with a sequence complementary to the nucleotide sequence of SEQ ID NO: 1 under stringent conditions comprising washing in 0.1× SSC, 0.1% SDS at 60° C., and encodes a polypeptide that has α-ketoglutarate synthase activity when complexed with the β subunit,
(c) a DNA comprising the nucleotide sequence of SEQ ID NO: 57, and
(d) a DNA that is able to hybridize with a sequence complementary to the nucleotide sequence of SEQ ID NO: 57 under stringent conditions comprising washing at 60° C., 0.1×SSC, 0.1% SDS, and encodes a polypeptide that has α-ketoglutarate synthase activity when complexed with the β subunit;

and the gene encoding the β-subunit comprises a DNA selected from the group consisting of:

(e) a DNA comprising the nucleotide sequence of SEQ ID NO: 3,
(f) a DNA that is able to hybridize with a sequence complementary to the nucleotide sequence of SEQ ID NO: 3 under stringent conditions comprising washing in 0.1× SSC, 0.1% SDS at 60° C., and encodes a polypeptide that has α-ketoglutarate synthase activity when complexed with the α subunit,
(g) a DNA comprising the nucleotide sequence of SEQ ID NO: 59, and
(h) a DNA that is able to hybridize with a sequence complementary to the nucleotide sequence of SEQ ID NO: 59 under stringent conditions comprising washing in 0.1× SSC, 0.1% SDS at 60° C., and encodes a polypeptide that has α-ketoglutarate synthase activity when complexed with the α subunit.

8. The method according to claim 1, wherein the microorganism has been modified to increase ferredoxin $NADP^+$ reductase activity.

9. The method according to claim 1, wherein the microorganism has been modified to increase pyruvate synthase activity.

10. The method according to claim 1, wherein the microorganism has been modified to increase production of ferredoxin or flavodoxin.

11. The method according to claim 1, wherein the microorganism has been modified to decrease α-ketoglutarate dehydrogenase activity.

12. The method according to claim 1, wherein the microorganism is a bacterium belonging to a genus selected from the group consisting of *Escherichia, Enterobacter, Pantoea, Klebsiella*, and *Serratia*.

13. The method according to claim 1, wherein the microorganism is a coryneform bacterium.

14. The method according to claim 12, wherein the microorganism is *Escherichia coli* or *Pantoea ananatis*.

15. The method according to claim 13, wherein the microorganism is *Corynebacterium glutamicum*.

* * * * *